(12) United States Patent
Seidah et al.

(10) Patent No.: US 8,673,850 B2
(45) Date of Patent: Mar. 18, 2014

(54) PCSK9 INHIBITORS AND METHODS OF USE THEREOF

(75) Inventors: Nabil G. Seidah, Verdun (CA); Gaétan Mayer, Montreal (CA); Steve Poirier, Montreal (CA)

(73) Assignee: Institut de Recherches Cliniques de Montreal, Montreal (CA)

( * ) Notice: Subject to any disclaimer, the term of this patent is extended or adjusted under 35 U.S.C. 154(b) by 362 days.

(21) Appl. No.: 12/994,835

(22) PCT Filed: Jun. 1, 2009

(86) PCT No.: PCT/CA2009/000764
§ 371 (c)(1),
(2), (4) Date: Jan. 20, 2011

(87) PCT Pub. No.: WO2009/143633
PCT Pub. Date: Dec. 3, 2009

(65) Prior Publication Data
US 2011/0118181 A1    May 19, 2011

Related U.S. Application Data

(60) Provisional application No. 61/057,548, filed on May 30, 2008.

(51) Int. Cl.
| | |
|---|---|
| *A61K 38/00* | (2006.01) |
| *A61P 3/06* | (2006.01) |
| *C12N 5/00* | (2006.01) |
| *C12N 5/02* | (2006.01) |
| *C07K 5/00* | (2006.01) |
| *C07K 7/00* | (2006.01) |
| *C07K 16/00* | (2006.01) |
| *C07K 17/00* | (2006.01) |
| *C12P 21/08* | (2006.01) |
| *C07H 21/04* | (2006.01) |

(52) U.S. Cl.
USPC ......... 514/7.4; 435/375; 530/324; 530/387.9; 536/23.5

(58) Field of Classification Search
None
See application file for complete search history.

(56) References Cited

U.S. PATENT DOCUMENTS

| | | | |
|---|---|---|---|
| 6,025,155 | A | 2/2000 | Hadlaczky |
| 6,077,677 | A | 6/2000 | Hodgson et al. |
| 6,204,023 | B1 | 3/2001 | Robinson et al. |
| 2002/0160970 | A1 | 10/2002 | Hadlaczky |
| 2003/0083293 | A1 | 5/2003 | Hadlaczky |

OTHER PUBLICATIONS

Seidah N "PCSK9 as a therapeutic target of dyslipidemia" Expert Opinion Therapeutic Targets 13:19-28. Published Jan. 2009.*
Mayer et al "Annexin A2 is a C-terminal PCSK9-binding Protein That Regulates Endogenous Low Density Lipoprotein Receptor Levels" J Biol Chem 46:31791-31801. Published Nov. 14, 2008.*
Abifadel M. et al., Mutations in PCSK9 cause autosomal dominant hypercholesterolemia. Nature Genetics, 2003, 34(2), 154-156.
Benjannet S. et al., NARC-1PCSK9 and its natural mutants. J. of Biol. Chem, 2004, 279(47), 48865-75.
Benjannet S. et al., The Proprotein Convertase (PC) PCSK9 is inactived by Furin and/or PC5/6A. J. of Biol. Chem., 2006, 281(41), 30561-572.
Cameron J. et al., Effect of mutations in the PCSK9 gene on the cell surface LDL receptors. Hum. Mol. Gen., 2006, 15(9), 1551-58.
Chetcuti A. et al., Loss of Annexin II Heavy and Light Chains in Prostate Cancer and its Precursors. Cancer Res., 2001, 61, 6331-34.
Cohen J., Low LDL cholesterol in individuals of African descent resulting from frequent nonsense mutations in PCSK9. Nat Gen., 2005, 37(2), 161-165.
Cunningham D. et al., Structural and biophysical studies of PCSK9 and its mutants linked to familial hypercholesterolemia. Nat. Struc. & Mol. Biol., 2007, 14(5), 413-419.
ISR and WO, WO, Oct. 31, 2009, Seidah et al.
IPRP, WO, Dec. 9, 2010.
Dubuc G. et al., Statins upregulate PCSK9, the gene encoding the proprotein convertase neural apoptosis-regulated convertase-1 implicated in familial hypercholesterolemia. Arterioscler Thromb. Vasc. Biol., 2004, 24, 1454-59.
Görg A. et al., The current state of two-dimensional electrophoresis with immobilized pH gradients. *Electrophoresis*, 2000, 21, 1037-1053.
Horton J.D. et al., Molecular biology of PCSK9: its role in LDL metabolism. Trends Biochem Sci., 2007, 32(2), 71-77.
Kassam G. et al., The p11 subunit of the Annexin II Tetramer plays a key role in the stimulation of t-PA-Dependent Plasminogen Activation. Biochemistry. 1998, 37, 16958-966.
Kathiresan S. et al., Six new loci associated with blood low-density lipoprotein cholesterol, high-density lipoprotein cholesterol or triglycerides in humans. Nat. Genet. 2008, 40(2), 189-197.
Kotowski I.K. et al. A spectrum of PCSK9 alleles contributes to plasma levels of low-density lipoprotrein cholesterol. The Amer. J. of Hum. Gen., 2006, 78, 410-422.
Labonté P. et al., PCSK9 impedes hepatitis C virus infection in In Vitro and modulates liver CD81 expression. Hepatology, 2009, 50, 17-24.
Li J. et al., Secreted PCSK9 promotes LDL receptor degradation independently of proteolytic activity. Biochem. J., 2007, 406, 203-207.
Ling Q. et al., Annexin II regulates fibrin homeostasis and neoangiogenesis in vivo. J. Clin. Invest., 2004, 113, 38-48.

(Continued)

*Primary Examiner* — Cecilia J Tsang
*Assistant Examiner* — Zachary J Miknis
(74) *Attorney, Agent, or Firm* — Goudreau Gage Dubuc; Julie Gauvreau

(57) ABSTRACT

A method for identifying a compound for preventing or treating a LDLR-associated disease, a VLDLR-associated disease or an ApoER2-associated disease, said method comprising determining whether: a) a level of expression of Annexin A2 nucleic acid or encoded polypeptide; b) a level of Annexin A2 activity; or c) a combination of a) and b), is increased in the presence of a test compound relative to in the absence of said test compound, wherein said increase is indicative that said test compound can be used for preventing or treating a LDLR-associated disease, a VLDLR-associated disease, an ApoER2-associated disease.

11 Claims, 20 Drawing Sheets

(56) References Cited

OTHER PUBLICATIONS

Mai J. et al., Cell surface complex of cathepsin B/annexin II tetramer in malignant progression. Biochimica et Biophysica Acta, 2000, 1477, 215-230.

Mayer G. et al., The regulated cell surface zymogen activation of the proprotein convertase PC5A directs the processing of its secretory substrates. J. Biol. Chem, 2008, 283(4), 2373-84.

Mayer G. et al., Annexin A2 is a C-terminal PCSK9-binding protein that regulates endogenous low density lipoprotein receptor levels. J. Biol Chem., 2008, 283(46), 31791-801.

Maxwell K.N. et al., Adenoviral-mediated expression of PCSK9 in mice resuls in a low-density lipoprotein receptor knockout phenotype. PNAS, 2004, 101(18), 7100-7105.

McNutt M.C. et al., Catalytic activity is not required for secreted PCSK9 to reduce low density lipoprotein receptors in HepG2 cells. J. Biol. Chem., 2007, 282(29), 20799-803.

Nassoury N. et al., The cellular trafficking of the secretory proprotein convertase PCSK9 and its dependence on the LDLR. Traffic, 2007, 8, 718-732.

Nour N. et al., Structure-Function analysis of the prosegment of the proprotein convertase PC5A. J. Bio. Chem., 2003, 278(5), 2886-95.

Poirier S. et al., The proprotein convertase PCSK9 induces the degradation of low density lipoprotein receptor (LDLR) and its closest family members VLDLR and ApoER2. J. Biol. Chem., 2008, 283(4), 2363-72.

Rashid S. et al., Decreased plasma cholesterol and hypersensitivity to statins in mice lacking PCSK9. PNAS, 2005 102(15), 5374-79.

Schadt E.E. et al., Mapping the genetic architecture of gene expression in human liver. PLoS Biol., 2008, 6(5), 1020-32.

Seidah N.G. et al., The secretory proprotein convertase neural apoptosis-regulated convertase 1 (NARC-1): Liver regeneration and neuronal differentiation. PNAS, 2003, 100(3), 928-933.

Seidah N.G. et al., The proprotein convertases are potential targets in the treatment of dyslipidemia. J. Mol. Med., 2007, 85, 685-696.

Seidah N.G. et al., The activation and physiological functions of the proprotein convertases. Int. J. Biochem. Cell Biol., 2008, 40, 1111-25.

Siever D.A. et al., Molecules in focus: Extracellular Annexin II. Int. J. Biochem. Cell Biol., 1997, 29(11), 1219-23.

Willer C.J. et al., Newly identified loci that influence lipid concentrations and risk of coronary artery disease. Nat. Gen., 2008, 40(2), 161-169.

Wood Park S. et al., Post-transcriptional regulation of low density lipoprotein receptor protein by proprotein convertase subtilisin/kexin type 9a in mouse liver. J. Biol. Chem., 2004, 279(48), 50630-638.

Zaid A. et al., Proprotein convertase subtilisin/kexin type 9 (PCSK9): Hepatocyte-specific low-density lipoprotein receptor degradation and critical role in mouse liver regeneration. Hepatology, 2008, 48, 646-654.

Zhang D.-W. et al., Binding of proprotein convertase subtilisin/kexin type 9 to epidermal growth factor-like repeat A of low density lipoprotein receptor decreases receptor recycling and increases degradation. J. Biol. Chem., 2007, 282 (25), 18602-612.

Zhang D.-W. et al., Structural requirements for PCSK9-meidated degradation of the low-density lipoprotein receptor. PNAS, 2008, 105(35), 13045-13050.

Zibouche M. et al., The N-terminal domain of annexin 2 serves as a secondary binding site during membrane bridging. J. Biol. Chem., 2008, 283(32), 22121-127.

Baldwin C. et al., Association of Klotho, Bone Morphogenic Protein 6, and Annexin A2 Poymorphisms with Sickle Cell Osteonecrosis. Blood, 2005, 106(1), 372-375.

Ishii H. et al., Recombinant Annexin II Modulated Impaired Fibrinolytic Activity in Vitro and in Rat Carotid Artery. Circ. Res., 2001, 89(12), 1240-1454.

Smart E.J. et al., Annexin-2-Caveolin 1 Complex is a Target of Ezetimibe and Regulates Intestinal Cholesterol Transport. Proc. Natl. Acad. Sci., 2004, 101(10), 3450-3455.

\* cited by examiner

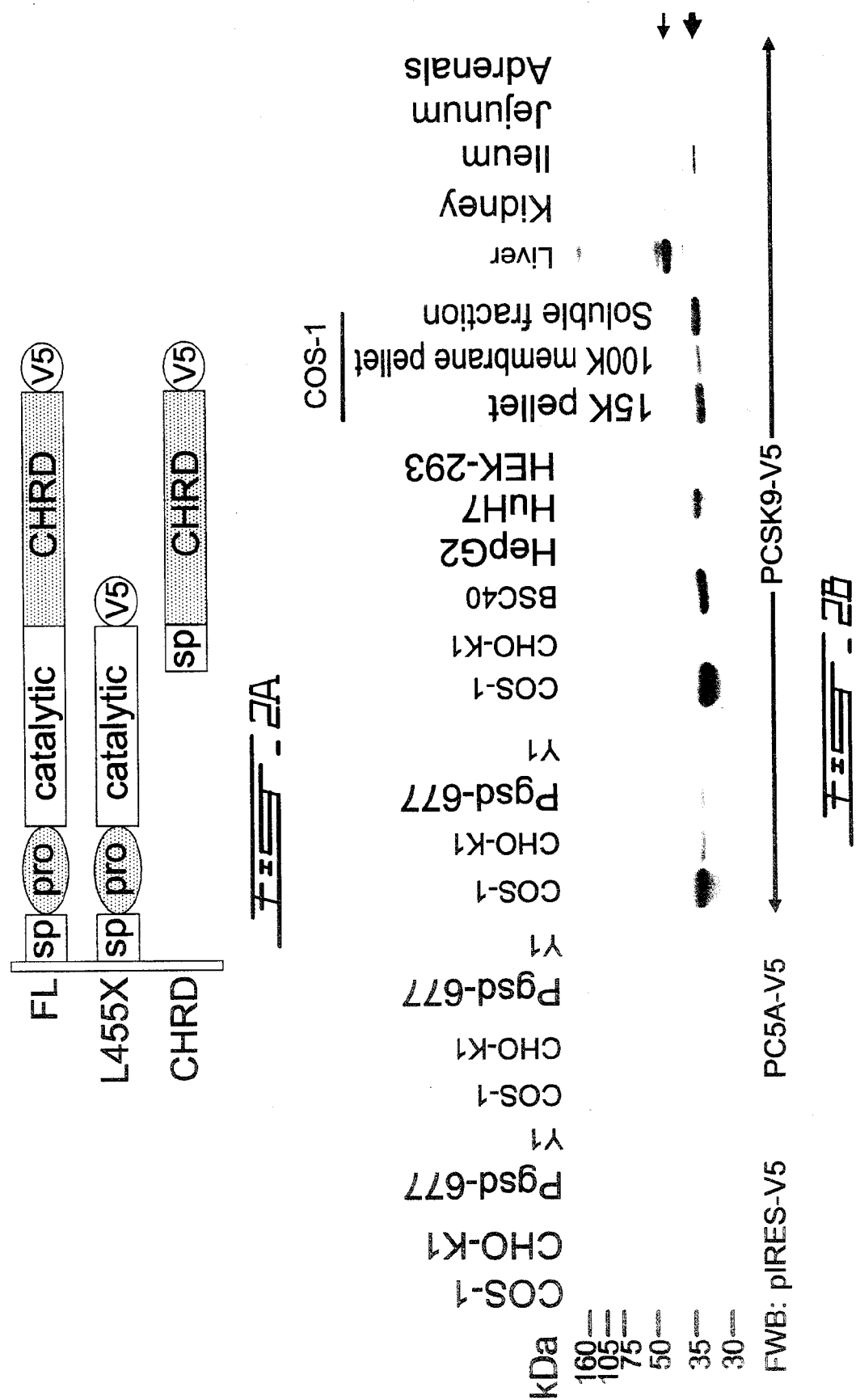

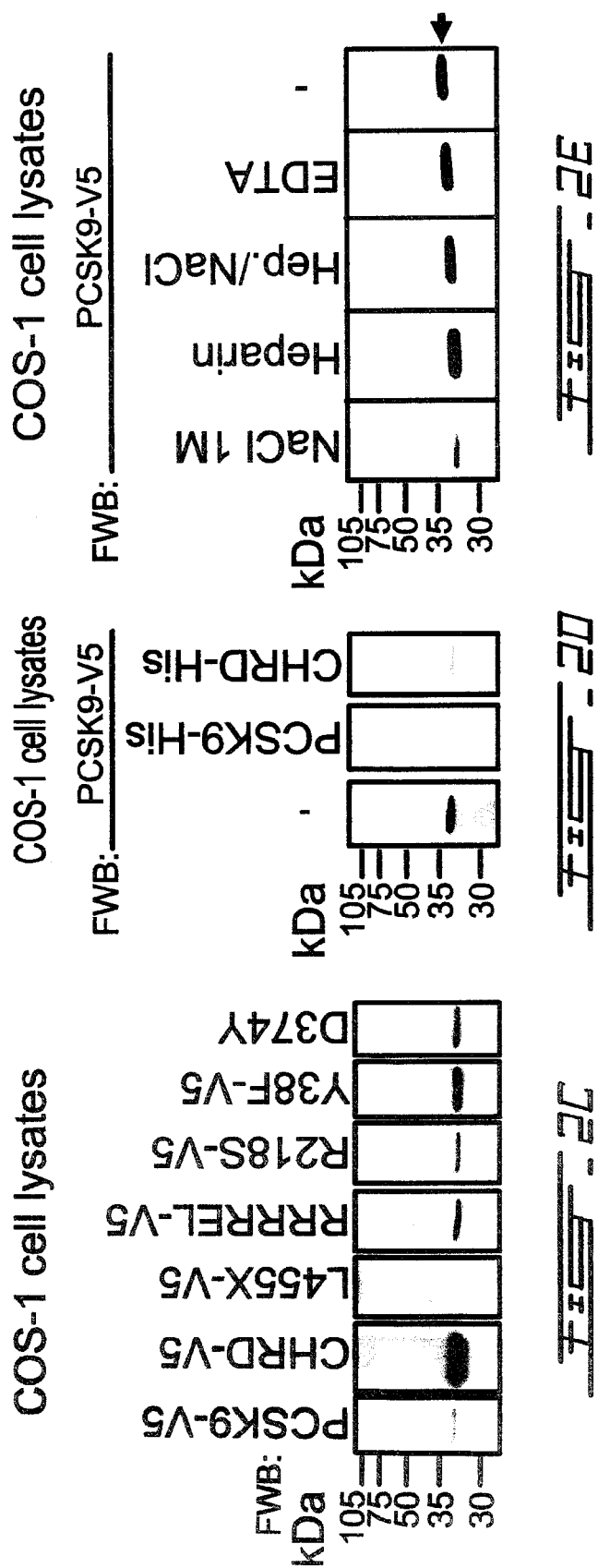

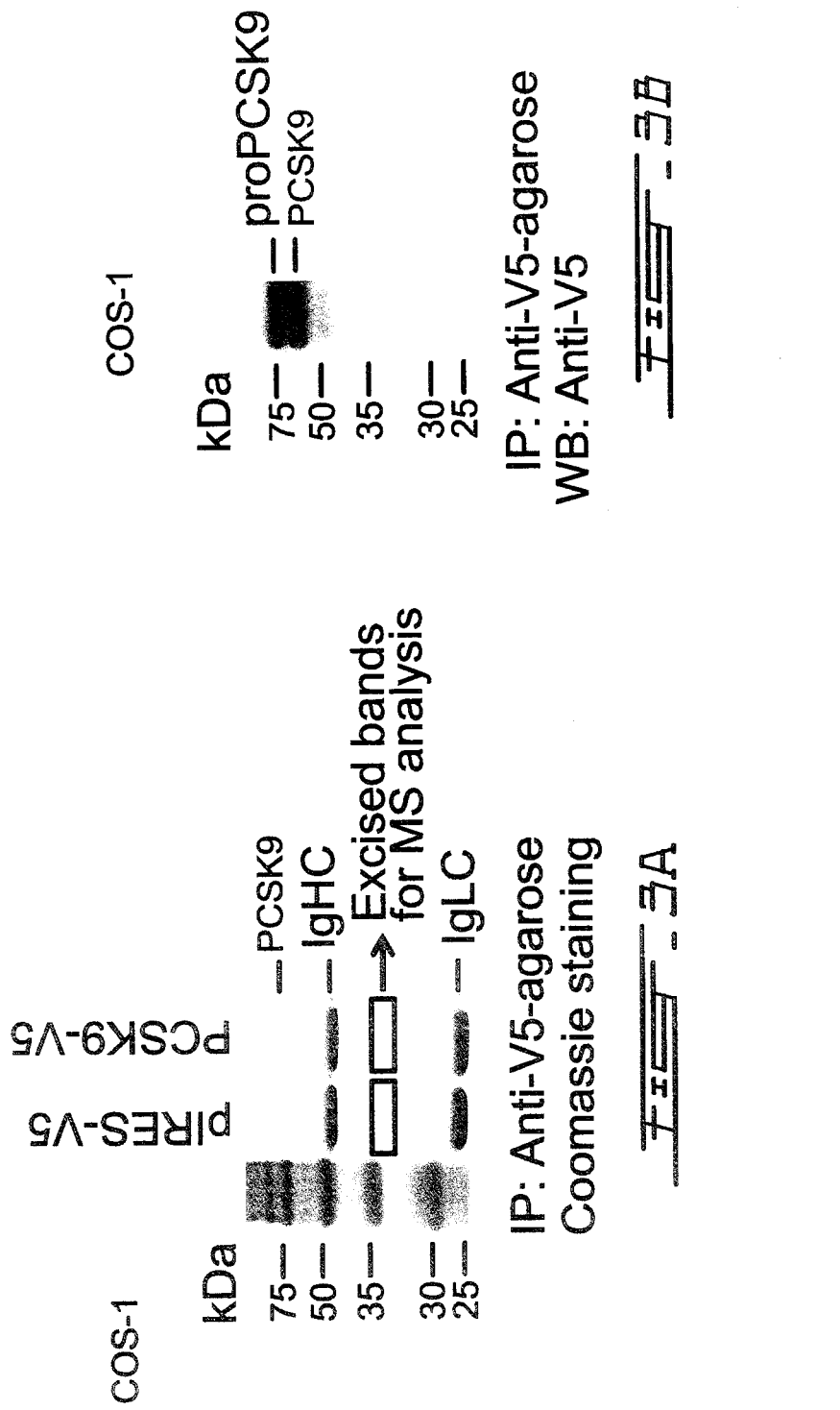

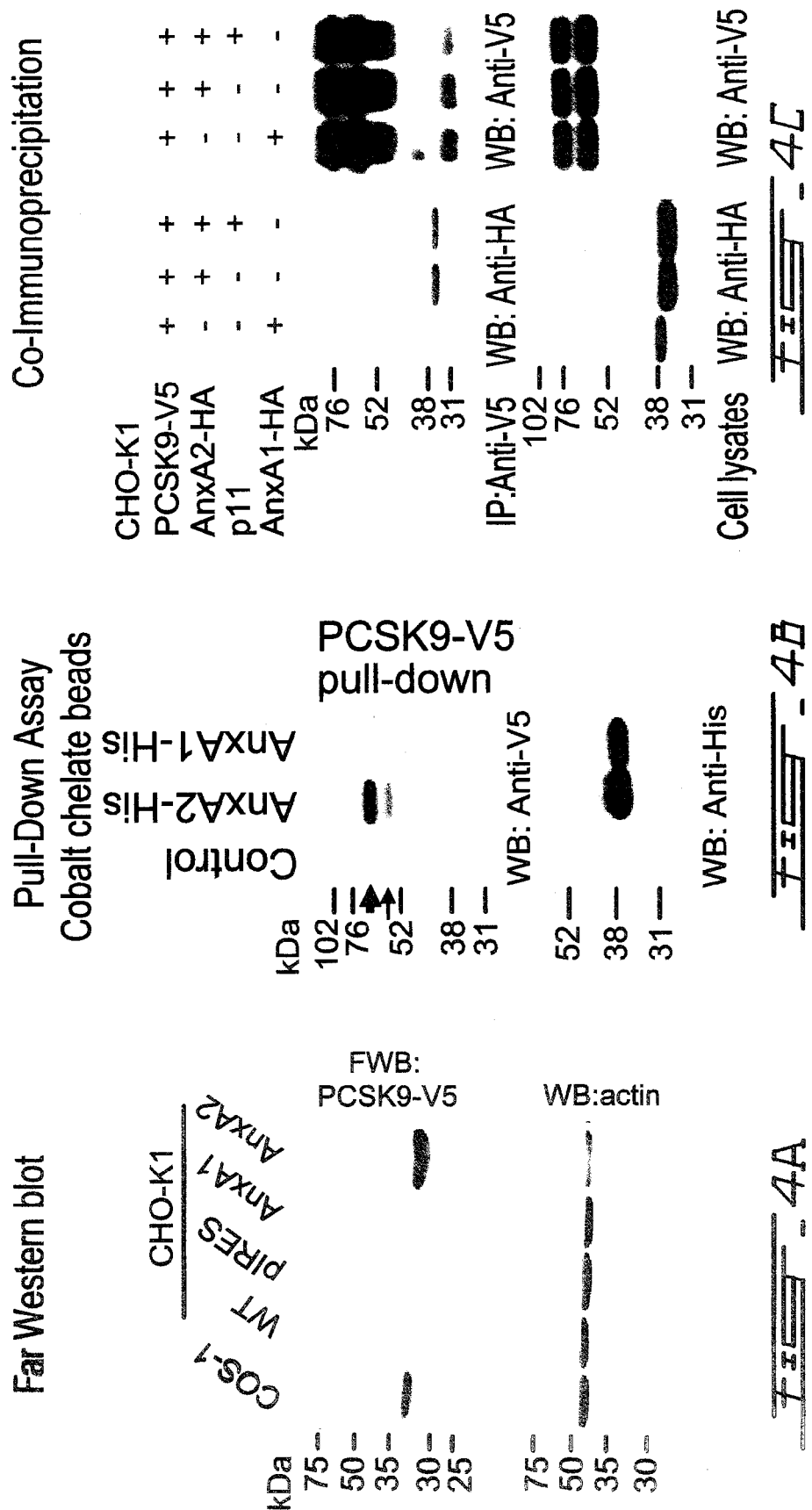

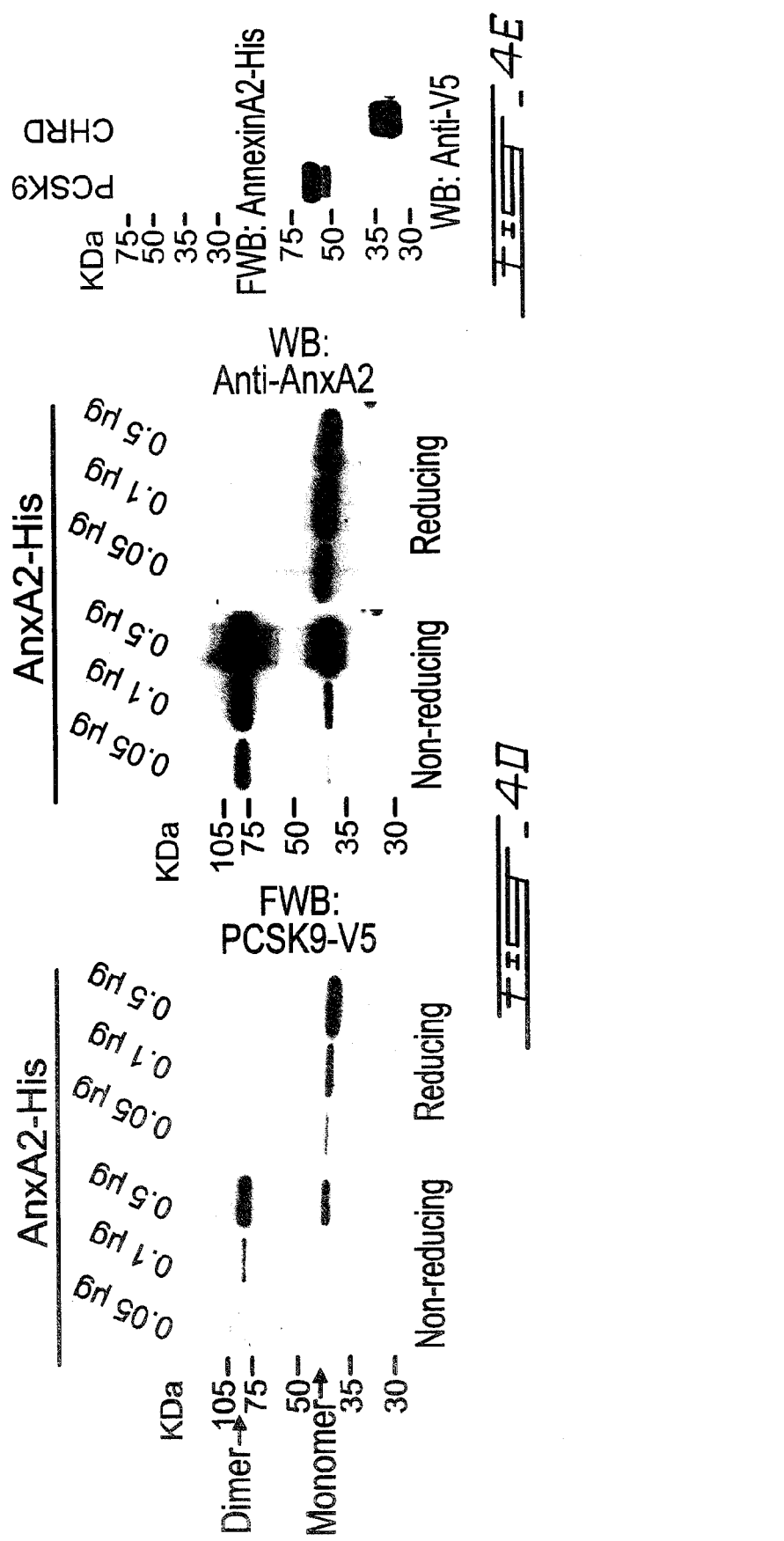

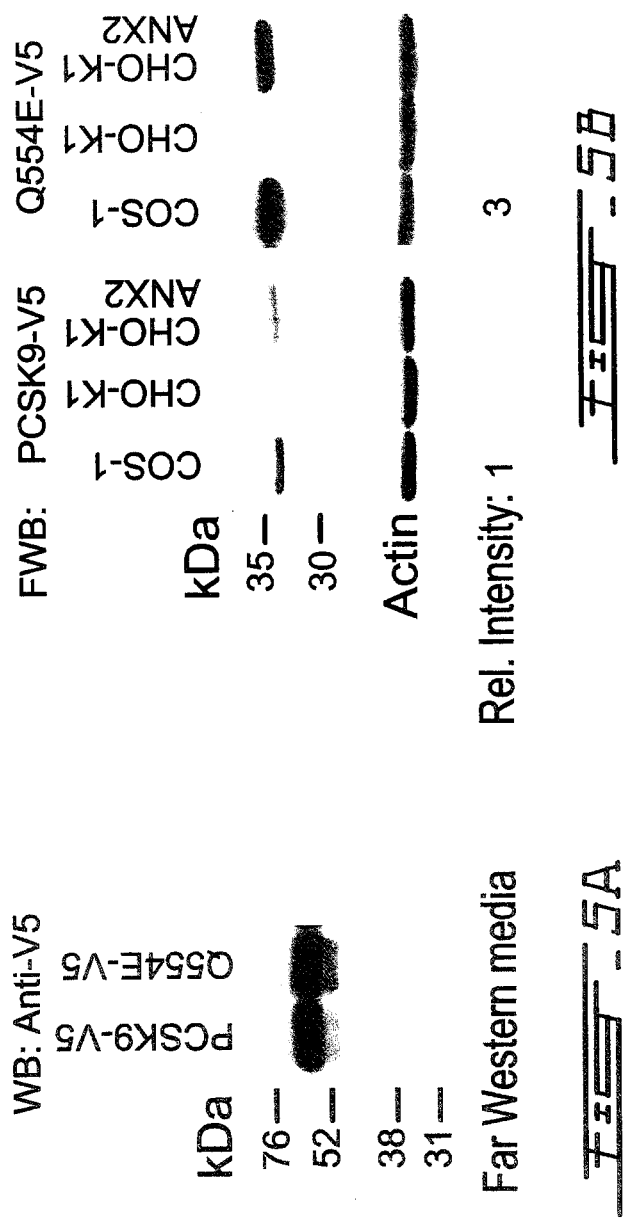

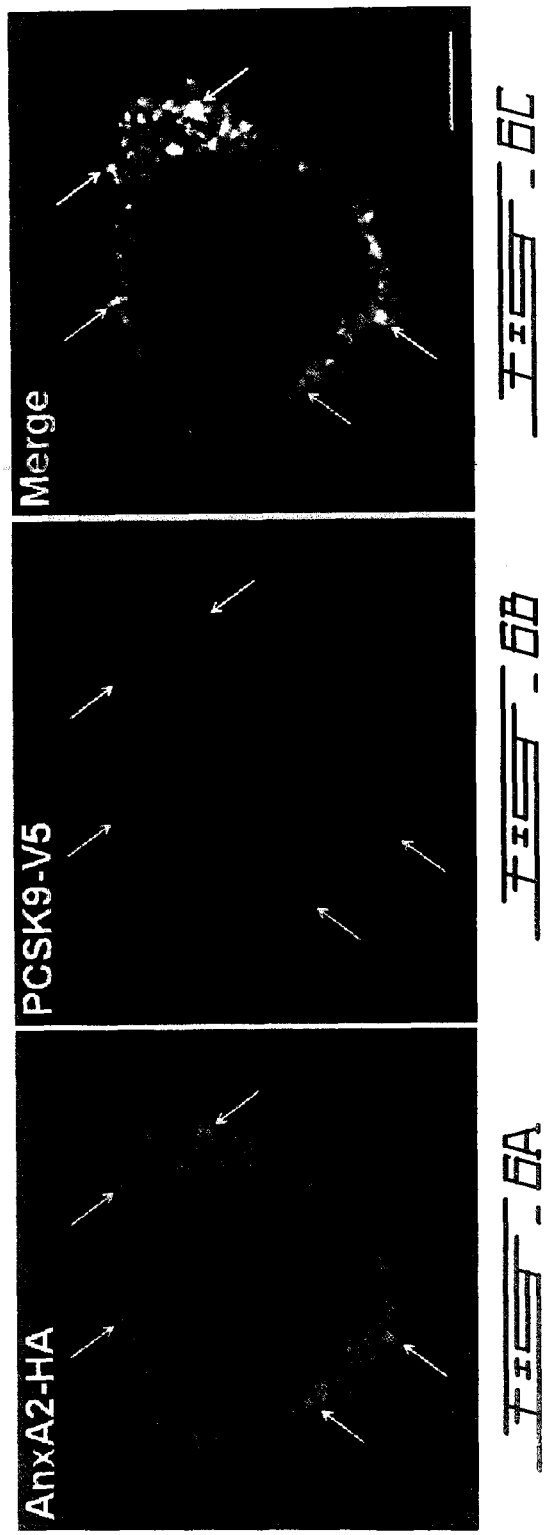

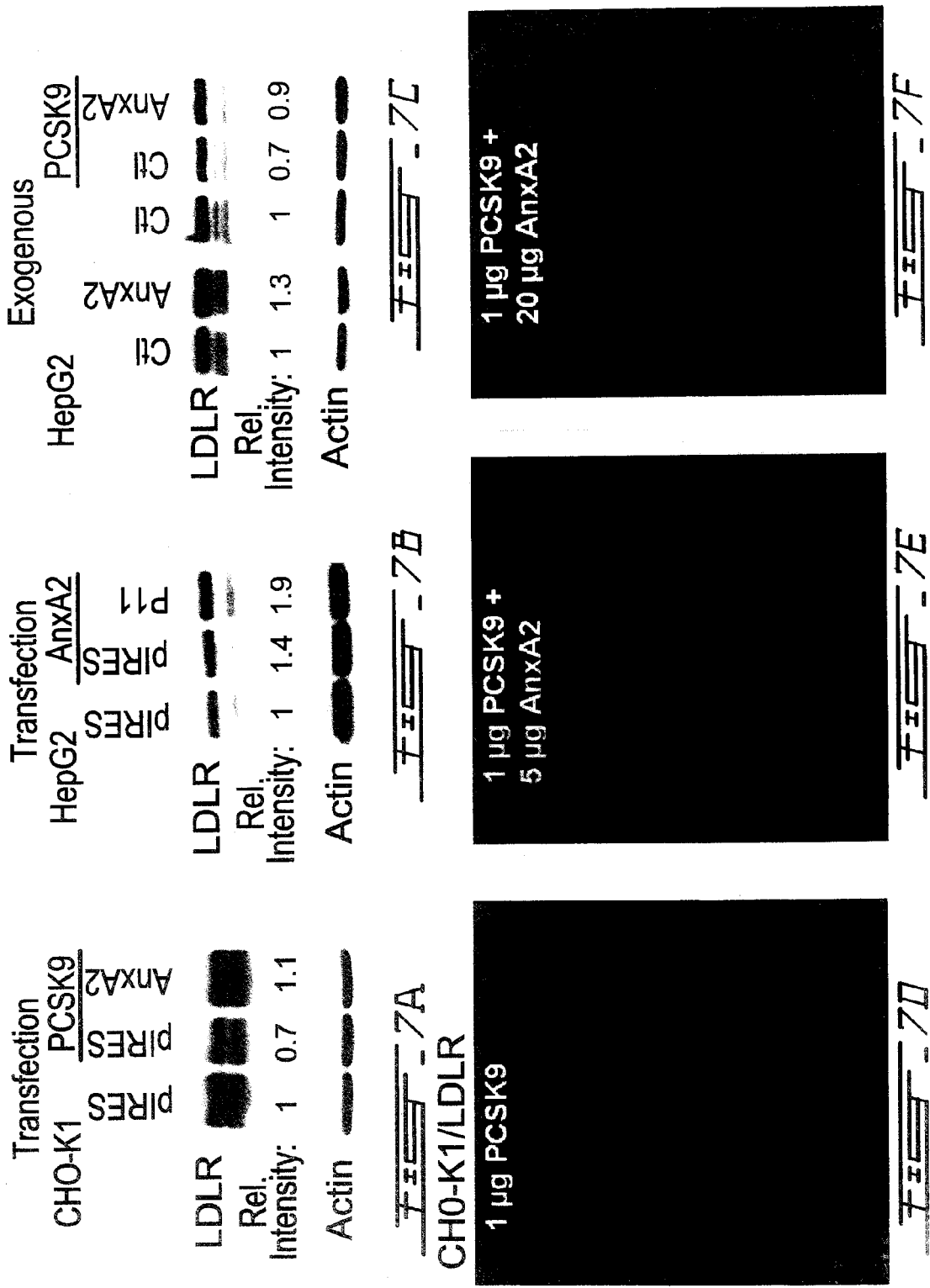

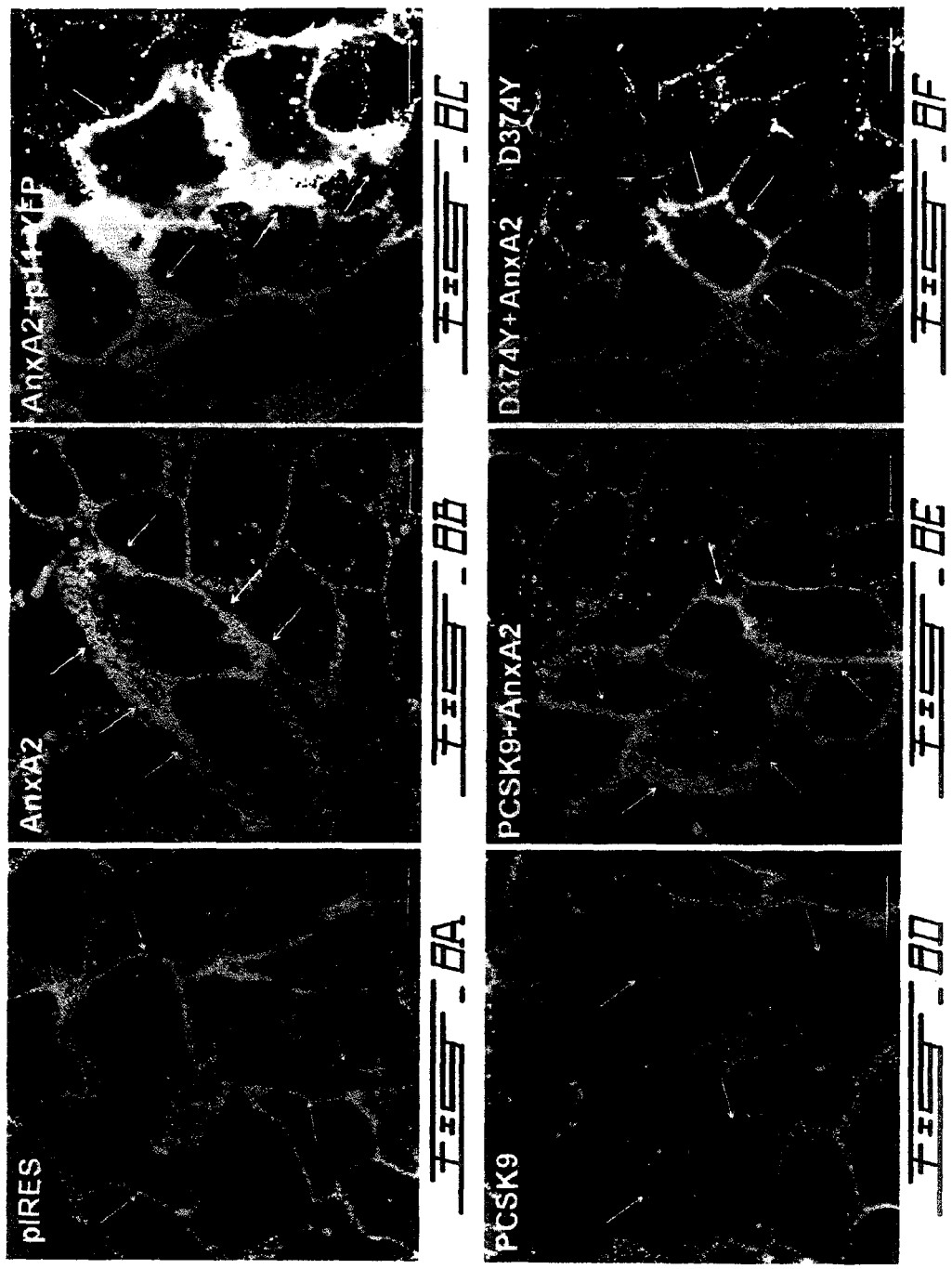

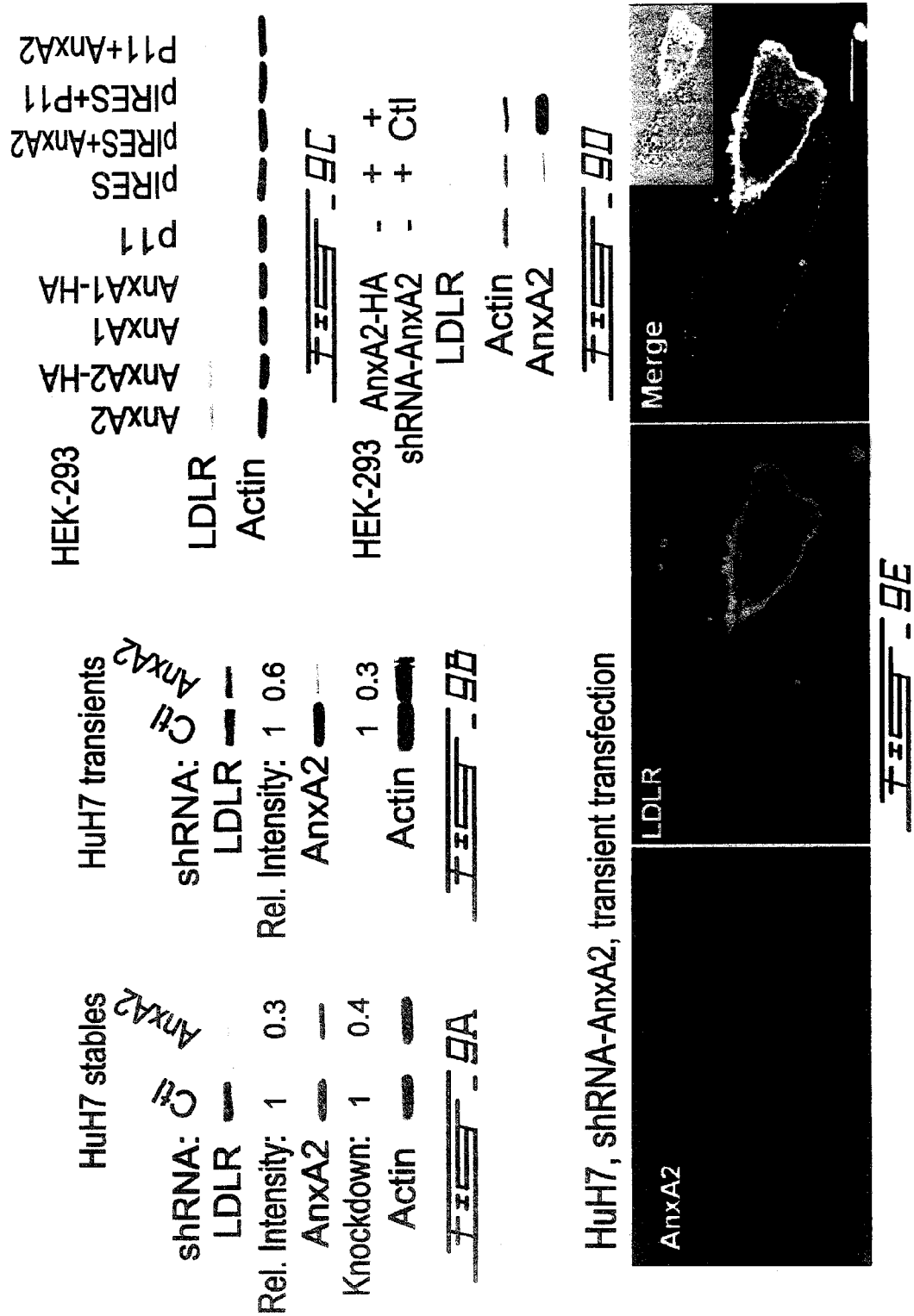

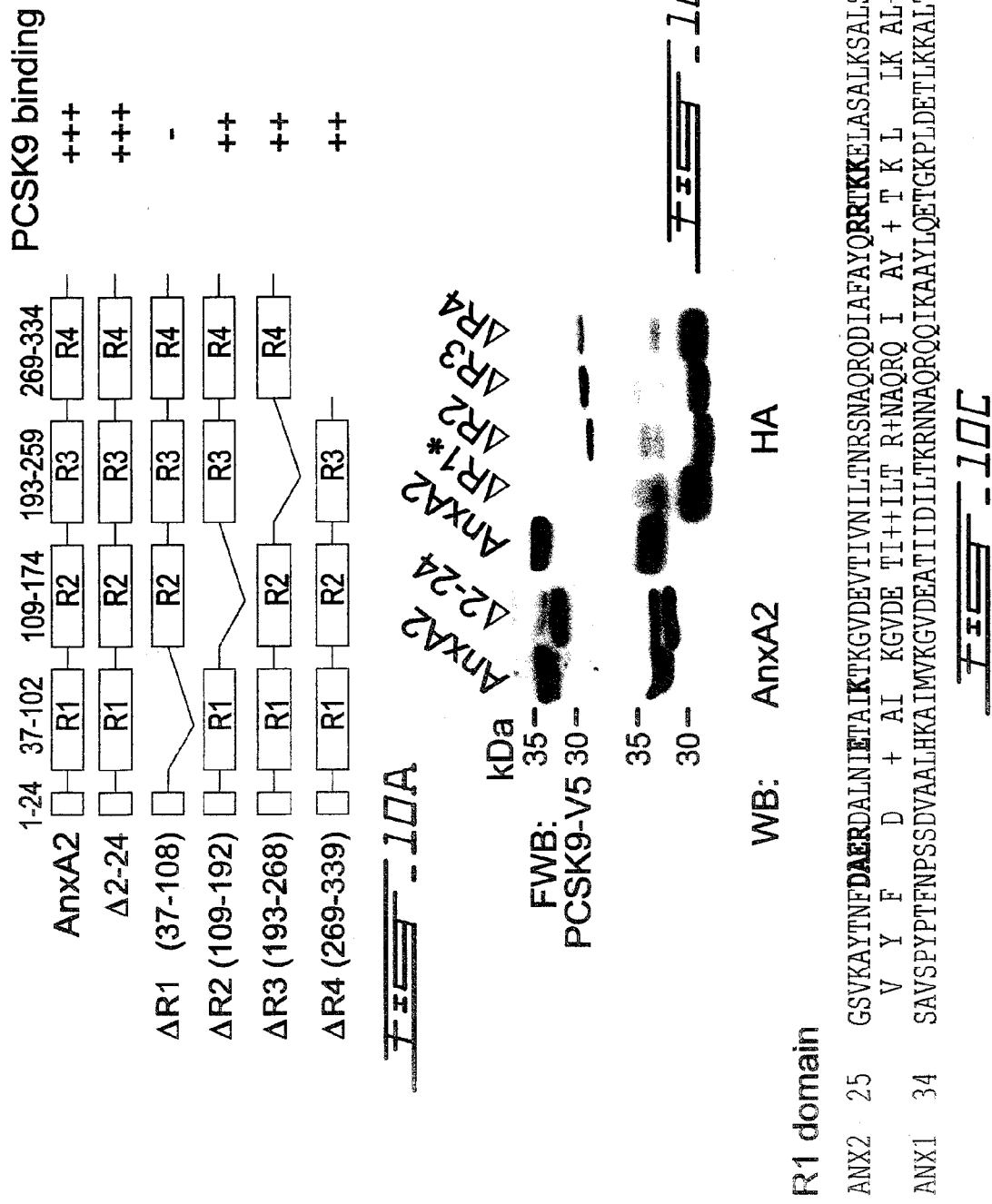

AnxA2
FWB: PCSK9-V5
WB: AnxA2/HA

FL, Δ2-24, ΔAR1(37-108), ΔAR2(109-192)*, ΔAR3(193-268), ΔAR4(269-339), FL, Δ25-36, Δ37-48, Δ49-61, Δ62-75, Δ74-88, FL, 80GKPLD, 77AATAK, 77AATAA*, 49-75 (AnxA1), 77ATAELASALA

AnxA1>AnxA2

AnxA2
FWB: PCSK9-V5
WB: HA

FL, 25-27, 28-30, 31-33, 34-36, 37-39, 40-42, 43-45, 46-48, FL, 49-61, 62-75, 49-75, FL, K28S+D34N+E36S, R37S+E43H+K47M, FL, Δ82-88, Δ89-101, Δ102-108

25-36 ↓          37-48          49-61          62-75          Δ82-88          Δ89-101          Δ102-108

ANX2  25  GSVKAYTNFDAERDALNIETAIKTKGVDEVTVNILTNRSNAQRQDIAFAYQRRTKELASALKSALSGHLETVILGLLKTPAQ  108
           D + AI KGVDE TI++ILT R+NAQRQ I AY + T K L   LK AL+GHLE V+L LLKTPAQ
ANX1  34  SAVSPYPTFNPSSDVAALHKAIMVKGVDEATIIDILKRNNAQRQQIKAAYLQETGKPLDETLKKALTGHLEEVLALLKTPAQ  117

SP-³⁰YTNFDAERDALNIETAIKTKGVDEVTIVNILTNRSNAQRQDIA
FAYQRRTKKELASALKSALSGHLETVILGLLKTPAQ¹⁰⁸-HA

| Human cell lines | ANXA2 /10⁶ S14 | PCSK9 /10⁶ S14 |
|---|---|---|
| Huvec | 1560000 | 45 |
| A549 | 806500 | 954 |
| HeLa | 758250 | 12483 |
| HT-29 | 597500 | 1330 |
| U87 | 381000 | N/A |
| HuH7 | 355000 | 50281 |
| Hela VII 59 | 330000 | N/A |
| CaCo2 | 306500 | 42651 |
| LoVo-C5 | 269000 | 17708 |
| A431 | 222500 | 24794 |
| BON-1 | 193000 | 23950 |
| HepG2 | 172000 | 76828 |
| Ben | 168000 | 579 |
| HT-1080 | 104500 | 22 |
| MCF7 | 90500 | 194 |
| SW13 | 81500 | N/A |
| LoVo | 76000 | 4400 |
| HEK293 | 70500 | 79 |
| SKNM | 20250 | 2535 |
| JurkatF | 11100 | 1 |
| H295R | 6900 | N/A |

FIG. 14

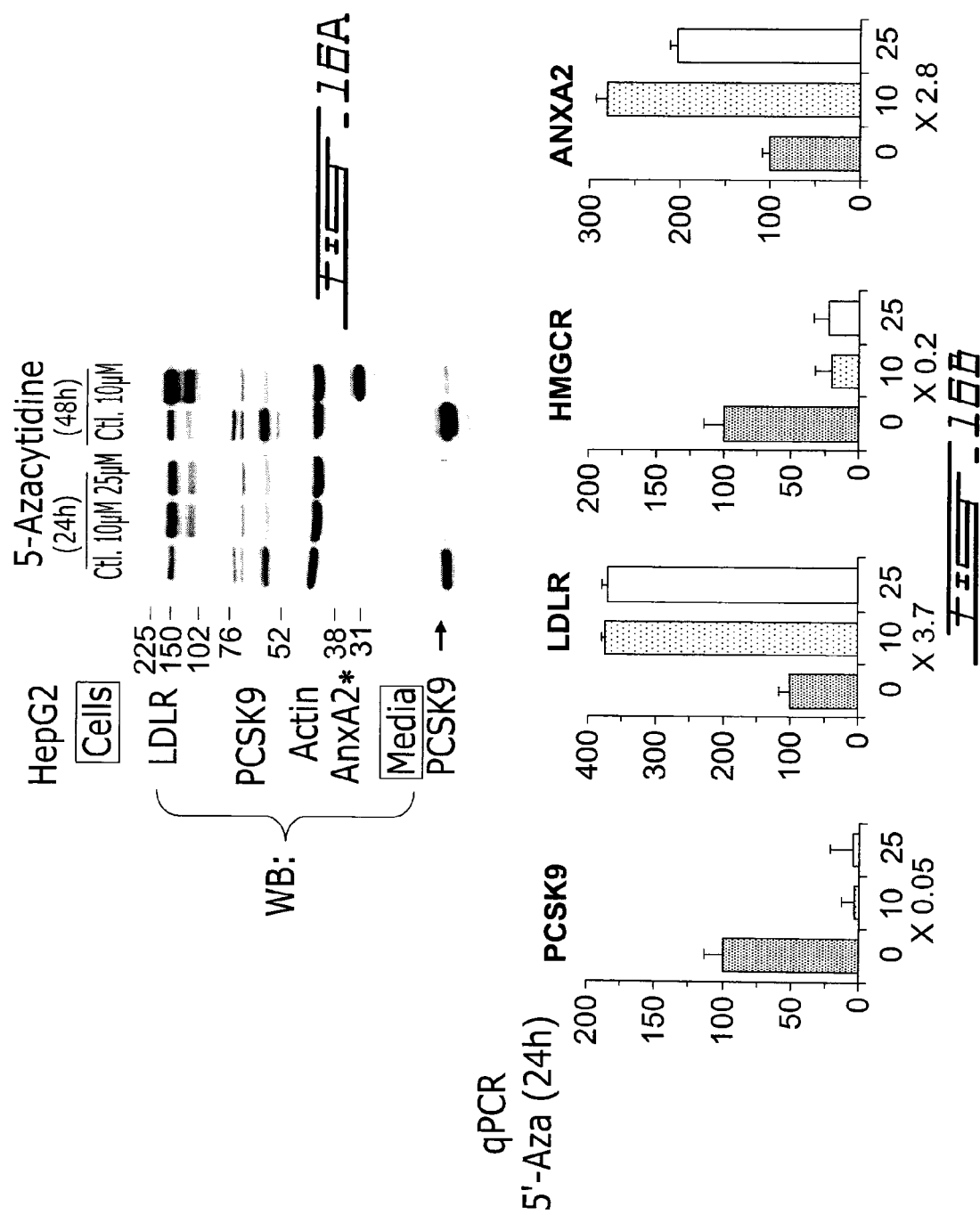

NM_001002857.1→NP_001002857.1 annexin A2 isoform 2
Nucleotide Sequence (1020 nt):
ATGTCTACTGTTCACGAAATCCTGTGCAAGCTCAGCTTGGAGGGTGATCACTCTACACCCCCAAGTGCAT
ATGGGTCTGTCAAAGCCTATACTAACTTTGATGCTGAGCGGGATGCTTTGAACATTGAAACAGCCATCAA
GACCAAAGGTGTGGATGAGGTCACCATTGTCAACATTTTGACCAACCGCAGCAATGCACAGAGACAGGAT
ATTGCCTTCGCCTACCAGAGAAGGACCAAAAAGGAACTTGCATCAGCACTGAAGTCAGCCTTATCTGGCC
ACCTGGAGACGGTGATTTTGGGCCTATTGAAGACACCTGCTCAGTATGACGCTTCTGAGCTAAAAGCTTC
CATGAAGGGGCTGGGAACCGACGAGGACTCTCTCATTGAGATCATCTGCTCCAGAACCAACCAGGAGCTG
CAGGAAATTAACAGAGTCTACAAGGAAATGTACAAGACTGATCTGGAGAAGGACATTATTTCGGACACAT
CTGGTGACTTCCGCAAGCTGATGGTTGCCCTGGCAAAGGGTAGAAGAGCAGAGGATGGCTCTGTCATTGA
TTATGAACTGATTGACCAAGATGCTCGGGATCTCTATGACGCTGGAGTGAAGAGGAAAGGAACTGATGTT
CCCAAGTGGATCAGCATCATGACCGAGCGGAGCGTGCCCCACCTCCAGAAAGTATTTGATAGGTACAAGA
GTTACAGCCCTTATGACATGTTGGAAAGCATCAGGAAAGAGGTTAAAGGAGACCTGGAAAATGCTTTCCT
GAACCTGGTTCAGTGCATTCAGAACAAGCCCCTGTATTTTGCTGATCGGCTGTATGACTCCATGAAGGGC
AAGGGGACGCGAGATAAGGTCCTGATCAGAATCATGGTCTCCCGCAGTGAAGTGGACATGTTGAAAATTA
GGTCTGAATTCAAGAGAAAGTACGGCAAGTCCCTGTACTATTATATCCAGCAAGACACTAAGGGCGACTA
CCAGAAAGCGCTGCTGTACCTGTGTGGTGGAGATGACTGA Amino acid sequence (339 aa):
MSTVHEILCKLSLEGDHSTPPSAYGSVKAYTNFDAERDALNIETAIKTKGVDEVTIVNILTNRSNAQRQD
IAFAYQRRTKKELASALKSALSGHLETVILGLLKTPAQYDASELKASMKGLGTDEDSLIEIICSRTNQEL
QEINRVYKEMYKTDLEKDIISDTSGDFRKLMVALAKGRRAEDGSVIDYELIDQDARDLYDAGVKRKGTDV
PKWISIMTERSVPHLQKVFDRYKSYSPYDMLESIRKEVKGDLENAFLNLVQCIQNKPLYFADRLYDSMKG
KGTRDKVLIRIMVSRSEVDMLKIRSEFKRKYGKSLYYYIQQDTKGDYQKALLYLCGGDD NM_001002858.2→NP_001002858.1 annexin A2 isoform 1
Nucleotide Sequence (1074 nt):
ATGGGCCGCCAGCTAGCGGGGTGTGGAGACGCTGGGAAGAAGGCTTCCTTCAAAATGTCTACTGTTCACG
AAATCCTGTGCAAGCTCAGCTTGGAGGGTGATCACTCTACACCCCCAAGTGCATATGGGTCTGTCAAAGC
CTATACTAACTTTGATGCTGAGCGGGATGCTTTGAACATTGAAACAGCCATCAAGACCAAAGGTGTGGAT
GAGGTCACCATTGTCAACATTTTGACCAACCGCAGCAATGCACAGAGACAGGATATTGCCTTCGCCTACC
AGAGAAGGACCAAAAAGGAACTTGCATCAGCACTGAAGTCAGCCTTATCTGGCCACCTGGAGACGGTGAT
TTTGGGCCTATTGAAGACACCTGCTCAGTATGACGCTTCTGAGCTAAAAGCTTCCATGAAGGGGCTGGGA
ACCGACGAGGACTCTCTCATTGAGATCATCTGCTCCAGAACCAACCAGGAGCTGCAGGAAATTAACAGAG
TCTACAAGGAAATGTACAAGACTGATCTGGAGAAGGACATTATTTCGGACACATCTGGTGACTTCCGCAA
GCTGATGGTTGCCCTGGCAAAGGGTAGAAGAGCAGAGGATGGCTCTGTCATTGATTATGAACTGATTGAC
CAAGATGCTCGGGATCTCTATGACGCTGGAGTGAAGAGGAAAGGAACTGATGTTCCCAAGTGGATCAGCA
TCATGACCGAGCGGAGCGTGCCCCACCTCCAGAAAGTATTTGATAGGTACAAGAGTTACAGCCCTTATGA
CATGTTGGAAAGCATCAGGAAAGAGGTTAAAGGAGACCTGGAAAATGCTTTCCTGAACCTGGTTCAGTGC
ATTCAGAACAAGCCCCTGTATTTTGCTGATCGGCTGTATGACTCCATGAAGGGCAAGGGGACGCGAGATA
AGGTCCTGATCAGAATCATGGTCTCCCGCAGTGAAGTGGACATGTTGAAAATTAGGTCTGAATTCAAGAG
AAAGTACGGCAAGTCCCTGTACTATTATATCCAGCAAGACACTAAGGGCGACTACCAGAAAGCGCTGCTG
TACCTGTGTGGTGGAGATGACTGA Amino acid sequence (357 aa):
MGRQLAGCGDAGKKASFKMSTVHEILCKLSLEGDHSTPPSAYGSVKAYTNFDAERDALNIETAIKTKGVD
EVTIVNILTNRSNAQRQDIAFAYQRRTKKELASALKSALSGHLETVILGLLKTPAQYDASELKASMKGLG
TDEDSLIEIICSRTNQELQEINRVYKEMYKTDLEKDIISDTSGDFRKLMVALAKGRRAEDGSVIDYELID
QDARDLYDAGVKRKGTDVPKWISIMTERSVPHLQKVFDRYKSYSPYDMLESIRKEVKGDLENAFLNLVQC
IQNKPLYFADRLYDSMKGKGTRDKVLIRIMVSRSEVDMLKIRSEFKRKYGKSLYYYIQQDTKGDYQKALL
YLCGGDD

SEQUENCE LISTING

<160> NUMBER OF SEQ ID NOS: 119

<210> SEQ ID NO 1
<211> LENGTH: 357
<212> TYPE: PRT
<213> ORGANISM: HOMO SAPIENS

<400> SEQUENCE: 1

Met Gly Arg Gln Leu Ala Gly Cys Gly Asp Ala Gly Lys Lys Ala Ser
1               5                   10                  15

Phe Lys Met Ser Thr Val His Glu Ile Leu Cys Lys Leu Ser Leu Glu
            20                  25                  30

Gly Asp His Ser Thr Pro Pro Ser Ala Tyr Gly Ser Val Lys Ala Tyr
        35                  40                  45

Thr Asn Phe Asp Ala Glu Arg Asp Ala Leu Asn Ile Glu Thr Ala Ile
    50                  55                  60

Lys Thr Lys Gly Val Asp Glu Val Thr Ile Val Asn Ile Leu Thr Asn
65                  70                  75                  80

Arg Ser Asn Ala Gln Arg Gln Asp Ile Ala Phe Ala Tyr Gln Arg Arg
                85                  90                  95

Thr Lys Lys Glu Leu Ala Ser Ala Leu Lys Ser Ala Leu Ser Gly His
            100                 105                 110

Leu Glu Thr Val Ile Leu Gly Leu Leu Lys Thr Pro Ala Gln Tyr Asp
        115                 120                 125

Ala Ser Glu Leu Lys Ala Ser Met Lys Gly Leu Gly Thr Asp Glu Asp
    130                 135                 140

Ser Leu Ile Glu Ile Ile Cys Ser Arg Thr Asn Gln Glu Leu Gln Glu
145                 150                 155                 160

Ile Asn Arg Val Tyr Lys Glu Met Tyr Lys Thr Asp Leu Glu Lys Asp
                165                 170                 175

Ile Ile Ser Asp Thr Ser Gly Asp Phe Arg Lys Leu Met Val Ala Leu
            180                 185                 190

Ala Lys Gly Arg Arg Ala Glu Asp Gly Ser Val Ile Asp Tyr Glu Leu
        195                 200                 205

Ile Asp Gln Asp Ala Arg Asp Leu Tyr Asp Ala Gly Val Lys Arg Lys
    210                 215                 220

Gly Thr Asp Val Pro Lys Trp Ile Ser Ile Met Thr Glu Arg Ser Val
225                 230                 235                 240

Pro His Leu Gln Lys Val Phe Asp Arg Tyr Lys Ser Tyr Ser Pro Tyr
                245                 250                 255

Asp Met Leu Glu Ser Ile Arg Lys Glu Val Lys Gly Asp Leu Glu Asn
            260                 265                 270

Ala Phe Leu Asn Leu Val Gln Cys Ile Gln Asn Lys Pro Leu Tyr Phe
        275                 280                 285

Ala Asp Arg Leu Tyr Asp Ser Met Lys Gly Lys Thr Arg Asp Lys
    290                 295                 300

Val Leu Ile Arg Ile Met Val Ser Arg Ser Glu Val Asp Met Leu Lys
305                 310                 315                 320

Ile Arg Ser Glu Phe Lys Arg Lys Tyr Gly Lys Ser Leu Tyr Tyr Tyr
                325                 330                 335

Ile Gln Gln Asp Thr Lys Gly Asp Tyr Gln Lys Ala Leu Leu Tyr Leu
            340                 345                 350

Cys Gly Gly Asp Asp
        355

```
<210> SEQ ID NO 2
<211> LENGTH: 339
<212> TYPE: PRT
<213> ORGANISM: HOMO SAPIENS

<400> SEQUENCE: 2

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 3
<211> LENGTH: 55
<212> TYPE: PRT
<213> ORGANISM: HOMO SAPIENS
```

```
<400> SEQUENCE: 3

Asp Ala Glu Arg Asp Ala Leu Asn Ile Glu Thr Ala Ile Lys Thr Lys
1               5                   10                  15

Gly Val Asp Glu Val Thr Ile Val Asn Ile Leu Thr Asn Arg Ser Asn
            20                  25                  30

Ala Gln Arg Gln Asp Ile Ala Phe Ala Tyr Gln Arg Thr Lys Lys
        35                  40                  45

Glu Leu Ala Ser Ala Leu Lys
    50                  55

<210> SEQ ID NO 4
<211> LENGTH: 64
<212> TYPE: PRT
<213> ORGANISM: HOMO SAPIENS

<400> SEQUENCE: 4

Asp Ala Glu Arg Asp Ala Leu Asn Ile Glu Thr Ala Ile Lys Thr Lys
1               5                   10                  15

Gly Val Asp Glu Val Thr Ile Val Asn Ile Leu Thr Asn Arg Ser Asn
            20                  25                  30

Ala Gln Arg Gln Asp Ile Ala Phe Ala Tyr Gln Arg Thr Lys Lys
        35                  40                  45

Glu Leu Ala Ser Ala Leu Lys Ser Ala Leu Ser Gly His Leu Glu Thr
    50                  55                  60

<210> SEQ ID NO 5
<211> LENGTH: 69
<212> TYPE: PRT
<213> ORGANISM: HOMO SAPIENS

<400> SEQUENCE: 5

Asp Ala Glu Arg Asp Ala Leu Asn Ile Glu Thr Ala Ile Lys Thr Lys
1               5                   10                  15

Gly Val Asp Glu Val Thr Ile Val Asn Ile Leu Thr Asn Arg Ser Asn
            20                  25                  30

Ala Gln Arg Gln Asp Ile Ala Phe Ala Tyr Gln Arg Thr Lys Lys
        35                  40                  45

Glu Leu Ala Ser Ala Leu Lys Ser Ala Leu Ser Gly His Leu Glu Thr
    50                  55                  60

Val Ile Leu Gly Leu
65

<210> SEQ ID NO 6
<211> LENGTH: 74
<212> TYPE: PRT
<213> ORGANISM: HOMO SAPIENS

<400> SEQUENCE: 6

Asp Ala Glu Arg Asp Ala Leu Asn Ile Glu Thr Ala Ile Lys Thr Lys
1               5                   10                  15

Gly Val Asp Glu Val Thr Ile Val Asn Ile Leu Thr Asn Arg Ser Asn
            20                  25                  30

Ala Gln Arg Gln Asp Ile Ala Phe Ala Tyr Gln Arg Thr Lys Lys
        35                  40                  45

Glu Leu Ala Ser Ala Leu Lys Ser Ala Leu Ser Gly His Leu Glu Thr
    50                  55                  60

Val Ile Leu Gly Leu Leu Lys Thr Pro Ala
65                  70
```

```
<210> SEQ ID NO 7
<211> LENGTH: 52
<212> TYPE: PRT
<213> ORGANISM: HOMO SAPIENS

<400> SEQUENCE: 7

Arg Asp Ala Leu Asn Ile Glu Thr Ala Ile Lys Thr Lys Gly Val Asp
1               5                   10                  15

Glu Val Thr Ile Val Asn Ile Leu Thr Asn Arg Ser Asn Ala Gln Arg
            20                  25                  30

Gln Asp Ile Ala Phe Ala Tyr Gln Arg Arg Thr Lys Lys Glu Leu Ala
        35                  40                  45

Ser Ala Leu Lys
    50

<210> SEQ ID NO 8
<211> LENGTH: 61
<212> TYPE: PRT
<213> ORGANISM: HOMO SAPIENS

<400> SEQUENCE: 8

Arg Asp Ala Leu Asn Ile Glu Thr Ala Ile Lys Thr Lys Gly Val Asp
1               5                   10                  15

Glu Val Thr Ile Val Asn Ile Leu Thr Asn Arg Ser Asn Ala Gln Arg
            20                  25                  30

Gln Asp Ile Ala Phe Ala Tyr Gln Arg Arg Thr Lys Lys Glu Leu Ala
        35                  40                  45

Ser Ala Leu Lys Ser Ala Leu Ser Gly His Leu Glu Thr
    50                  55                  60

<210> SEQ ID NO 9
<211> LENGTH: 66
<212> TYPE: PRT
<213> ORGANISM: HOMO SAPIENS

<400> SEQUENCE: 9

Arg Asp Ala Leu Asn Ile Glu Thr Ala Ile Lys Thr Lys Gly Val Asp
1               5                   10                  15

Glu Val Thr Ile Val Asn Ile Leu Thr Asn Arg Ser Asn Ala Gln Arg
            20                  25                  30

Gln Asp Ile Ala Phe Ala Tyr Gln Arg Arg Thr Lys Lys Glu Leu Ala
        35                  40                  45

Ser Ala Leu Lys Ser Ala Leu Ser Gly His Leu Glu Thr Val Ile Leu
    50                  55                  60

Gly Leu
65

<210> SEQ ID NO 10
<211> LENGTH: 71
<212> TYPE: PRT
<213> ORGANISM: HOMO SAPIENS

<400> SEQUENCE: 10

Arg Asp Ala Leu Asn Ile Glu Thr Ala Ile Lys Thr Lys Gly Val Asp
1               5                   10                  15

Glu Val Thr Ile Val Asn Ile Leu Thr Asn Arg Ser Asn Ala Gln Arg
            20                  25                  30

Gln Asp Ile Ala Phe Ala Tyr Gln Arg Arg Thr Lys Lys Glu Leu Ala
        35                  40                  45
```

```
Ser Ala Leu Lys Ser Ala Leu Ser Gly His Leu Glu Thr Val Ile Leu
 50                  55                  60

Gly Leu Leu Lys Thr Pro Ala
 65                  70

<210> SEQ ID NO 11
<211> LENGTH: 64
<212> TYPE: PRT
<213> ORGANISM: HOMO SAPIENS

<400> SEQUENCE: 11

Gly Ser Val Lys Ala Tyr Thr Asn Phe Asp Ala Glu Arg Asp Ala Leu
  1               5                  10                  15

Asn Ile Glu Thr Ala Ile Lys Thr Lys Gly Val Asp Glu Val Thr Ile
                 20                  25                  30

Val Asn Ile Leu Thr Asn Arg Ser Asn Ala Gln Arg Gln Asp Ile Ala
             35                  40                  45

Phe Ala Tyr Gln Arg Arg Thr Lys Lys Glu Leu Ala Ser Ala Leu Lys
 50                  55                  60

<210> SEQ ID NO 12
<211> LENGTH: 73
<212> TYPE: PRT
<213> ORGANISM: HOMO SAPIENS

<400> SEQUENCE: 12

Gly Ser Val Lys Ala Tyr Thr Asn Phe Asp Ala Glu Arg Asp Ala Leu
  1               5                  10                  15

Asn Ile Glu Thr Ala Ile Lys Thr Lys Gly Val Asp Glu Val Thr Ile
                 20                  25                  30

Val Asn Ile Leu Thr Asn Arg Ser Asn Ala Gln Arg Gln Asp Ile Ala
             35                  40                  45

Phe Ala Tyr Gln Arg Arg Thr Lys Lys Glu Leu Ala Ser Ala Leu Lys
 50                  55                  60

Ser Ala Leu Ser Gly His Leu Glu Thr
 65                  70

<210> SEQ ID NO 13
<211> LENGTH: 78
<212> TYPE: PRT
<213> ORGANISM: HOMO SAPIENS

<400> SEQUENCE: 13

Gly Ser Val Lys Ala Tyr Thr Asn Phe Asp Ala Glu Arg Asp Ala Leu
  1               5                  10                  15

Asn Ile Glu Thr Ala Ile Lys Thr Lys Gly Val Asp Glu Val Thr Ile
                 20                  25                  30

Val Asn Ile Leu Thr Asn Arg Ser Asn Ala Gln Arg Gln Asp Ile Ala
             35                  40                  45

Phe Ala Tyr Gln Arg Arg Thr Lys Lys Glu Leu Ala Ser Ala Leu Lys
 50                  55                  60

Ser Ala Leu Ser Gly His Leu Glu Thr Val Ile Leu Gly Leu
 65                  70                  75

<210> SEQ ID NO 14
<211> LENGTH: 83
<212> TYPE: PRT
<213> ORGANISM: HOMO SAPIENS

<400> SEQUENCE: 14
```

```
Gly Ser Val Lys Ala Tyr Thr Asn Phe Asp Ala Glu Arg Asp Ala Leu
1               5                   10                  15

Asn Ile Glu Thr Ala Ile Lys Thr Lys Gly Val Asp Glu Val Thr Ile
            20                  25                  30

Val Asn Ile Leu Thr Asn Arg Ser Asn Ala Gln Arg Gln Asp Ile Ala
        35                  40                  45

Phe Ala Tyr Gln Arg Arg Thr Lys Lys Glu Leu Ala Ser Ala Leu Lys
    50                  55                  60

Ser Ala Leu Ser Gly His Leu Glu Thr Val Ile Leu Gly Leu Leu Lys
65                  70                  75                  80

Thr Pro Ala

<210> SEQ ID NO 15
<211> LENGTH: 59
<212> TYPE: PRT
<213> ORGANISM: HOMO SAPIENS

<400> SEQUENCE: 15

Tyr Thr Asn Phe Asp Ala Glu Arg Asp Ala Leu Asn Ile Glu Thr Ala
1               5                   10                  15

Ile Lys Thr Lys Gly Val Asp Glu Val Thr Ile Val Asn Ile Leu Thr
            20                  25                  30

Asn Arg Ser Asn Ala Gln Arg Gln Asp Ile Ala Phe Ala Tyr Gln Arg
        35                  40                  45

Arg Thr Lys Lys Glu Leu Ala Ser Ala Leu Lys
    50                  55

<210> SEQ ID NO 16
<211> LENGTH: 68
<212> TYPE: PRT
<213> ORGANISM: HOMO SAPIENS

<400> SEQUENCE: 16

Tyr Thr Asn Phe Asp Ala Glu Arg Asp Ala Leu Asn Ile Glu Thr Ala
1               5                   10                  15

Ile Lys Thr Lys Gly Val Asp Glu Val Thr Ile Val Asn Ile Leu Thr
            20                  25                  30

Asn Arg Ser Asn Ala Gln Arg Gln Asp Ile Ala Phe Ala Tyr Gln Arg
        35                  40                  45

Arg Thr Lys Lys Glu Leu Ala Ser Ala Leu Lys Ser Ala Leu Ser Gly
    50                  55                  60

His Leu Glu Thr
65

<210> SEQ ID NO 17
<211> LENGTH: 73
<212> TYPE: PRT
<213> ORGANISM: HOMO SAPIENS

<400> SEQUENCE: 17

Tyr Thr Asn Phe Asp Ala Glu Arg Asp Ala Leu Asn Ile Glu Thr Ala
1               5                   10                  15

Ile Lys Thr Lys Gly Val Asp Glu Val Thr Ile Val Asn Ile Leu Thr
            20                  25                  30

Asn Arg Ser Asn Ala Gln Arg Gln Asp Ile Ala Phe Ala Tyr Gln Arg
        35                  40                  45

Arg Thr Lys Lys Glu Leu Ala Ser Ala Leu Lys Ser Ala Leu Ser Gly
    50                  55                  60
```

```
His Leu Glu Thr Val Ile Leu Gly Leu
 65                  70
```

<210> SEQ ID NO 18
<211> LENGTH: 78
<212> TYPE: PRT
<213> ORGANISM: HOMO SAPIENS

<400> SEQUENCE: 18

```
Tyr Thr Asn Phe Asp Ala Glu Arg Asp Ala Leu Asn Ile Glu Thr Ala
 1               5                  10                  15

Ile Lys Thr Lys Gly Val Asp Glu Val Thr Ile Val Asn Ile Leu Thr
             20                  25                  30

Asn Arg Ser Asn Ala Gln Arg Gln Asp Ile Ala Phe Ala Tyr Gln Arg
         35                  40                  45

Arg Thr Lys Lys Glu Leu Ala Ser Ala Leu Lys Ser Ala Leu Ser Gly
     50                  55                  60

His Leu Glu Thr Val Ile Leu Gly Leu Leu Lys Thr Pro Ala
 65                  70                  75
```

<210> SEQ ID NO 19
<211> LENGTH: 40
<212> TYPE: PRT
<213> ORGANISM: HOMO SAPIENS

<400> SEQUENCE: 19

```
Lys Gly Val Asp Glu Val Thr Ile Val Asn Ile Leu Thr Asn Arg Ser
 1               5                  10                  15

Asn Ala Gln Arg Gln Asp Ile Ala Phe Ala Tyr Gln Arg Arg Thr Lys
             20                  25                  30

Lys Glu Leu Ala Ser Ala Leu Lys
         35                  40
```

<210> SEQ ID NO 20
<211> LENGTH: 49
<212> TYPE: PRT
<213> ORGANISM: HOMO SAPIENS

<400> SEQUENCE: 20

```
Lys Gly Val Asp Glu Val Thr Ile Val Asn Ile Leu Thr Asn Arg Ser
 1               5                  10                  15

Asn Ala Gln Arg Gln Asp Ile Ala Phe Ala Tyr Gln Arg Arg Thr Lys
             20                  25                  30

Lys Glu Leu Ala Ser Ala Leu Lys Ser Ala Leu Ser Gly His Leu Glu
         35                  40                  45

Thr
```

<210> SEQ ID NO 21
<211> LENGTH: 54
<212> TYPE: PRT
<213> ORGANISM: HOMO SAPIENS

<400> SEQUENCE: 21

```
Lys Gly Val Asp Glu Val Thr Ile Val Asn Ile Leu Thr Asn Arg Ser
 1               5                  10                  15

Asn Ala Gln Arg Gln Asp Ile Ala Phe Ala Tyr Gln Arg Arg Thr Lys
             20                  25                  30

Lys Glu Leu Ala Ser Ala Leu Lys Ser Ala Leu Ser Gly His Leu Glu
         35                  40                  45

Thr Val Ile Leu Gly Leu
```

<210> SEQ ID NO 22
<211> LENGTH: 59
<212> TYPE: PRT
<213> ORGANISM: HOMO SAPIENS

<400> SEQUENCE: 22

Lys Gly Val Asp Glu Val Thr Ile Val Asn Ile Leu Thr Asn Arg Ser
1               5                   10                  15

Asn Ala Gln Arg Gln Asp Ile Ala Phe Ala Tyr Gln Arg Arg Thr Lys
            20                  25                  30

Lys Glu Leu Ala Ser Ala Leu Lys Ser Ala Leu Ser Gly His Leu Glu
        35                  40                  45

Thr Val Ile Leu Gly Leu Leu Lys Thr Pro Ala
    50                  55

<210> SEQ ID NO 23
<211> LENGTH: 84
<212> TYPE: PRT
<213> ORGANISM: HOMO SAPIENS

<400> SEQUENCE: 23

Ser Ala Val Ser Pro Tyr Pro Thr Phe Asn Pro Ser Ser Asp Val Ala
1               5                   10                  15

Ala Leu His Lys Ala Ile Met Val Lys Gly Val Asp Glu Ala Thr Ile
            20                  25                  30

Ile Asp Ile Leu Thr Lys Arg Asn Asn Ala Gln Arg Gln Gln Ile Lys
        35                  40                  45

Ala Ala Tyr Leu Gln Glu Thr Gly Lys Pro Leu Asp Glu Thr Leu Lys
    50                  55                  60

Lys Ala Leu Thr Gly His Leu Glu Glu Val Val Leu Ala Leu Leu Lys
65                  70                  75                  80

Thr Pro Ala Gln

<210> SEQ ID NO 24
<211> LENGTH: 1020
<212> TYPE: DNA
<213> ORGANISM: HOMO SAPIENS

<400> SEQUENCE: 24
atgtctactg ttcacgaaat cctgtgcaag ctcagcttgg agggtgatca ctctacaccc      60
ccaagtgcat atgggtctgt caaagcctat actaactttg atgctgagcg ggatgctttg     120
aacattgaaa cagccatcaa gaccaaaggt gtggatgagg tcaccattgt caacattttg     180
accaaccgca gcaatgcaca gagacaggat attgccttcg cctaccagag aaggaccaaa     240
aaggaacttg catcagcact gaagtcagcc ttatctggcc acctggagac ggtgattttg     300
ggcctattga agacacctgc tcagtatgac gcttctgagc taaaagcttc catgaagggg     360
ctgggaaccg acgaggactc tctcattgag atcatctgct ccagaaccaa ccaggagctg     420
caggaaatta cagagtctat caaggaaatg tacaagactg atctggagaa ggacattatt     480
tcggacacat ctggtgactt ccgcaagctg atggttgccc tggcaaaggg tagaagagca     540
gaggatggct ctgtcattga ttatgaactg attgaccaag atgctcggga tctctatgac     600
gctggagtga agaggaaagg aactgatgtt cccaagtgga tcagcatcat gaccgagcgg     660
agcgtgcccc acctccagaa agtatttgat aggtacaaga gttacagccc ttatgacatg     720
ttggaaagca tcaggaaaga ggttaaagga gacctggaaa atgctttcct gaacctggtt     780

```
cagtgcattc agaacaagcc cctgtatttt gctgatcggc tgtatgactc catgaagggc      840
aaggggacgc gagataaggt cctgatcaga atcatggtct cccgcagtga agtggacatg      900
ttgaaaatta ggtctgaatt caagagaaag tacggcaagt ccctgtacta ttatatccag      960
caagacacta agggcgacta ccagaaagcg ctgctgtacc tgtgtggtgg agatgactga     1020
```

<210> SEQ ID NO 25
<211> LENGTH: 1074
<212> TYPE: DNA
<213> ORGANISM: HOMO SAPIENS

<400> SEQUENCE: 25

```
atgggccgcc agctagcggg gtgtggagac gctgggaaga aggcttcctt caaaatgtct       60
actgttcacg aaatcctgtg caagctcagc ttggagggtg atcactctac accccccaagt     120 gcatatgggt ctgtcaaagc ctatactaac tttgatgctg agcgggatgc tttgaacatt      180
gaaacagcca tcaagaccaa aggtgtggat gaggtcacca ttgtcaacat ttgaccaac       240 cgcagcaatg cacagagaca ggatattgcc ttcgcctacc agagaaggac caaaaaggaa      300
cttgcatcag cactgaagtc agccttatct ggccacctgg agacggtgat tttgggccta      360
ttgaagacac ctgctcagta tgacgcttct gagctaaaag cttccatgaa ggggctggga      420
accgacgagg actctctcat tgagatcatc tgctccagaa ccaaccagga gctgcaggaa      480
attaacagag tctacaagga atgtacaag actgatctgg agaaggacat tatttcggac       540
acatctggtg acttccgcaa gctgatggtt gccctggcaa agggtagaag agcagaggat      600
ggctctgtca ttgattatga actgattgac caagatgctc gggatctcta tgacgctgga      660
gtgaagagga aggaactga tgttcccaag tggatcagca tcatgaccga gcggagcgtg       720
ccccacctcc agaaagtatt tgataggtac aagagttaca gcccttatga catgttggaa      780
agcatcagga aagaggttaa aggagacctg gaaaatgctt tcctgaacct ggttcagtgc      840
attcagaaca gcccctgta ttttgctgat cggctgtatg actccatgaa gggcaagggg       900
acgcgagata aggtcctgat cagaatcatg gtctcccgca gtgaagtgga catgttgaaa      960
attaggtctg aattcaagag aaagtacggc aagtccctgt actattatat ccagcaagac     1020
actaagggcg actaccagaa agcgctgctg tacctgtgtg gtggagatga ctga           1074
```

<210> SEQ ID NO 26
<211> LENGTH: 5
<212> TYPE: PRT
<213> ORGANISM: artificial
<220> FEATURE:
<223> OTHER INFORMATION: Artificial sequence

<400> SEQUENCE: 26

Arg Arg Thr Lys Lys
1               5

<210> SEQ ID NO 27
<211> LENGTH: 5
<212> TYPE: PRT
<213> ORGANISM: artificial
<220> FEATURE:
<223> OTHER INFORMATION: Artificial sequence

<400> SEQUENCE: 27

Ala Ala Thr Ala Lys
1               5

```
<210> SEQ ID NO 28
<211> LENGTH: 5
<212> TYPE: PRT
<213> ORGANISM: artificial
<220> FEATURE:
<223> OTHER INFORMATION: Artificial sequence

<400> SEQUENCE: 28

Ala Ala Thr Ala Ala
1               5

<210> SEQ ID NO 29
<211> LENGTH: 12
<212> TYPE: PRT
<213> ORGANISM: artificial
<220> FEATURE:
<223> OTHER INFORMATION: Artificial sequence

<400> SEQUENCE: 29

Arg Arg Thr Lys Lys Glu Leu Ala Ser Ala Leu Lys
1               5                   10

<210> SEQ ID NO 30
<211> LENGTH: 12
<212> TYPE: PRT
<213> ORGANISM: artificial
<220> FEATURE:
<223> OTHER INFORMATION: Artificial sequence

<400> SEQUENCE: 30

Ala Ala Thr Ala Ala Glu Leu Ala Ser Ala Leu Ala
1               5                   10

<210> SEQ ID NO 31
<211> LENGTH: 5
<212> TYPE: PRT
<213> ORGANISM: artificial
<220> FEATURE:
<223> OTHER INFORMATION: Artificial sequence

<400> SEQUENCE: 31

Lys Lys Glu Leu Ala
1               5

<210> SEQ ID NO 32
<211> LENGTH: 5
<212> TYPE: PRT
<213> ORGANISM: artificial
<220> FEATURE:
<223> OTHER INFORMATION: Artificial sequence

<400> SEQUENCE: 32

Gly Lys Pro Leu Asp
1               5

<210> SEQ ID NO 33
<211> LENGTH: 34
<212> TYPE: DNA
<213> ORGANISM: artificial
<220> FEATURE:
<223> OTHER INFORMATION: Artificial sequence

<400> SEQUENCE: 33
cgctagccac catggggtct gtcaaagcct atac                              34

<210> SEQ ID NO 34
<211> LENGTH: 20
<212> TYPE: DNA
```

```
<213> ORGANISM: artificial
<220> FEATURE:
<223> OTHER INFORMATION: Artificial sequence

<400> SEQUENCE: 34
gagcaggtgt cttcaatagg                                              20

<210> SEQ ID NO 35
<211> LENGTH: 31
<212> TYPE: DNA
<213> ORGANISM: artificial
<220> FEATURE:
<223> OTHER INFORMATION: Artificial sequence

<400> SEQUENCE: 35
gatgctgagt atgacgcttc tgagctaaaa g                                 31

<210> SEQ ID NO 36
<211> LENGTH: 35
<212> TYPE: DNA
<213> ORGANISM: artificial
<220> FEATURE:
<223> OTHER INFORMATION: Artificial sequence

<400> SEQUENCE: 36
gaagcgtcat actcagcatc aaagttagta taggc                             35

<210> SEQ ID NO 37
<211> LENGTH: 27
<212> TYPE: DNA
<213> ORGANISM: artificial
<220> FEATURE:
<223> OTHER INFORMATION: Artificial sequence

<400> SEQUENCE: 37
cctgctcagc aagatgctcg ggatctc                                      27

<210> SEQ ID NO 38
<211> LENGTH: 32
<212> TYPE: DNA
<213> ORGANISM: artificial
<220> FEATURE:
<223> OTHER INFORMATION: Artificial sequence

<400> SEQUENCE: 38
cgagcatctt gctgagcagg tgtcttcaat ag                                32

<210> SEQ ID NO 39
<211> LENGTH: 40
<212> TYPE: DNA
<213> ORGANISM: artificial
<220> FEATURE:
<223> OTHER INFORMATION: Artificial sequence

<400> SEQUENCE: 39
gattatgaac tgattgacta ttttgctgat cggctgtatg                        40

<210> SEQ ID NO 40
<211> LENGTH: 34
<212> TYPE: DNA
<213> ORGANISM: artificial
<220> FEATURE:
<223> OTHER INFORMATION: Artificial sequence

<400> SEQUENCE: 40
gcaaaatagt caatcagttc ataatcaatg acag                              34
```

-continued

```
<210> SEQ ID NO 41
<211> LENGTH: 26
<212> TYPE: DNA
<213> ORGANISM: artificial
<220> FEATURE:
<223> OTHER INFORMATION: Artificial sequence

<400> SEQUENCE: 41
gcccctgacc ggttacccat acgatg                                          26

<210> SEQ ID NO 42
<211> LENGTH: 34
<212> TYPE: DNA
<213> ORGANISM: artificial
<220> FEATURE:
<223> OTHER INFORMATION: Artificial sequence

<400> SEQUENCE: 42
gtatgggtaa ccggtcaggg gcttgttctg aatg                                 34

<210> SEQ ID NO 43
<211> LENGTH: 35
<212> TYPE: DNA
<213> ORGANISM: artificial
<220> FEATURE:
<223> OTHER INFORMATION: Artificial sequence

<400> SEQUENCE: 43
ccaagtgcat atcgggatgc tttgaacatt gaaac                                35

<210> SEQ ID NO 44
<211> LENGTH: 25
<212> TYPE: DNA
<213> ORGANISM: artificial
<220> FEATURE:
<223> OTHER INFORMATION: Artificial sequence

<400> SEQUENCE: 44
catcccgata tgcacttggg ggtgt                                           25

<210> SEQ ID NO 45
<211> LENGTH: 30
<212> TYPE: DNA
<213> ORGANISM: artificial
<220> FEATURE:
<223> OTHER INFORMATION: Artificial sequence

<400> SEQUENCE: 45
gatgctgagc agagacagga tattgccttc                                      30

<210> SEQ ID NO 46
<211> LENGTH: 34
<212> TYPE: DNA
<213> ORGANISM: artificial
<220> FEATURE:
<223> OTHER INFORMATION: Artificial sequence

<400> SEQUENCE: 46
cctgtctctg ctcagcatca aagttagtat aggc                                 34

<210> SEQ ID NO 47
<211> LENGTH: 24
<212> TYPE: DNA
<213> ORGANISM: artificial
<220> FEATURE:
<223> OTHER INFORMATION: Artificial sequence
```

-continued

```
<400> SEQUENCE: 47
gccttctcag ccttatctgg ccac                                            24

<210> SEQ ID NO 48
<211> LENGTH: 33
<212> TYPE: DNA
<213> ORGANISM: artificial
<220> FEATURE:
<223> OTHER INFORMATION: Artificial sequence

<400> SEQUENCE: 48
ccagataagg ctgagaaggc aatatcctgt ctc                                  33

<210> SEQ ID NO 49
<211> LENGTH: 29
<212> TYPE: DNA
<213> ORGANISM: artificial
<220> FEATURE:
<223> OTHER INFORMATION: Artificial sequence

<400> SEQUENCE: 49
gatgctgaga aggtgtgga tgaggtcac                                        29

<210> SEQ ID NO 50
<211> LENGTH: 34
<212> TYPE: DNA
<213> ORGANISM: artificial
<220> FEATURE:
<223> OTHER INFORMATION: Artificial sequence

<400> SEQUENCE: 50
ccacaccttt ctcagcatca aagttagtat aggc                                 34

<210> SEQ ID NO 51
<211> LENGTH: 26
<212> TYPE: DNA
<213> ORGANISM: artificial
<220> FEATURE:
<223> OTHER INFORMATION: Artificial sequence

<400> SEQUENCE: 51
catcaagacc aaccgcagca atgcac                                          26

<210> SEQ ID NO 52
<211> LENGTH: 30
<212> TYPE: DNA
<213> ORGANISM: artificial
<220> FEATURE:
<223> OTHER INFORMATION: Artificial sequence

<400> SEQUENCE: 52
ctgcggttgg tcttgatggc tgtttcaatg                                      30

<210> SEQ ID NO 53
<211> LENGTH: 36
<212> TYPE: DNA
<213> ORGANISM: artificial
<220> FEATURE:
<223> OTHER INFORMATION: Artificial sequence

<400> SEQUENCE: 53
caacattttg accagaagga ccaaaaagga acttgc                               36

<210> SEQ ID NO 54
<211> LENGTH: 31
<212> TYPE: DNA
```

```
<213> ORGANISM: artificial
<220> FEATURE:
<223> OTHER INFORMATION: Artificial sequence

<400> SEQUENCE: 54
ggtccttctg gtcaaaatgt tgacaatggt g                              31

<210> SEQ ID NO 55
<211> LENGTH: 32
<212> TYPE: DNA
<213> ORGANISM: artificial
<220> FEATURE:
<223> OTHER INFORMATION: Artificial sequence

<400> SEQUENCE: 55
gaaggaccaa aaagtcagcc ttatctggcc ac                             32

<210> SEQ ID NO 56
<211> LENGTH: 34
<212> TYPE: DNA
<213> ORGANISM: artificial
<220> FEATURE:
<223> OTHER INFORMATION: Artificial sequence

<400> SEQUENCE: 56
gataaggctg acttttggt ccttctctgg tagg                            34

<210> SEQ ID NO 57
<211> LENGTH: 32
<212> TYPE: DNA
<213> ORGANISM: artificial
<220> FEATURE:
<223> OTHER INFORMATION: Artificial sequence

<400> SEQUENCE: 57
cagcactgaa gctattgaag acacctgctc ag                             32

<210> SEQ ID NO 58
<211> LENGTH: 32
<212> TYPE: DNA
<213> ORGANISM: artificial
<220> FEATURE:
<223> OTHER INFORMATION: Artificial sequence

<400> SEQUENCE: 58
gtcttcaata gcttcagtgc tgatgcaagt tc                             32

<210> SEQ ID NO 59
<211> LENGTH: 32
<212> TYPE: DNA
<213> ORGANISM: artificial
<220> FEATURE:
<223> OTHER INFORMATION: Artificial sequence

<400> SEQUENCE: 59
gattttgggc tatgacgctt ctgagctaaa ag                             32

<210> SEQ ID NO 60
<211> LENGTH: 29
<212> TYPE: DNA
<213> ORGANISM: artificial
<220> FEATURE:
<223> OTHER INFORMATION: Artificial sequence

<400> SEQUENCE: 60
gaagcgtcat agcccaaaat caccgtctc                                 29
```

-continued

<210> SEQ ID NO 61
<211> LENGTH: 46
<212> TYPE: DNA
<213> ORGANISM: artificial
<220> FEATURE:
<223> OTHER INFORMATION: Artificial sequence

<400> SEQUENCE: 61
tcagcctata ctaactttaa tgcttcgcgg gatgctttga acattg                46

<210> SEQ ID NO 62
<211> LENGTH: 47
<212> TYPE: DNA
<213> ORGANISM: artificial
<220> FEATURE:
<223> OTHER INFORMATION: Artificial sequence

<400> SEQUENCE: 62
cgaagcatta agttagtat aggctgagac agacccatat gcacttg                 47

<210> SEQ ID NO 63
<211> LENGTH: 50
<212> TYPE: DNA
<213> ORGANISM: artificial
<220> FEATURE:
<223> OTHER INFORMATION: Artificial sequence

<400> SEQUENCE: 63
cggatgcttt gaacattcac acagccatca tgaccaaagg tgtggatgag             50

<210> SEQ ID NO 64
<211> LENGTH: 57
<212> TYPE: DNA
<213> ORGANISM: artificial
<220> FEATURE:
<223> OTHER INFORMATION: Artificial sequence

<400> SEQUENCE: 64
catgatggct gtgtgaatgt tcaaagcatc cgactcagca tcaaagttag tataggc     57

<210> SEQ ID NO 65
<211> LENGTH: 33
<212> TYPE: DNA
<213> ORGANISM: artificial
<220> FEATURE:
<223> OTHER INFORMATION: Artificial sequence

<400> SEQUENCE: 65
ggaaagccac ttgattcagc actgaagtca gcc                               33

<210> SEQ ID NO 66
<211> LENGTH: 38
<212> TYPE: DNA
<213> ORGANISM: artificial
<220> FEATURE:
<223> OTHER INFORMATION: Artificial sequence

<400> SEQUENCE: 66
gctgaatcaa gtggctttcc ggtccttctc tggtaggc                          38

<210> SEQ ID NO 67
<211> LENGTH: 33
<212> TYPE: DNA
<213> ORGANISM: artificial
<220> FEATURE:
<223> OTHER INFORMATION: Artificial sequence

```
<400> SEQUENCE: 67
gcagcgaccg caaaggaact tgcatcagca ctg                           33

<210> SEQ ID NO 68
<211> LENGTH: 36
<212> TYPE: DNA
<213> ORGANISM: artificial
<220> FEATURE:
<223> OTHER INFORMATION: Artificial sequence

<400> SEQUENCE: 68
ctttgcggtc gctgcctggt aggcgaaggc aatatc                        36

<210> SEQ ID NO 69
<211> LENGTH: 22
<212> TYPE: DNA
<213> ORGANISM: artificial
<220> FEATURE:
<223> OTHER INFORMATION: Artificial sequence

<400> SEQUENCE: 69
cgaccgcagc ggaacttgca tc                                       22

<210> SEQ ID NO 70
<211> LENGTH: 22
<212> TYPE: DNA
<213> ORGANISM: artificial
<220> FEATURE:
<223> OTHER INFORMATION: Artificial sequence

<400> SEQUENCE: 70
gatgcaagtt ccgctgcggt cg                                       22

<210> SEQ ID NO 71
<211> LENGTH: 25
<212> TYPE: DNA
<213> ORGANISM: artificial
<220> FEATURE:
<223> OTHER INFORMATION: Artificial sequence

<400> SEQUENCE: 71
catcagcact ggcgtcagcc ttatc                                    25

<210> SEQ ID NO 72
<211> LENGTH: 25
<212> TYPE: DNA
<213> ORGANISM: artificial
<220> FEATURE:
<223> OTHER INFORMATION: Artificial sequence

<400> SEQUENCE: 72
gataaggctg acgccagtgc tgatg                                    25

<210> SEQ ID NO 73
<211> LENGTH: 29
<212> TYPE: DNA
<213> ORGANISM: artificial
<220> FEATURE:
<223> OTHER INFORMATION: Artificial sequence

<400> SEQUENCE: 73
ctacaccccc aagtgcatat agcgctgtc                                29

<210> SEQ ID NO 74
<211> LENGTH: 29
<212> TYPE: DNA
```

```
<213> ORGANISM: artificial
<220> FEATURE:
<223> OTHER INFORMATION: Artificial sequence

<400> SEQUENCE: 74
gacagcgcta tatgcacttg ggggtgtag                                    29

<210> SEQ ID NO 75
<211> LENGTH: 28
<212> TYPE: DNA
<213> ORGANISM: artificial
<220> FEATURE:
<223> OTHER INFORMATION: Artificial sequence

<400> SEQUENCE: 75
gggtctgtca gtccctatac taactttg                                     28

<210> SEQ ID NO 76
<211> LENGTH: 28
<212> TYPE: DNA
<213> ORGANISM: artificial
<220> FEATURE:
<223> OTHER INFORMATION: Artificial sequence

<400> SEQUENCE: 76
caaagttagt atagggactg acagaccc                                     28

<210> SEQ ID NO 77
<211> LENGTH: 30
<212> TYPE: DNA
<213> ORGANISM: artificial
<220> FEATURE:
<223> OTHER INFORMATION: Artificial sequence

<400> SEQUENCE: 77
gtcaaagcct atcctacctt tgatgctgag                                   30

<210> SEQ ID NO 78
<211> LENGTH: 30
<212> TYPE: DNA
<213> ORGANISM: artificial
<220> FEATURE:
<223> OTHER INFORMATION: Artificial sequence

<400> SEQUENCE: 78
ctcagcatca aaggtaggat aggctttgac                                   30

<210> SEQ ID NO 79
<211> LENGTH: 34
<212> TYPE: DNA
<213> ORGANISM: artificial
<220> FEATURE:
<223> OTHER INFORMATION: Artificial sequence

<400> SEQUENCE: 79
ctatactaac tttaatccta gtcgggatgc tttg                              34

<210> SEQ ID NO 80
<211> LENGTH: 34
<212> TYPE: DNA
<213> ORGANISM: artificial
<220> FEATURE:
<223> OTHER INFORMATION: Artificial sequence

<400> SEQUENCE: 80
caaagcatcc cgactaggat taaagttagt atag                              34
```

```
<210> SEQ ID NO 81
<211> LENGTH: 32
<212> TYPE: DNA
<213> ORGANISM: artificial
<220> FEATURE:
<223> OTHER INFORMATION: Artificial sequence

<400> SEQUENCE: 81
ctttgatgct gagagcgatg ttttgaacat tg                                    32

<210> SEQ ID NO 82
<211> LENGTH: 32
<212> TYPE: DNA
<213> ORGANISM: artificial
<220> FEATURE:
<223> OTHER INFORMATION: Artificial sequence

<400> SEQUENCE: 82
caatgttcaa aacatcgctc tcagcatcaa ag                                    32

<210> SEQ ID NO 83
<211> LENGTH: 30
<212> TYPE: DNA
<213> ORGANISM: artificial
<220> FEATURE:
<223> OTHER INFORMATION: Artificial sequence

<400> SEQUENCE: 83
cgggatgctg cggcccttga acagccatc                                        30

<210> SEQ ID NO 84
<211> LENGTH: 30
<212> TYPE: DNA
<213> ORGANISM: artificial
<220> FEATURE:
<223> OTHER INFORMATION: Artificial sequence

<400> SEQUENCE: 84
gatggctgtt caagggccg cagcatcccg                                        30

<210> SEQ ID NO 85
<211> LENGTH: 29
<212> TYPE: DNA
<213> ORGANISM: artificial
<220> FEATURE:
<223> OTHER INFORMATION: Artificial sequence

<400> SEQUENCE: 85
ctttgaacat tcacaaagcc atcaagacc                                        29

<210> SEQ ID NO 86
<211> LENGTH: 29
<212> TYPE: DNA
<213> ORGANISM: artificial
<220> FEATURE:
<223> OTHER INFORMATION: Artificial sequence

<400> SEQUENCE: 86
ggtcttgatg gctttgtgaa tgttcaaag                                        29

<210> SEQ ID NO 87
<211> LENGTH: 28
<212> TYPE: DNA
<213> ORGANISM: artificial
<220> FEATURE:
<223> OTHER INFORMATION: Artificial sequence
```

-continued

<400> SEQUENCE: 87
gaaacagcca tcatggtcaa aggtgtgg                                28

<210> SEQ ID NO 88
<211> LENGTH: 28
<212> TYPE: DNA
<213> ORGANISM: artificial
<220> FEATURE:
<223> OTHER INFORMATION: Artificial sequence

<400> SEQUENCE: 88
ccacaccttt gaccatgatg gctgtttc                                28

<210> SEQ ID NO 89
<211> LENGTH: 44
<212> TYPE: DNA
<213> ORGANISM: artificial
<220> FEATURE:
<223> OTHER INFORMATION: Artificial sequence

<400> SEQUENCE: 89
gccaccatta tcgacatttt gaccaaacgc agcaatgcac agag              44

<210> SEQ ID NO 90
<211> LENGTH: 49
<212> TYPE: DNA
<213> ORGANISM: artificial
<220> FEATURE:
<223> OTHER INFORMATION: Artificial sequence

<400> SEQUENCE: 90
tttggtcaaa atgtcgataa tggtggcctc atccacacct ttggtcttg         49

<210> SEQ ID NO 91
<211> LENGTH: 61
<212> TYPE: DNA
<213> ORGANISM: artificial
<220> FEATURE:
<223> OTHER INFORMATION: Artificial sequence

<400> SEQUENCE: 91
aacaatgcac agagacagca aattaaagcc gcctaccaga gaaggaccaa aaaggaactt    60
g                                                            61

<210> SEQ ID NO 92
<211> LENGTH: 58
<212> TYPE: DNA
<213> ORGANISM: artificial
<220> FEATURE:
<223> OTHER INFORMATION: Artificial sequence

<400> SEQUENCE: 92
ctggtaggcg gctttaattt gctgtctctg tgcattgttg cgtttggtca aaatgtcg      58

<210> SEQ ID NO 93
<211> LENGTH: 45
<212> TYPE: DNA
<213> ORGANISM: artificial
<220> FEATURE:
<223> OTHER INFORMATION: Artificial sequence

<400> SEQUENCE: 93
ggccaccatt atcgacattt tgaccaaccg cagcaatgca cagag             45

<210> SEQ ID NO 94

```
<211> LENGTH: 40
<212> TYPE: DNA
<213> ORGANISM: artificial
<220> FEATURE:
<223> OTHER INFORMATION: Artificial sequence

<400> SEQUENCE: 94
caaaatgtcg ataatggtgg cctcatccac acctttggtc                                40

<210> SEQ ID NO 95
<211> LENGTH: 54
<212> TYPE: DNA
<213> ORGANISM: artificial
<220> FEATURE:
<223> OTHER INFORMATION: Artificial sequence

<400> SEQUENCE: 95
aaacgcaaca atgcacagag acagcagatt aaggccgcct accagagaag gacc              54

<210> SEQ ID NO 96
<211> LENGTH: 58
<212> TYPE: DNA
<213> ORGANISM: artificial
<220> FEATURE:
<223> OTHER INFORMATION: Artificial sequence

<400> SEQUENCE: 96
ggccttaatc tgctgtctct gtgcattgtt gcgtttggtc aaaatgttga caatggtg          58

<210> SEQ ID NO 97
<211> LENGTH: 22
<212> TYPE: DNA
<213> ORGANISM: artificial
<220> FEATURE:
<223> OTHER INFORMATION: Artificial sequence

<400> SEQUENCE: 97
gggcggtagg cgtgtacggt gg                                                  22

<210> SEQ ID NO 98
<211> LENGTH: 26
<212> TYPE: DNA
<213> ORGANISM: artificial
<220> FEATURE:
<223> OTHER INFORMATION: Artificial sequence

<400> SEQUENCE: 98
caaagttagt atacgcacgg gcgccc                                              26

<210> SEQ ID NO 99
<211> LENGTH: 32
<212> TYPE: DNA
<213> ORGANISM: artificial
<220> FEATURE:
<223> OTHER INFORMATION: Artificial sequence

<400> SEQUENCE: 99
cgcccgtgcg tatactaact ttgatgctga gc                                       32

<210> SEQ ID NO 100
<211> LENGTH: 33
<212> TYPE: DNA
<213> ORGANISM: artificial
<220> FEATURE:
<223> OTHER INFORMATION: Artificial sequence

<400> SEQUENCE: 100
```

```
gggtaaccgg tctgagcagg tgtcttcaat agg                                    33

<210> SEQ ID NO 101
<211> LENGTH: 23
<212> TYPE: DNA
<213> ORGANISM: artificial
<220> FEATURE:
<223> OTHER INFORMATION: Artificial sequence

<400> SEQUENCE: 101
cattttgacc caacgcagca atg                                               23

<210> SEQ ID NO 102
<211> LENGTH: 23
<212> TYPE: DNA
<213> ORGANISM: artificial
<220> FEATURE:
<223> OTHER INFORMATION: Artificial sequence

<400> SEQUENCE: 102
cattgctgcg ttgggtcaaa atg                                               23

<210> SEQ ID NO 103
<211> LENGTH: 24
<212> TYPE: DNA
<213> ORGANISM: artificial
<220> FEATURE:
<223> OTHER INFORMATION: Artificial sequence

<400> SEQUENCE: 103
ccaaccgcgc caatgcacag agac                                              24

<210> SEQ ID NO 104
<211> LENGTH: 24
<212> TYPE: DNA
<213> ORGANISM: artificial
<220> FEATURE:
<223> OTHER INFORMATION: Artificial sequence

<400> SEQUENCE: 104
gtctctgtgc attgcgcgg ttgg                                               24

<210> SEQ ID NO 105
<211> LENGTH: 29
<212> TYPE: DNA
<213> ORGANISM: artificial
<220> FEATURE:
<223> OTHER INFORMATION: Artificial sequence

<400> SEQUENCE: 105
gcatcagcac tgaagtcagc cttatctgg                                         29

<210> SEQ ID NO 106
<211> LENGTH: 18
<212> TYPE: DNA
<213> ORGANISM: artificial
<220> FEATURE:
<223> OTHER INFORMATION: Artificial sequence

<400> SEQUENCE: 106
atccacgctt cctgctgc                                                     18

<210> SEQ ID NO 107
<211> LENGTH: 18
<212> TYPE: DNA
<213> ORGANISM: artificial
<220> FEATURE:
```

```
<223> OTHER INFORMATION: Artificial sequence

<400> SEQUENCE: 107
cacggtcacc tgctcctg                                                 18

<210> SEQ ID NO 108
<211> LENGTH: 20
<212> TYPE: DNA
<213> ORGANISM: artificial
<220> FEATURE:
<223> OTHER INFORMATION: Artificial sequence

<400> SEQUENCE: 108
aggagacgtg cttgtctgtc                                               20

<210> SEQ ID NO 109
<211> LENGTH: 18
<212> TYPE: DNA
<213> ORGANISM: artificial
<220> FEATURE:
<223> OTHER INFORMATION: Artificial sequence

<400> SEQUENCE: 109
ctgagccgtt gtcgcagt                                                 18

<210> SEQ ID NO 110
<211> LENGTH: 20
<212> TYPE: DNA
<213> ORGANISM: artificial
<220> FEATURE:
<223> OTHER INFORMATION: Artificial sequence

<400> SEQUENCE: 110
gtcacatgat tcacaacagg                                               20

<210> SEQ ID NO 111
<211> LENGTH: 19
<212> TYPE: DNA
<213> ORGANISM: artificial
<220> FEATURE:
<223> OTHER INFORMATION: Artificial sequence

<400> SEQUENCE: 111
gtcctttaga acccaatgc                                                19

<210> SEQ ID NO 112
<211> LENGTH: 20
<212> TYPE: DNA
<213> ORGANISM: artificial
<220> FEATURE:
<223> OTHER INFORMATION: Artificial sequence

<400> SEQUENCE: 112
caagagaaag tacggcaagt                                               20

<210> SEQ ID NO 113
<211> LENGTH: 20
<212> TYPE: DNA
<213> ORGANISM: artificial
<220> FEATURE:
<223> OTHER INFORMATION: Artificial sequence

<400> SEQUENCE: 113
ctttggctta caggagagac                                               20

<210> SEQ ID NO 114
```

```
<211> LENGTH: 21
<212> TYPE: DNA
<213> ORGANISM: artificial
<220> FEATURE:
<223> OTHER INFORMATION: Artificial sequence

<400> SEQUENCE: 114
gattagaatc atggtctctc g                                              21

<210> SEQ ID NO 115
<211> LENGTH: 20
<212> TYPE: DNA
<213> ORGANISM: artificial
<220> FEATURE:
<223> OTHER INFORMATION: Artificial sequence

<400> SEQUENCE: 115
ttagtggaga gcgaagtctc                                                20

<210> SEQ ID NO 116
<211> LENGTH: 22
<212> TYPE: DNA
<213> ORGANISM: artificial
<220> FEATURE:
<223> OTHER INFORMATION: Artificial sequence

<400> SEQUENCE: 116
ggcagaccga gatgaatcct ca                                             22

<210> SEQ ID NO 117
<211> LENGTH: 21
<212> TYPE: DNA
<213> ORGANISM: artificial
<220> FEATURE:
<223> OTHER INFORMATION: Artificial sequence

<400> SEQUENCE: 117
caggtccagg ggtcttggtc c                                              21

<210> SEQ ID NO 118
<211> LENGTH: 21
<212> TYPE: DNA
<213> ORGANISM: artificial
<220> FEATURE:
<223> OTHER INFORMATION: Artificial sequence

<400> SEQUENCE: 118
aggagcgatt tgctggtgtg g                                              21

<210> SEQ ID NO 119
<211> LENGTH: 21
<212> TYPE: DNA
<213> ORGANISM: artificial
<220> FEATURE:
<223> OTHER INFORMATION: Artificial sequence

<400> SEQUENCE: 119
gctaccaggg cctttgagat g                                              21
```

PCSK9 INHIBITORS AND METHODS OF USE THEREOF

CROSS-REFERENCE TO RELATED APPLICATIONS

This application is a National Entry Application of PCT application No. PCT/CA2009/000764 filed on Jun. 1, 2009 and published in English under PCT Article 21(2), which itself claims benefit of U.S. provisional application Ser. No. 61/057,548, filed on May 30, 2008. All documents above are incorporated herein in their entirety by reference.

STATEMENT REGARDING FEDERALLY SPONSORED RESEARCH OR DEVELOPMENT

N.A.

REFERENCE SEQUENCE LISTING

This application contains a Sequence Listing in computer readable form entitled 765-PCT-sequence listing 12810.269_ST25, created Jun. 1, 2009, and having a size of 39 Kb. The computer readable form is incorporated herein by reference in its entirety.

FIELD OF THE INVENTION

The present invention relates to PCSK9 inhibitors and methods of use thereof. More specifically, the present invention is concerned with inhibitors of PCSK9-induced LDLR, VLDLR, ApoER2 or CD81 degradation and methods of use thereof.

BACKGROUND OF THE INVENTION

PCSK9 is the 9th member of a family of secretory subtilisin-like serine proteinases known as the proprotein convertases (PCs)[1-3]. It is now recognized as a major candidate gene for the development of pharmacologically relevant inhibitors or silencers, as it induces an enhanced cellular degradation of the low density lipoprotein receptor (LDLR) in endosomes-lysosomes[4,5]. An increased activity of PCSK9 would thus result in an upregulation of the level of circulating LDL-cholesterol, one of the major causes of dyslipidemias leading to hypercholesterolemia and atherosclerosis. Indeed, its gene represents the third chromosomal locus of dominant familial hypercholesterolemia[6] as was recently reconfirmed in two genetic wide screens[7,8] and a liver specific screen[9]. Both gain and loss of function mutations have been reported for PCSK9 resulting in hyper- and hypo-cholesterolemia, respectively[3]. Indeed, recent data supported this notion, in either knockout mice[10,11] or in transgenic mice overexpressing PCSK9 in liver[11].

PCSK9 is the only PC that is secreted as a catalytically inactive prosegment-PC heterodimer[2,4,12]. Indeed, the enhanced degradation of the LDLR[4,5,13,149-11] in endosomes/lysosomes[4,15] induced by PCSK9 does not seem to require its catalytic activity[12,16]. The same seems to apply to the PCSK9-induced degradation of two other LDLR-family members VLDLR and ApoER2[17]. This intriguing twist in the function of this convertase is supported by the crystal structure of PCSK9, which revealed an extended tight binding complex of the enzyme and its inhibitory prosegment[18]. Indeed, it is this complex that tightly binds the EGF-A repeat of the LDLR[19] with increasing strength at the lower pH of endosomes/lysosomes[18] that likely leads to the degradation of this tripartite complex by resident hydrolases. Thus, although the zymogen propCSK9 is autocatalytically converted into the inactive heterodimer prosegment-PCSK9 in the ER[2,4], so far the only known PCSK9 substrate is itself.

The present description refers to a number of documents, the content of which is herein incorporated by reference in their entirety.

SUMMARY OF THE INVENTION

More specifically, in accordance with an aspect of the present invention, there is provided a method for identifying a compound for preventing or treating a LDLR-associated disease, a VLDLR-associated disease, an ApoER2-associated disease, said method comprising determining whether: a) a level of expression of Annexin A2 nucleic acid or encoded polypeptide; b) a level of Annexin A2 activity; or c) a combination of a) and b), is increased in the presence of a test compound relative to in the absence of said test compound, wherein said increase is indicative that said test compound can be used for preventing or treating a LDLR-associated disease, a VLDLR-associated disease or an ApoER2-associated disease.

In accordance with another aspect of the present invention, there is provided a method for identifying a compound for preventing or treating a CD81-associated disease said method comprising determining whether: a) a level of expression of Annexin A2 nucleic acid or encoded polypeptide; b) a level of Annexin A2 activity; or c) a combination of a) and b), is decreased in the presence of a test compound (e.g., shRNA directed against Anxa2) relative to in the absence of said test compound, wherein said decrease is indicative that said test compound can be used for preventing or treating a CD81-associated disease (e.g., an HCV infection).

AnxA2 binds PCSK9 at a specific binding domain and inhibits PCSK9 activities. It is expected that other compounds binding this specific domain would also prevent or treat PCSK9-associated diseases. n one aspect, the present invention concerns a method of identifying and characterizing a compound specifically targeting the AnxA2 binding domain on PCSK9 for preventing or treating a LDLR-associated disease, a VLDLR-associated disease or an ApoER2-associated disease, said method comprising determining whether a level of PCSK9 activity is decreased in the presence of a test compound specifically targeting the AnxA2 binding domain on PCSK9 relative to in the absence of said test compound, wherein said decrease is indicative that said test compound can be used for preventing or treating a LDLR-associated disease, a VLDLR-associated disease or an ApoER2-associated disease. This method can be conducted in vitro (e.g., in PCSK9-AnxA2 binding assay or PCSK9-LDLR binding assay as that described in Example 9), in a cell (e.g., cells as those described in Examples 5) or in an animal (e.g., appropriate model animal for a LDLR-associated disease, a VLDLR-associated disease, an ApoER2-associated disease).

In accordance with another aspect of the present invention, there is provided a method of identifying or characterizing a compound for preventing or treating a LDLR-associated disease, a VLDLR-associated disease, or an ApoER2-associated disease comprising: a) contacting a test compound with a cell comprising a first nucleic acid comprising a first transcriptionally regulatory element normally associated with an Annexin A2 gene, operably-linked to a second nucleic acid comprising a reporter gene capable of encoding a reporter protein; and b) determining whether the reporter gene expression or reporter activity is increased in the presence of the test compound, wherein an increase in the reporter gene expression or reporter gene activity is indicative that the test compound may be used for treating or preventing or treating a LDLR-associated disease, a VLDLR-associated disease or an ApoER2-associated disease.

In specific embodiments, these methods are for preventing or treating a LDLR-associated disease. In other specific embodiments or these methods, the LDLR-associated disease is hypercholesterolemia.

In accordance with a further aspect of the present invention, there is provided a method of stratifying a subject having a or likely to develop a LDLR-associated disease, a VLDLR-associated disease, an ApoER2-associated disease, or a CD81-associated disease, the method comprising measuring: a) a level of expression of Annexin A2 nucleic acid or encoded polypeptide; b) a level of Annexin A2 activity; or c) a combination of a) and b), wherein the results of the measuring step enables the classification of the subject into a subgroup.

In a specific embodiment, wherein the subject has a LDLR-associated disease. In another specific embodiment, the subject has hypercholesterolemia.

In accordance with a further aspect of the present invention, there is provided a method of inhibiting PCSK9-induced LDLR degradation, or PCSK9-induced VLDLR degradation or PCSK9-induced ApoER2 degradation comprising contacting a cell expressing LDLR or VLDLR or ApoER2 with a polypeptide comprising amino acids of full length AnxA2 isoform 1 or 2 (SEQ ID NO: 1 or 2) or 34-88 of AnxA2 (numbering of amino acids used herein is in reference to that of isoform 2) (SEQ ID NO:3) or 34-97 of AnxA2 (SEQ ID NO:4); 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20); or 49-102 of AnxA2 (SEQ ID NO:21) or 49-108 of AnxA2 (SEQ ID NO:22) (e.g., derived from human AnxA2 isoform 2 disclosed at FIG. 3E); a functional derivative, analogue, conjugate or prodrug of the polypeptide; an activator of Annexin A2 (e.g., a demethylation compound (e.g., 5-azacitydine or decitabine)); a ligand to PCSK9 C-terminal Cys-His-rich-domain (CHRD) or to the M2 subdomain module of the CHRD); p11; or a combination of any of the above.

In a specific embodiment, the inhibitor is a polypeptide comprising amino acids of full length AnxA2 isoform 1 or 2 (SEQ ID NO: 1 or 2) or 34-88 of AnxA2 (numbering of amino acids used herein is in reference to that of isoform 2) (SEQ ID NO:3) or 34-97 of AnxA2 (SEQ ID NO:4); 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20); or 49-102 of AnxA2 (SEQ ID NO:21) or 49-108 of AnxA2 (SEQ ID NO:22) (e.g., derived from human AnxA2 isoform 2 disclosed at FIG. 3E). In another more specific embodiment, the polypeptide is Annexin A2. In another more specific embodiment, the method further comprises p11.

In another specific embodiment, the method is for inhibiting PCSK9-induced LDLR degradation.

In accordance with a further aspect of the present invention, there is provided a polypeptide comprising amino acids of full length AnxA2 isoform 1 or 2 (SEQ ID NO: 1 or 2) or 34-88 of AnxA2 (numbering of amino acids used herein is in reference to that of isoform 2) (SEQ ID NO:3) or 34-97 of AnxA2 (SEQ ID NO:4); 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20); or 49-102 of AnxA2 (SEQ ID NO:21) or 49-108 of AnxA2 (SEQ ID NO:22) (e.g., derived from human AnxA2 isoform 2 disclosed at FIG. 3E) for use in the inhibition of PCSK9-induced LDLR degradation, or PCSK9-induced VLDLR degradation or PCSK9-induced ApoER2 degradation.

In accordance with a further aspect of the present invention, there is provided an Annexin A2 activator (e.g., a demethylation compound (e.g., 5-azacitydine or decitabine)) for use in the inhibition of PCSK9-induced LDLR degradation, or PCSK9-induced VLDLR degradation or PCSK9-induced ApoER2 degradation.

In a specific embodiment, the polypeptide or the activator is for use in the inhibition of PCSK9-induced LDLR degradation.

In accordance with a further aspect of the present invention, there is provided a use of a compound selected from the group consisting of: a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4); 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20); or 49-102 of AnxA2 (SEQ ID NO:21) or 49-108 of AnxA2 (SEQ ID NO:22) (e.g., derived from human AnxA2 isoform 2 disclosed at FIG. 3AE); a functional derivative, analogue, conjugate or prodrug of a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E); an activator of Annexin A2 (e.g., a demethylation compound (e.g., 5-azacytidine or decitabine)); a ligand to PCSK9 C-terminal Cys-His-rich-domain (CHRD) or to the M2 subdomain module of the CHRD); p11; and a combination of any of the above, for inhibiting PCSK9-induced LDLR degradation, or PCSK9-induced VLDLR degradation or PCSK9-induced ApoER2 degradation.

In accordance with a further aspect of the present invention, there is provided a use of a compound selected from the group consisting of: a polypeptide comprising amino acids full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4); 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20); or 49-102 of AnxA2 (SEQ ID NO:21) or 49-108 of AnxA2 (SEQ ID NO:22) (e.g., derived from human AnxA2 isoform 2 disclosed at FIG. 3E); a functional derivative, analogue, conjugate or prodrug of a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4); 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20); or 49-102 of AnxA2 (SEQ ID NO:21) or 49-108 of AnxA2 (SEQ ID NO:22) (e.g., derived from human AnxA2 isoform 2 disclosed at FIG. 3E); an activator of Annexin A2 (e.g., a demethylation compound (e.g., 5-azacytidine or decitabine)); a ligand to PCSK9 C-terminal Cys-His-rich-domain (CHRD) or to the M2 subdomain module of the CHRD); p11; and a combination of any of the above, for the preparation of a medicament for inhibiting PCSK9-induced LDLR degradation, or PCSK9-induced VLDLR degradation or PCSK9-induced ApoER2 degradation.

In a specific embodiment, the uses are for inhibiting PCSK9-induced LDLR degradation.

In accordance with a further aspect of the present invention, there is provided a use of a combination of a compound selected from the group consisting of: a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E); a functional derivative, analogue, conjugate or prodrug of a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E); an activator of Annexin A2 (e.g., a demethylation compound (e.g., 5-azacytidine or decitabine)); a ligand to PCSK9 C-terminal Cys-His-rich-domain (CHRD) or to the M2 subdomain module of the CHRD); p11; and a combination of any of the above, and of a further active agent for the prevention or the treatment of a LDLR-associated disease, or VLDLR-associated disease or ApoER2-associated disease. In a specific embodiment the further active agent is for the prevention or the treatment of a LDLR-associated disease. In a more specific embodiment, the active agent is a cholesterol synthesis inhibitor (e.g., statin).

In accordance with a further aspect of the present invention, there is provided a use of a commercial kit comprising a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E) and a cholesterol synthesis inhibitor (e.g., statin).

In accordance with a further aspect of the present invention, there is provided a use of a commercial kit comprising a polypeptide comprising an Annexin A2 activator (e.g., a demethylation compound (e.g., 5-azacytidine or decitabine)) and cholesterol synthesis inhibitor (e.g., statin).

In accordance with a further aspect of the present invention, there is provided a use of a purified polypeptide comprising amino acids 34-88 of AnxA2 (numbering of amino acids used herein below is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E) with the proviso that said polypeptide does not the sequence of SEQ ID NO: 1 or 2 (i.e., full length AnxA2 isoform 1 or 2 (SEQ ID NO: 1 or 2)).

In accordance with a further aspect of the present invention, there is provided a use of a pharmaceutical composition comprising a polypeptide of the present invention, and a pharmaceutically acceptable carrier.

In accordance with a further aspect of the present invention, there is provided a use of a purified antibody that binds specifically to annexin A2 or a polypeptide derived therefrom (i.e. purified polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E)).

In accordance with a further aspect of the present invention, there is provided an isolated nucleic acid molecule encoding a polypeptide of the present invention.

In accordance with a further aspect of the present invention, there is provided a vector comprising a nucleic acid molecule of the present invention.

In accordance with a further aspect of the present invention, there is provided a recombinant host cell comprising a vector of the present invention.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 2. PCSK9 binds to a ~33 kDa protein. (A) Schematic diagram of the full-length (FL) PCSK9-V5, PCSK9 without its CHRD (L455X-V5) or the CHRD-V5 constructs used for Far Western blotting. (B-E) Far Western blot (FWB) assays of cell and tissue lysates using conditioned media of CHO-K1 cells overexpressing pIRES-V5, PC5A-V5, PCSK9-V5 or mutants thereof. All of these were detected by the HRP-tagged V5 mAb. (B) The COS-1 cells soluble fraction (supernatant S3; 3 µg protein) was analyzed by Far Western blot and compared to 30 µg protein loads from other subcellular fractions. (C) Far Western blots of COS-1 lysates incubated with PCSK9-V5 or different fragments and mutants thereof and revealed using the HRP-tagged V5 mAb except for D374Y which is not V5-tagged and was revealed using a PCSK9 polyclonal antibody[15]. (D) For competition experiments, purified PCSK9-His or CHRD-His were added to the PCSK9-V5 conditioned media used for Far Western blotting. (E) PCSK9-V5-binding requirements were tested by adding 1M NaCl, 10 mg/ml heparin, 1M NaCl+10 mg/ml heparin, or 100 mM EDTA to the PCSK9-V5 conditioned media used for Far Western blotting. Heavy arrows point to the migration position of the ~33 kDa protein, and the light arrow to that of the ~45 kDa protein. (−) denotes a control lane where nothing was added to the Far Western blotting media;

FIG. 3. PCSK9 co-immunoprecipitates with endogenous Annexin A2. (A) Lysates of pIRES-V5- or PCSK9-V5-transfected COS-1 cells were immunoprecipitated with anti-V5-agarose beads. The antigen-antibody complexes were separated by SDS-PAGE (8%) and Coomassie blue stained. For both pIRES-V5 and PCSK9-V5 conditions, the bands at ~33 kDa were excised (boxed areas) and proteins analyzed by mass spectrometry. (B) As a control for the immunoprecipitation, antigens complexed with the anti-V5-agarose beads were eluted with the V5 peptide, separated by SDS-PAGE and revealed by Western blotting with the anti-V5 antibody. (C-E) Identification of the PCSK9 binding partner in COS-1 cells by 2D Far Western blot, 2D SDS-PAGE and mass spectrometry. (C-D) COS-1 cell lysates were separated by a first horizontal dimension using a wide pH range isoelectrofocussing gel strip (pH 3-10) and then vertically by SDS-PAGE (12%). After SDS-PAGE, proteins were either Coomassie blue stained (C) or electrotransfered onto a nitrocellulose membrane and probed by Far Western with PCSK9-V5 (D). Spots (C, boxed area) were aligned with those of the Far Western blot (D) using Photoshop software, excised and the proteins analyzed by mass spectrometry after trypsin digestion. (E) Results of the mass spectrometry Mascot analysis identifying the presence of AnxA2 isoform 2 (SEQ ID NO: 2) with 77% peptide coverage (bold sequences);

FIG. 4. Characterization of the interaction of PCSK9 with AnxA2. (A) PCSK9-V5 Far Western blot of lysates of COS-1 cells, wild type (WT) CHO-K1 cells, CHO-K1 cells overexpressing an empty vector (pIRES), AnxA1 or AnxA2. (B) Poly-histidine pull-down assay. Purified native AnxA2-$(His)_6$ or AnxA1-$(His)_6$ were immobilized on cobalt chelate beads and incubated with PCSK9-V5. Bound proteins were released from beads in Laemmli sample buffer and analyzed by Western blotting with the anti-V5-HRP or anti-His-HRP antibodies and revealed by ECL. PCSK9 (heavy arrow) and its furin-cleaved form (PCSK9-Δ218; light arrow) were pulled-down by AnxA2. (C) Co-immunoprecipitation experiments of CHO-K1 cells co-transfected with PCSK9-V5 and either AnxA1-HA, AnxA2-HA or with AnxA2-HA and p11. Proteins immunoprecipitated with the anti-V5 mAb were revealed by Western blotting with anti-HA-HRP or anti-V5-HRP antibodies. Expression of the transfected constructs was analyzed by Western blotting of cell lysates using the anti-V5-HRP or anti-HA-HRP antibodies. (D, left panel) PCSK9-V5 Far Western blots of purified AnxA2-$(His)_6$ in the absence or presence of reducing agents. Note that in non-reducing conditions, PCSK9-V5 binds both the dimer and monomer forms of AnxA2. (D, right panel) Western blots of the purified AnxA2-(His)$_6$ using the anti-AnxA2 mAb in non-reducing or reducing conditions. (E, upper panel) Media from CHO-K1 cells expressing PCSK9-V5 or the CHRD-V5 were separated by SDS-PAGE (8%), transferred onto nitrocellulose, incubated with purified AnxA2-(His)$_6$ and probed with the anti-His-HRP antibody. (E, lower panel) The presence of overexpressed PCSK9 and CHRD in CHO-K1 cell media was verified by Western blotting using anti-V5-HRP;

FIG. 5. The PCSK9 natural loss of function mutant Q554E (a component of the PCSK9 M2 subdomain module of the CHRD) strongly binds AnxA2. (A) Western blot analysis of conditioned media from CHO-K1 cells overexpressing PCSK9-V5 or its natural mutant Q554E-V5 used for Far Western blotting. (B) Far Western blots of extracts from COS-1 CHO-K1 or AnxA2-transfected CHO-K1 cells with the PCSK9-V5 or Q554E-V5 conditioned media of CHO-K1 cells analyzed in (A). The relative intensity of the binding of PCSK9-V5 (taken as 1×) or of the Q554E-V5 mutant (3× higher) to AnxA2 was calculated and normalized with respect to β-actin;

FIG. 6. PCSK9 and AnxA2 co-localize at the cell surface. CHO-K1 cells co-transfected with AnxA2-HA and PCSK9-V5 were fixed under non-permeabilizing conditions. Cell surface immunofluorescence was performed using the anti-HA mAb (green labeling) and anti-V5 polyclonal Ab (red labeling). Nuclei of transfected cells are marked by the EGFP fluorescence (pseudo-colored blue). Arrows indicate areas of co-localization. These data are representative of at least 20 independent cell clusters. Bar=10 µm;

FIG. 7. AnxA2 inhibits the PCSK9-enhanced LDLR degradation. (A) Lysates of CHO-K1 cells transfected with an empty vector (pIRES), or co-transfected with either PCSK9 and pIRES or PCSK9 and AnxA2, were analyzed by Western blot using the anti-LDLR and anti-β-actin antibodies. The relative intensity calculated for LDLR was normalized over the β-actin signal. (B) Lysates of HepG2 cells transfected with pIRES or co-transfected with either AnxA2 and pIRES or with AnxA2 and p11 were analyzed by Western blot using anti-LDLR and anti-actin antibodies. (C) LDLR and β-actin Western blots of lysates of HepG2 cells incubated with conditioned media from untransfected (control, Ctl) or PCSK9-transfected CHO-K1 cells with or without exogenous addition of 5 µg/ml of purified AnxA2-His. (D-F) CHO-K1 cells overexpressing the LDLR were incubated at 4° C. for 1 h with 1 µg of purified PCSK9-(His)$_6$ alone (D), or with the addition of 5 µg (E) or 20 µg (F) of purified AnxA2-(His)$_6$. Cells were then fixed under non-permeabilizing conditions and cell surface PCSK9 was visualized by immunofluorescence using the anti-PCSK9 antibody. These data are representative of at least 15 independent cell clusters. Bars=10 µm;

FIG. 8. The level of LDLR increases at the surface of AnxA2-transfected cells. HepG2 cells transfected with (A) pIRES, (B) AnxA2, (C) AnxA2 and p11-YFP, (D) PCSK9, (E) PCSK9 and AnxA2 or (F) with the PCSK9 gain-of-function mutant D374Y and AnxA2 or the D374Y alone (F, inset) were fixed under non-permeabilizing conditions. Cell surface immunofluorescence was performed using the anti-LDLR (green labeling). Nuclei of transfected cells are marked by the EGFP fluorescence (pseudo-colored blue). Arrows point to the LDLR labeling at the surface of transfected cells. (C) p11-YFP and LDLR labelings were pseudo-colored blue and green, respectively. These data are representative of more than 40 independent cell clusters. Bars=10 µm;

FIG. 9. shRNA knockdown of AnxA2 enhances LDLR degradation. (A) HuH7 cells were stably transfected with a control shRNA (Ctl) or with a specific shRNA against AnxA2 and analyzed for their LDLR, AnxA2 and β-actin content by Western blot. (B) HuH7 cells were transiently transfected with the control or the AnxA2 shRNA. Levels of AnxA2 knockdown and those of LDLR were revealed by Western blot and calculated relative to β-actin. (C) Lysates of HEK293 (cells expressing very little PCSK9) cells transfected with AnxA2, AnxA2-HA, AnxA1, AnxA1-HA, p11, or co-transfected with AnxA2 and p11 or with AnxA2-HA and the AnxA2 shRNA (D) were analyzed by Western blotting using the anti-LDLR, anti-AnxA2 or anti-βactin. (E) HuH7 cells transiently transfected with the AnxA2 shRNA were fixed under non-permeabilizing conditions and labeled for AnxA2 (red) and LDLR (green). Cells showing low levels of AnxA2 labeling were localized and analyzed for their LDLR content at the plasma membrane. Dotted lines indicate the presence of a cell (inset) with low AnxA2 and LDLR surface labeling. These data are representative of at least 4 independent cell clusters;

FIG. 10. Identification of the R1 repeat domain of AnxA2 as the PCSK9-interacting sequence. (A) Schematic representation of human AnxA2 domains (aa 1-24; R1: aa 37-102; R2: aa 109-174; R3: 193-259; R4: aa 269-334). Deletion mutations for all repeats include the C-terminal linker sequences (ΔR1: aa 37-108; ΔR2: aa 109-192; ΔR3: 193-268; ΔR4: aa 269-339). (B) HEK293 cells were transfected with full-length human AnxA2, its N-terminal deletant Δ2-24, or with HA-tagged full-length human AnxA2 and HA-tagged deletants (ΔR1, ΔR2, ΔR3, ΔR4). Far Western blotting (FWB) was performed on nitrocellulose membranes using conditioned media obtained from CHO-K1 cells overexpressing PCSK9-V5 (Top panel). Expression of the constructs was verified by Western blot (WB) using anti-AnxA2 or anti-HA-HRP antibodies. (C) Comparison of the amino acid sequences of the R1 repeats of AnxA2 (binding to PCSK9) (25-108 AnxA2 (SEQ ID NO: 14)) and AnxA1 (34-117 ANX1 (SEQ ID NO: 23)) (not binding to PCSK9);

FIG. 11. AnxA2 R1 domain sequence required for binding to PCSK9-V5 by far western blots. (A-B) HEK293 cells were transfected with HA-tagged full-length human AnxA2 (FL), or HA-tagged deletants (Δ), point mutants of the R1 repeat, or (B) with HA-tagged AnxA2 constructs in which aa were replaced by the corresponding AnxA1 aa (AnxA1>AnxA2 shown in C). Following SDS-PAGE (10%) Far Western blotting (FWB) was performed on nitrocellulose membranes using conditioned media obtained from CHO-K1 cells overexpressing PCSK9-V5. Expression of the constructs was verified by Western blot (WB) using anti-AnxA2 or anti-HA-HRP antibodies. (C) Deduced AnxA2 R1 domain sequence necessary for PCSK9-V5 binding by Far Western Blot (aa 34-108, in bold (SEQ ID NO: 6)) (25-108 AnxA2 (SEQ ID NO: 14) and 34-117 AnxA1 (SEQ ID NO: 23);

FIG. 14. Relative mRNA expression of AnxA2 in human cell lines. Quantitative polymerase chain reactions were performed on RNA isolated from human cell lines using specific oligonucleotides for human AnxA2, PCSK9 and normalized to $10^6$ S14 mRNA levels, as described in Example 1. HUVEC, umbilical vein endothelial cells; A549, lung carcinoma; Hela, cervix adenocarcinoma; HT-29, colon adenocarcinoma; U87, epithelial-like glioblastoma-astrocytoma; HuH7, hepatoma; Caco2, colorectal adenocarcinoma; Lovo-C5, colon adenocarcinoma; A431, epithelial carcinoma; BON-1, endocrine pancreatic tumor; HepG2, hepatocellular liver carcinoma; Ben, epidermoid bronchial carcinoma; HT-1080, human fibrosarcoma; MCF7, epithelial breast cancer; SW13, adrenal carcinoma; HEK293, embryonic kidney cells; SKNM, neuroepithelioma; JurkatF, T cell lymphoblast-like; H295R, adrenocortical carcinoma;

FIG. 16. The DNA-methylation inhibitor 5-Azacytidine regulates AnxA2, PCSK9 and LDLR expression in HepG2 cells. (A) Media and lysates of HepG2 cells treated with 5-Azacytidine (10 or 25 μM) for 24 or 48 hours were analyzed by Western blot for LDLR, PCSK9, AnxA2 and actin content. (B) HepG2 cells treated with 5-Azacytidine (10 μM or 25 μM) for 24 hours were analyzed by qPCR for PCSK9, LDLR, HMG-CoA reductases (involved in cholesterol synthesis pathway) and AnxA2. Error bars represent 3 biological samples done in qPCR duplicates; and FIG. 17. presents Annexin A2 sequences; A) the nucleotide sequence (SEQ ID NO: 24) and amino acid sequence (SEQ ID NO: 2) of annexin A2 isoform 2 (NM_001002857.1→NP_001002857.1); and B) the nucleotide sequence (SEQ ID NO: 25) and amino acid sequence (SEQ ID NO: 1) of annexin A2 isoform 1 (NM_001002858.2→NP_001002858.1).

DESCRIPTION OF ILLUSTRATIVE EMBODIMENTS

Figure 1:
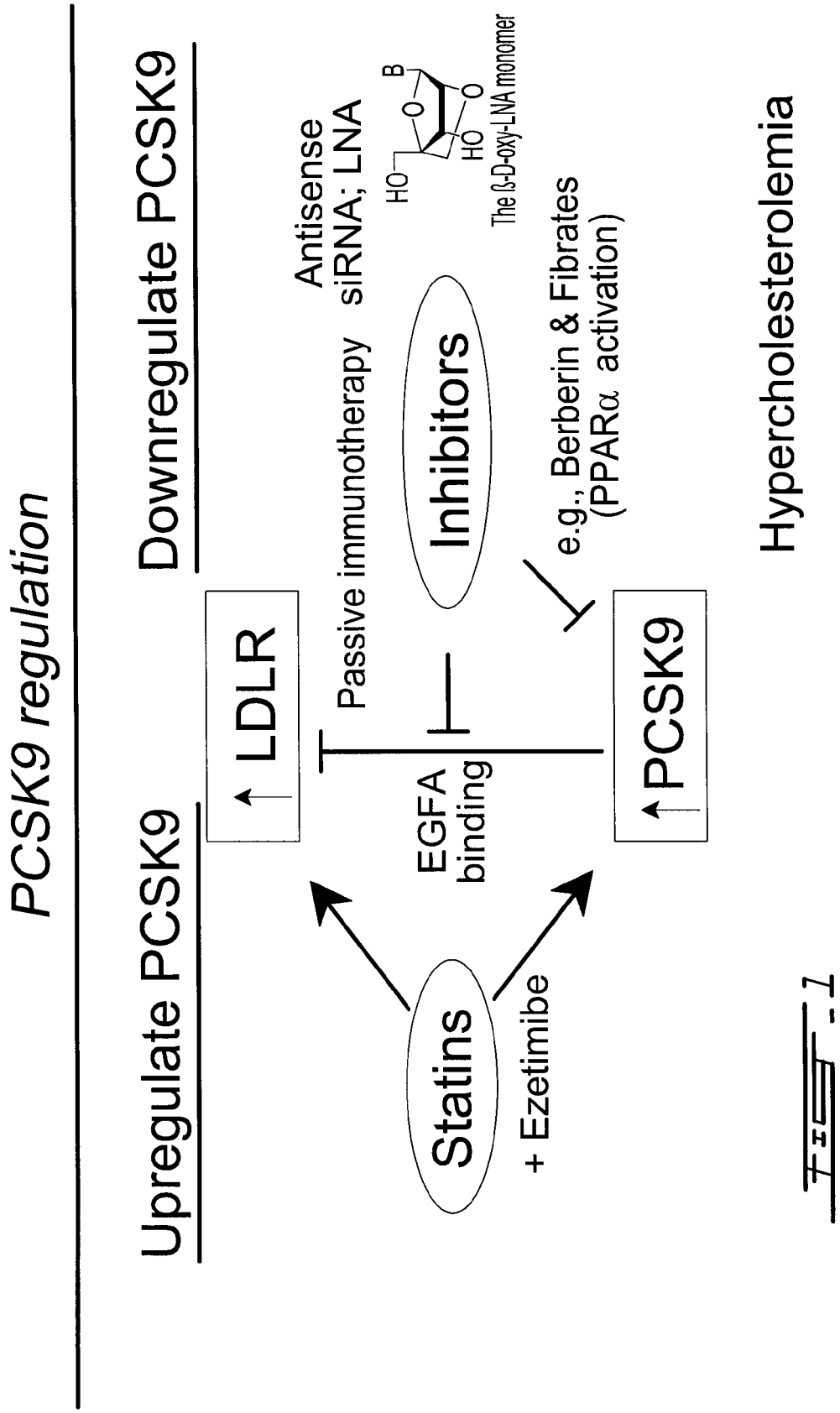
FIG. 1 is a schematic diagram of PCSK9 regulation. The widely used statin therapy is known to upregulate both the LDLR and its degradation factor PCSK9. Thus, specific PCSK9 inhibitors, directly targeting PCSK9 or a subdomain of PCSK9 and having an effect on the PCSK9-LDLR interaction, will constitute valuable assets for cholesterol-lowering therapies.

The wide interest in developing a specific PCSK9-inhibitor/silencer, led to the proposal of multiple approaches (FIG. 1), which include the identification of inhibitors of PCSK9-LDLR interaction that occurs through the EGF-A domain of LDLR[19]. Natural point mutations of PCSK9 in either the pro-domain or the C-terminal Cys-His-rich-domain (CHRD) result in either hyper- or hypo-cholesterolemia[3], even though they are not implicated in the direct interaction of the catalytic domain with the LDLR/EGF-A[19]. These include the H553R and Q554E within the CHRD that result in hyper- and hypo-cholesterolemia via gain or loss of function of PCSK9, respectively[6,20].

While the C-terminal Cys-His rich domain (CHRD) of PCSK9 is a spatially separate domain that does not participate directly in the PCSK9-LDLR EGF-A interaction, it is a critical determinant for the PCSK9-enhanced cellular degradation of the LDLR[36]. In agreement, it was recently demonstrated that annexin A2, which binds the CHRD of PCSK9, blocks its effect on LDLR degradation[37].

A far Western screen was set up to identify a PCSK9 specific interaction partner amongst different cell line extracts. This analysis revealed that such a protein, the annexin A2 or AnxA2, does exist in certain cells and that it interacts specifically with the CHRD, resulting in inhibition of the PCSK9 activity, e.g., the decreased ability of PCSK9 to interact with LDLR as well as to enhance the degradation of LDLR.

PCSK9 inhibitors, directly targeting the annexin A2 binding domain on PCSK9, constitute valuable assets for cholesterol-lowering therapies.

AnxA2 activators, indirectly targeting the PCSK9 activity, also constitute valuable assets for cholesterol-lowering therapies.

As used herein the terms "PCSK9-associated disease" refer to diseases resulting in part from a defective PCSK9 activity (e.g., an increased activity) and diseases resulting in part from a defective activity of a PCSK9 target such as LDLR, VLDLR, ApoER2 or CD81[21]. Similarly, as used herein the terms "LDLR-associated disease", "VLDLR-associated disease", "ApoER2-associated disease" and "CD81-associated disease" refer to diseases resulting in part from a defective LDLR activity (e.g., a decreased activity), a defective VLDLR activity, a defective ApoER2 activity or a defective CD81 activity (e.g., an increased activity), respectively. For instance, as defined herein, hypercholesterolemia is an LDLR-associated disease, while fetal growth restriction is a ApoER2-associated disease, the recessive form of non-progressive cerebellar ataxia found in the Hutterite population is a VLDLR-associated disease and a decrease of CD81 in the presence of a high activity level of PCSK9 proteins was shown to be associated with a decreased viral infection of HCV. Without being so limited, PCSK9-associated diseases include cardiovascular diseases such as hypercholesterolemia, atherosclerosis, stroke and ischemia; schizophrenia, autism; fetal growth restriction; obesity; and a recessive form of non-progressive cerebellar ataxia.

As used herein, the term "subject" in the context of the present invention relates to any mammal including a mouse, rat, rabbit, pig, monkey and horse. In a specific embodiment, it refers to a human.

A "subject in need thereof" or a "patient" in the context of the present invention is intended to include any subject that will benefit or that is likely to benefit from the increase in the expression or activity of Annexin A2. In an embodiment, a subject in need thereof is a subject diagnosed with a LDLR-associated disease, a VLDLR-associated disease or an ApoER2-associated disease. In another embodiment, the subject is likely to develop a LDLR-associated disease, a VLDLR-associated disease or an ApoER2-associated disease. The likelihood of developing hypercholesterolemia can be determined for instance with the prevalence of the disease/condition in close members of the family (sisters, brothers, parents, grand-parents, uncles and aunts) or by determining whether the subject has an underlying disease or condition that is likely to be associated with any of such diseases (e.g., cardiovascular disease such as angina pectoris, early or late onset myocardial infarction, transient ischemic attacks, stroke, peripheral artery disease and atherosclerosis). In yet another embodiment, a subject in need thereof is a subject undergoing therapy for an underlying disease or condition which is associated with hypercholesterolemia or likely to be associated with hypercholesterolemia. In another embodiment, the subject in need thereof is a subject suffering from an underlying disease but which has not yet developed hypercholesterolemia.

A "subject in need thereof" or a "patient" in the context of the present invention is also intended to include any subject that will benefit or that is likely to benefit from the decrease in the expression or activity of Annexin A2. In an embodiment, a subject in need thereof is a subject diagnosed with a viral infection (e.g., hepatitis C virus (HCV)).

As used herein the terminology "biological sample" refers to any solid or liquid sample isolated from a living being. In a particular embodiment, it refers to any solid or liquid sample isolated from a human. Without being so limited it includes a biopsy material, blood, saliva, synovial fluid, urine, amniotic fluid and cerebrospinal fluid.

As used herein the terminology "blood sample" is meant to refer to blood, plasma or serum.

As used herein the terminology "control blood sample" is meant to refer to a blood sample of a subject known not to suffer from the PCSK9-associated disease under scrutiny in the assay. In specific embodiments, it is the sample of a subject not known to suffer from a PCSK9-associated disease. In particular embodiments where dyslipidemia is under scrutiny, it thus refers to a subject known not known to suffer from dyslipidemia.

As used herein, the terms "treat/treating/treatment" and "prevent/preventing/prevention", refer to eliciting the desired biological response, i.e., a therapeutic and prophylactic effect, respectively. In accordance with the subject invention, the therapeutic effect comprises one or more of a partial or complete reduction of a phenotype of a LDLR-associated disease such as hypercholesterolemia, a VLDLR-associated disease an ApoER2-associated disease or a CD81-associated disease. More particularly, a therapeutic effect may comprise a partial or complete reduction of a phenotype of hypercholesterolemia such as a decrease/reduction in amounts of circulating LDL-cholesterol. In accordance with the invention, a prophylactic effect may comprise a delay or decrease in the onset of, progression of or the severity of a phenotype of a LDLR-associated disease such as hypercholesterolemia, a VLDLR-associated disease, an ApoER2-associated disease or a CD81-associated disease.

As used herein, the term "compound" broadly refers to natural, synthetic or semi-synthetic molecules. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The compound appropriate for the present invention can be selected and screened by a variety of means including random screening, rational selection and by rational design using for example protein or ligand modeling methods such as computer modeling. The terms "rationally selected" or "rationally designed" are meant to define compounds which have been chosen based on the configuration of interacting domains of the present invention (e.g., the annexin A2 binding domain on the PCSK9-CHRD). As will be understood by the person of ordinary skill, macromolecules having non-naturally occurring modifications are also within the scope of the term "compound". For example, peptidomimetics, well known in the pharmaceutical industry and generally referred to as peptide analogs can be generated by modeling as mentioned above.

Antibodies

Antibodies encompassed by the present invention specifically bind to (interacts with) a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 1 disclosed at FIG. 3E) and display no substantial binding to other naturally occurring proteins other than the ones sharing the same antigenic determinants as the polypeptide. The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PepBodies™, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g. Fab and Fab' fragments) which inhibit or neutralize their respective interaction domains in Hyphen and/or are specific thereto.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen, immunogenic conjugates, or derivatives by combining the antigen or conjugate (e.g., 100 µg for rabbits or 5 µg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum et al., 2004).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (see, e.g., Goding 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

As used herein, the term "a" or "the" means "at least one".

As used herein the term "purified" in the expression "purified polypeptide" means altered "by the hand of man" from its natural state (i.e. if it occurs in nature, it has been changed or removed from its original environment) or it has been synthesized in a non-natural environment (e.g., artificially synthesized). These terms do not require absolute purity (such as a homogeneous preparation) but instead represents an indication that it is relatively more pure than in the natural environment. For example, a protein/peptide naturally present in a living organism is not "purified", but the same protein separated (about 90-95% pure at least) from the coexisting materials of its natural state is "purified" as this term is employed herein.

Similarly, as used herein, the term "purified" in the expression "purified antibody" is simply meant to distinguish man-made antibody from an antibody that may naturally be produced by an animal against its own antigens. Hence, raw serum and hybridoma culture medium containing antibodies that specifically bind to the polypeptide of the present invention are "purified antibodies" within the meaning of the present invention.

As used herein the term "Annexin A2" refers to any known isoform of Annexin A2. Without being so limited, it includes annexin A2 isoform 1 (NM_001002858.1, NP_001002858.1), and annexin A2 isoform 2 (NM_001002857.1, NP_001002857.1 (shown in FIG. 17); NM_004039.2, NP_004030.1). See also Tables 1 and 2 below for other Annexin A2 nucleic acid or encoded polypeptides.

TABLE 1

Accession numbers of Annexin A2 nucleic acid and protein amino acid sequences

| | Nucleotide | Protein |
|---|---|---|
| Genomic | AC087385.5 (121535..172370) | None |
| Genomic | CH471082.1 | EAW77582.1 |
| | | EAW77583.1 |
| | | EAW77584.1 |
| | | EAW77585.1 |
| | | EAW77586.1 |
| | | EAW77587.1 |
| Genomic | CQ878716.1 | CAH59520.1 |
| mRNA | AK092006.1 | None |
| mRNA | AK124427.1 | None |
| mRNA | AK222542.1 | None |
| mRNA | AW087150.1 | None |
| mRNA | BC001388.2 | AAH01388.1 |
| mRNA | BC001748.1 | None |
| mRNA | BC009564.1 | AAH09564.1 |
| mRNA | BC013843.1 | None |
| mRNA | BC015834.1 | AAH15834.1 |
| mRNA | BC016774.1 | AAH16774.1 |
| mRNA | BC021114.1 | AAH21114.1 |
| mRNA | BC023990.1 | AAH23990.1 |
| mRNA | BC052558.1 | AAH52558.1 |
| mRNA | BC052567.1 | AAH52567.1 |
| mRNA | BC066955.1 | AAH66955.2 |
| mRNA | BC068065.1 | AAH68065.1 |
| mRNA | BC093056.1 | AAH93056.1 |
| mRNA | BT007432.1 | AAP36100.1 |
| mRNA | BX640598.1 | CAE45704.1 |
| mRNA | CR590378.1 | None |
| mRNA | CR595032.1 | None |
| mRNA | CR595469.1 | None |
| mRNA | CR596938.1 | None |
| mRNA | CR597222.1 | None |
| mRNA | CR597904.1 | None |
| mRNA | CR598583.1 | None |
| mRNA | CR599823.1 | None |
| mRNA | CR600114.1 | None |
| mRNA | CR608031.1 | None |
| mRNA | CR611402.1 | None |
| mRNA | CR616100.1 | None |
| mRNA | CR616357.1 | None |
| mRNA | CR617962.1 | None |
| mRNA | CR618374.1 | None |
| mRNA | CR618857.1 | None |
| mRNA | CR620533.1 | None |
| mRNA | CR622642.1 | None |
| mRNA | CR622682.1 | None |
| mRNA | CR625736.1 | None |
| mRNA | D00017.1 | BAA00013.1 |
| mRNA | D28364.1 | BAA05730.1 |
| Synthetic | DQ891008.2 | ABM81934.1 |
| Synthetic | DQ894187.2 | ABM85113.1 |
| | | P07355 |
| | | Q53HN8 |
| | | Q6N0B3 |
| | | Q8TBV2 |
| | | CQ878716 |

TABLE 2

Natural genetic variants of the human AnxA2 protein.

| ID | Type | Chr: bp | Alleles | Amino Acid | AA coordinate | Class | Source | Validation |
|---|---|---|---|---|---|---|---|---|
| rs17852168 | Non Synonymous Coding | 15: 58428648 | A/G | V/A | 293 | snp | dbSNP | — |

TABLE 2-continued

Natural genetic variants of the human AnxA2 protein.

| ID | Type | Chr: bp | Alleles | Amino Acid | AA coordinate | Class | Source | Validation |
|---|---|---|---|---|---|---|---|---|
| rs35211583 | Frameshift Coding | 15: 58430690-58430689 | —/G |  | 278 | insertion | dbSNP | — |
| rs1803909 | Non Synonymous Coding | 15: 58430716 | A/G | Y/H | 269 | snp | dbSNP | — |
| rs35011360 | Frameshift Coding | 15: 58430719-58430718 | —/G |  | 268 | insertion | dbSNP | — |
| rs41307613 | Non Synonymous Coding | 15: 58435453 | T/C | D/G | 162 | snp | dbSNP | — |
| rs1059688 | Non Synonymous Coding | 15: 58440497 | G/T | V/L | 98 | snp | dbSNP | — |
| rs17845226 | Non Synonymous Coding | 15: 58440497 | C/A | V/L | 98 | snp | dbSNP | Cluster |
| rs11553794 | Non Synonymous Coding | 15: 58443976 | G/T | R/S | 63 | snp | dbSNP | hapmap |

As observed for PCSK9, natural point mutations of AnxA2 could lead to gain of function or loss of function phenotypes. Variants rs1059688, rs17845226 and rs11553794 are examples of natural point mutations of AnxA2 modifying the R1 region.

In contrast to gene mutation, epigenetic change may be reversible. Therefore, targeting epigenetic changes in an attempt to relieve transcriptional repression has been an attractive therapeutic strategy. Agents that have been extensively studied include DNMT inhibitors. Some of these DNMT inhibitors have been investigated in preclinical models and in clinical experiences.

DNMT inhibitors do not remove methyl groups from methylated chromatin, but rather prevent methylation of daughter DNA in CpG islands during DNA replication. Methyltransferase inhibitors include the nucleoside inhibitors 5-azacitydine (azacitydine), 5-aza-2'-deoxycitydine (decitabine), and zebularine. These agents are incorporated into DNA and the end results is depletion of methyltransferase and demethylation of DNA. Azacitydine (Vidaza, Pharmion) is a pyrimide nucleoside analog of cytidine. It has been approved by the FDA for treatment of myelodysplastic syndromes of all subtypes. Decitabine (Dacogen, MGI Pharma) is a deoxycytidine analog prodrug activated by deoxycytidine kinase, and was recently FDA-approved for mylidysplastic syndrome. Recent studies in leukemia suggest that the dose of DNMT inhibitor required to re-express epigenetically silenced gene is far less than maximal tolerated dose.

In relation to the present invention, it was demonstrate that treatment of LNCaP cells with 5-azacytidine induced an increase of expression of Annexin II[22].

As used herein the term "Annexin A2 activator" refers to a compound that increases expression (transcription, translation and/or stability) of Annexin A2 or increases Annexin A2 activity or both (e.g., a demethylation compound (e.g., 5-azacitydine or decitabine)).

As used herein the term "Annexin A2 inhibitor" refers to a compound that decreases expression (transcription, translation and/or stability) of Annexin A2 or decreases Annexin A2 activity or both (e.g., the AnxA2-shRNA described in Example 6).

As used herein the term "Annexin A2 activity" includes without being so limited binding of Annexin A2 to PCSK9 or a fragment thereof, (e.g., binding of Annexin A2 to the CHRD domain of PCSK9), binding of Annexin A2 to p11, translocation of Annexin A2 to the cell membrane, modulation of the traffic of PCSK9 and/or LDLR (e.g., the cell surface), prevention of PCSK9-induced degradation of LDLR, VLDLR, ApoER2 or CD81, and prevention of PCSK9 binding to LDLR, VLDLR, ApoER2 or CD81.

The increasing of AnxA2 expression and/or activity could be achieved by various mechanisms, which among others could act at the level of (i) transcription (e.g., decreasing a transcriptional methylation block) (ii) translation, (iii) post-translational modifications, e.g., glycosylation, sulfation, phosphorylation, ubiquitination (iv) cellular localization. These regulatory processes occur through different molecular interactions that could be modulated by a variety of compounds or modulators.

As used herein in relation to the present technology the term "PCSK9 inhibitors" refers to a compound specifically targeting the AnxA2 binding domain on PCSK9 and that reduces a PCSK9 activity. Without being so limited, examples of PCSK9 inhibitors includes polypeptides comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E) and variants thereof.

Polypeptides of the present invention can be modified while retaining their activities. They can further be labeled during chemical synthesis (e.g., His$_6$, tritiated L-leucine, biotinylated derivative of amino acids, adding a N-terminal tyrosine residue that can be iodinated according to standard methods, etc.).

In specific embodiments, the modification is a deletion, an insertion, a substitution or a chemical modification of one or more amino acids. The modification may be, for example, a deletion of (e.g., one to ten) consecutive or non-consecutive amino acids, a substitution of (e.g., one to ten) amino acids, one or more substitution(s) of a naturally occurring amino acid (L-amino acid) by a corresponding D-amino acid, an extension of the sequence by e.g., one, two, three or more amino acids at the C or T terminal of the peptide. In an embodiment, the above-mentioned substitution(s) are conserved amino acid substitutions.

As used herein, the term "conserved amino acid substitutions" (or sometimes "conservative amino acid substitutions") refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In other embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In other embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In other embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Biol.* 179: 125-142, 1984). Genetically encoded hydrophobic amino acids include Gly, Ala, Phe, Val, Leu, Ile, Pro, Met and Trp, and genetically, encoded hydrophilic amino acids include Thr, His, Glu, Gln, Asp, Arg, Ser, and Lys.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents.

An apolar amino acid is a hydrophobic amino acid with a side chain that is uncharged at physiological pH and which has bonds in which a pair of electrons shared in common by two atoms is generally held, equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

The above classifications are not absolute and an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid.

In addition to the substitutions outlined above, synthetic amino acids providing similar side chain functionality can also be introduced into the peptide. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl.

Non-carboxylate amino acids can be made to possess a negative charge, as provided by phosphono- or sulfated (e.g., —$SO_3H$) amino acids, which are to be considered as non-limiting examples.

Other substitutions may include unnatural alkylated amino acids, made by combining an alkyl group with any natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine. In addition, any amide linkage in the peptide may be replaced by a ketomethylene, hydroxyethyl, ethyl/reduced amide, thioamide or reversed amide moieties, (e.g., (—C═O)—$CH_2$—), (—CHOH)—$CH_2$—), ($CH_2$—$CH_2$—), (—C═S)—NH—), or (—NH—(—C═O) for (—C═O)—NH—)).

Other modifications are also included within the definition of variant of the bifunctional hormone of the present invention. For example, the size of the peptides can be reduced by deleting one or more amino acids, and/or amino acid mimetics or dipeptide mimics containing non-peptide bonds may be used. Examples of using molecular scaffolds such as benzodiazepine, azepine, substituted gamma lactam rings, ketomethylene pseudopeptides, β-turn dipeptide cores and β-aminoalcohols for these purposes are known to peptide chemists and are described in for example *Peptidomimetic protocols* (Methods in molecular medicine Vol. 23) W. M. Kazmierski (ed.), Humana Press and *Advances in Amino Acid Mimetics and Peptidomimetics*, Vols. 1 & 2, A. Abell (Ed).

Covalent modifications of the peptide are thus included within the scope of the present invention. Such modifications may be introduced into the bifunctional hormone for example by reacting targeted amino acid residues of the polypeptide with an organic derivatizing agent that is capable of reacting with selected side chains or terminal residues. The following examples of chemical derivatives are provided by way of illustration and not by way of limitation.

Cysteinyl residues may be reacted with alpha-haloacetates (and corresponding amines), such as 2-chloroacetic acid or chloroacetamide, to give carboxymethyl or carboxyamidomethyl derivatives. Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0. Lysinyl and amino terminal residues may be reacted with compounds such as succinic or other carboxylic acid anhydrides. Other suitable reagents for derivatizing alpha-amino-containing residues include compounds such as imidoesters, e.g. methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues is typically performed in alkaline conditions because of the high pKa of the guanidine functional group. Furthermore, these reagents may react with the groups of lysine as well as the arginine epsilon-amino group. The specific modification of tyrosinyl residues per se is well-known, such as for introducing spectral labels into tyrosinyl residues by reaction with aromatic diazonium compounds or tetranitromethane. N-acetylimidazol and tetranitromethane may be used to form O-acetyl tyrosinyl species and 3-nitro derivatives, respectively.

Carboxyl side groups (aspartyl or glutamyl) may be selectively modified by reaction with carbodiimides (R'—N═C═N—R') such as 1-cyclohexyl-3-(2-morpholinyl-(4-ethyl)carbodiimide or 1-ethyl-3-(4-azonia-4,4-dimethylpentyl)carbodiimide. Furthermore aspartyl and glutamyl residues may be converted to asparaginyl and glutaminyl residues by reaction with ammonium ions. Glutaminyl and asparaginyl residues may be frequently deamidated to the corresponding glutamyl and aspartyl residues. Other modifications of the peptides in the present invention may include hydroxylation of proline and lysine, phosphorylation of hydroxyl groups of seryl or threonyl residues, methylation of the alpha-amino groups of lysine, arginine, and histidine side chains acetylation of the N-terminal amine, methylation of main chain amide residues (or substitution with N-methyl amino acids) and, in some instances, amidation of the C-terminal carboxyl groups, according to known method steps.

Covalent attachment of fatty acids (e.g., $C_6$-$C_{18}$) to the peptides may confer additional biological properties such as protease resistance, plasma protein binding, increased plasma half-life, intracellular penetration, etc. The above description of modification of polypeptides or the present does not limit the scope of the approaches nor the possible modifications that can be engineered.

As used herein the term "PCSK9 activity" includes without being so limited binding of PCSK9 to LDLR, VLDLR, ApoER2, CD81, AnxA2 or a fragment thereof, (e.g., binding of PCSK9 to the R1 domain of AnxA2), translocation of PCSK9 to the cell membrane, enhancement of LDLR, VLDLR, ApoER2, or CD81 degradation and any combination of such activity.

Screening Assays

In an aspect, the present invention concerns a method for identifying a compound for preventing or treating a LDLR-associated disease, a VLDLR-associated disease or an ApoER2-associated disease, said method comprising determining whether:

a) a level of expression of Annexin A2 nucleic acid or encoded polypeptide;
b) a level of Annexin A2 activity; or
c) a combination of a) and b), is increased in the presence of a test compound relative to in the absence of said test compound, wherein said increase is indicative that said test compound can be used for preventing or treating a LDLR-associated disease, a VLDLR-associated disease or an ApoER2-associated disease. This method can be conducted in a cell (e.g., cells expressing PCSK9 and LDLR such as those described in Examples 5 and 6) or in an animal (e.g., appropriate model animal for a LDLR-associated disease, a VLDLR-associated disease, an ApoER2-associated disease).

In another aspect, the present invention concerns determining the likelihood of developing hypercholesterolemia by detecting a genetic variation in an Annexin A2 nucleic acid (see Table 2 above) associated with a reduction of activity in a subject.

In another aspect of the present invention, there is provided a method for identifying a compound for treating a CD81-associated disease said method comprising determining whether: a) a level of expression of Annexin A2 nucleic acid or encoded polypeptide; b) a level of Annexin A2 activity; or c) a combination of a) and b), is decreased in the presence of a test compound (e.g., shRNA directed against AnxA2) relative to in the absence of said test compound, wherein said decrease is indicative that said test compound can be used for preventing or treating a CD81-associated disease (e.g. an HCV infection).

In another aspect, the present invention provides a method for identifying and characterizing a compound specifically targeting the AnxA2 binding domain on PCSK9 for preventing or treating a LDLR-associated disease, a VLDLR-associated disease or an ApoER2-associated disease, said method comprising determining whether a level of PCSK9 activity is decreased in the presence of a compound specifically targeting the AnxA2 binding domain on PCSK9 relative to in the absence of said test compound, wherein said decrease is indicative that said test compound can be used for preventing or treating a LDLR-associated disease, a VLDLR-associated disease or an ApoER2-associated disease. This method can be conducted in vitro (e.g., in PCSK9-AnxA2 binding assay or PCSK9-LDLR binding assay as that described in Example 9), in a cell (e.g., cells as those described in Example 5) or in an animal (e.g., appropriate model animal for a LDLR-associated disease, a VLDLR-associated disease, an ApoER2-associated disease).

In another embodiment of the invention, a reporter assay-based method of selecting agents which modulate Annexin A2 expression or activity is provided. The method includes providing a cell comprising a nucleic acid sequence comprising an Annexin A2 transcriptional regulatory sequence operably-linked to a suitable reporter gene. The cell is then exposed to the agent suspected of affecting Annexin A2 expression (e.g., a test/candidate compound) and the transcription efficiency or Annexin A2 activity is measured by the activity of the reporter gene. The activity can then be compared to the activity of the reporter gene in cells unexposed to the agent in question. Suitable reporter genes include but are not limited to beta($\beta$)-D-galactosidase, luciferase, chloramphenicol acetyltransferase and green fluorescent protein (GFP).

The present invention thus relates to a method of identifying or characterizing a compound for preventing or treating a LDLR-associated disease, a VLDLR-associated disease or an ApoER2-associated disease comprising:
a) contacting a test compound with a cell comprising a first nucleic acid comprising a first transcriptionally regulatory element normally associated with an Annexin A2 gene, operably-linked to a second nucleic acid comprising a reporter gene capable of encoding a reporter protein; and
b) determining whether the reporter gene expression or reporter activity is increased in the presence of the test compound:
wherein an increase in the reporter gene expression or reporter gene activity is indicative that the test compound may be used for treating or preventing or treating a LDLR-associated disease, a VLDLR-associated disease or an ApoER2-associated disease.

The above-noted assays may be applied to a single test compound or to a plurality or "library" of such compounds (e.g., a combinatorial library). Any such compound may be utilized as lead compound and further modified to improve its therapeutic, prophylactic and/or pharmacological properties for instance for the prevention and treatment of an LDLR-associated disease.

Such assay systems may comprise a variety of means to enable and optimize useful assay conditions. Such means may include but are not limited to: suitable buffer solutions, for example, for the control of pH and ionic strength and to provide any necessary components for optimal Annexin A2 activity, expression and stability (e.g. protease inhibitors), temperature control means for optimal Annexin A2 activity, expression and stability, and detection means to enable the detection of the Annexin A2 activity or expression. A variety of such detection means may be used, including but not limited to one or a combination of the following: radiolabelling (e.g., $^{32}P$, $^{14}C$, $^{3}H$), antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/(strept)avidin), and others.

The assay may be carried out in vitro utilizing a source of polypeptide (e.g., Annexin A2, PCSK9 and/or LDLR), which may comprise naturally isolated or recombinantly produced polypeptide (e.g. Annexin A2, PCSK9 and/or LDLR), in preparations ranging from crude to pure. Recombinant polypeptide (e.g., Annexin A2, PCSK9 and/or LDLR) may be produced in a number of prokaryotic or eukaryotic expression systems, which are well known in the art (see for example Martin F. et al., 2001. *Immunogenetics* 53(4): 296-306) for the recombinant expression of the polypeptide (e.g., Annexin A2, PCSK9 and/or LDLR). Such assays may be performed in an array format. In certain embodiments, one or a plurality of the assay steps are automated.

A homolog, variant and/or fragment of Annexin A2 which retains activity and specifically the ability to bind to PCSK9 and inhibit its ability to degrade LDLR (or VLDLR or ApoER2 or CD81) may also be used in the screening methods of the invention. Homologs include protein sequences, which are substantially identical to the amino acid sequence of an Annexin A2 (e.g., SEQ ID NO: 2), sharing significant structural and functional homology with an Annexin A2. Variants include, but are not limited to, proteins or peptides, which differ from an Annexin A2 by any modifications, and/or amino acid substitutions, deletions or additions (e.g., fusion with another polypeptide) while retaining its ability to bind to PCSK9. Subject to the foregoing, modifications can occur anywhere including the polypeptide backbone, (i.e. the amino acid sequence), the amino acid side chains and the amino or carboxy termini. Such substitutions, deletions or additions may involve one or more amino acids. Fragments include a fragment or a portion of an Annexin A2 or a fragment or a portion of a homolog or variant of an Annexin A2 which retains Annexin A2 activity i.e., binds to PCSK9. Such variant include but is not limited to a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E).

"Homology" and "homologous" and "homolog" refer to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to or is a "homolog" of another sequence if the two sequences are substantially identical and the functional activity of the sequences is conserved (as used herein, the term 'homologous' does not infer evolutionary relatedness). Two nucleic acids or amino acid sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%, e.g., with any Annexin A2 (e.g., SEQ ID NO: 2). As used herein, a given percentage of homology between sequences denotes the degree of sequence identity in optimally aligned sequences. An "unrelated" or "non-homologous" sequence shares less than 40% identity, though preferably less than about 25% identity, with an Annexin A2 sequence (e.g., SEQ ID NO: 2).

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%, e.g., with an Annexin A2 sequence (e.g., SEQ ID NO: 2). Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, more preferably highly stringent conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

The assay may in an embodiment be performed using an appropriate host cell comprising Annexin A2 activity and/or the PCSK9 activity. Such a host cell may be prepared by the introduction of DNA encoding Annexin A2 (e.g., comprising the nucleotide sequence set forth in SEQ ID NO: 24, or the coding sequence thereof, or a fragment/variant thereof having Annexin A2 activity) into the host cell and providing conditions for the expression of Annexin A2. Such host cells may be prokaryotic or eukaryotic, bacterial, yeast, amphibian or mammalian.

"Transcriptional regulatory sequence" or "transcriptional regulatory element" as used herein refers to DNA sequences, such as initiation and termination signals, enhancers, and promoters, splicing signals, polyadenylation signals which induce or control transcription of protein coding sequences with which they are operably linked. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since enhancers generally function when separated from the promoters by several kilobases and intronic sequences may be of variable lengths, some polynucleotide elements may be operably-linked but not contiguous. As used herein, a transcriptionally regulatory element "normally" associated with for example an Annexin A2 gene refers to such an element or a functional portion thereof derived from sequences operably-linked to for example an Annexin A2 gene in its naturally-occurring state (i.e., as it occurs in a genome in nature). In another embodiment, the construct may comprise an in frame fusion of a suitable reporter gene within the open reading frame of an Annexin A2 gene. The reporter gene may be chosen as such to facilitate the detection of its expression, e.g. by the detection of the activity of its gene product. Such a reporter construct may be introduced into a suitable system capable of exhibiting a change in the level of expression of the reporter gene in response to exposure a suitable biological sample. Such an assay would also be adaptable to a possible large scale, high-throughput, automated format, and would allow more convenient detection due to the presence of its reporter component.

Expression levels may in general be detected by either detecting mRNA from the cells and/or detecting expression products, such as polypeptides and proteins. Expression of the transcripts and/or proteins encoded by the nucleic acids described herein may be measured by any of a variety of known methods in the art. In general, the nucleic acid sequence of a nucleic acid molecule (e.g., DNA or RNA) in a sample can be detected by any suitable method or technique of measuring or detecting gene sequence or expression. Such methods include, but are not limited to, polymerase chain reaction (PCR), reverse transcriptase-PCR (RT-PCR), in situ PCR, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene.

The term "quantifying" or "quantitating" when used in the context of quantifying transcription levels of a gene can refer to absolute or to relative quantification. Absolute quantification may be accomplished by inclusion of known concentration(s) of one or more target nucleic acids and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, transcription level.

Methods to measure protein expression levels of selected genes of this invention, include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of the protein including but not limited to DNA binding, ligand binding, or interaction with other protein partners.

Methods for normalizing the level of expression of a gene are well known in the art. For example, the expression level of a gene of the present invention can be normalized on the basis of the relative ratio of the mRNA level of this gene to the mRNA level of a housekeeping gene or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the actin gene, ribosomal RNA, 36B4 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include, but are not limited to: Stratagene™ QPCR Human Reference Total RNA, Clontech™ Universal Reference Total RNA, and XpressRef™ Universal Reference Total RNA.

A "reference" or "control" level may be determined, for example, by measuring the level of expression of Annexin A2 nucleic acid or encoded polypeptide, or the level of Annexin A2 activity, in a corresponding biological sample obtained from one or more control subject(s) (e.g., not suffering from a LDLR-associated disease) or known not to be susceptible to a LDLR-associated disease). When such a control level is used, a lower or decreased level measured in a biological sample (i.e. test sample) is indicative for example that the Annexin A2 activator may be useful for treating or preventing an LDLR-associated disease.

As used herein, a substantially similar level refers to a difference in the level of expression or activity between the level determined in a first sample (i.e. test sample) and the reference level which 15% or less; in a further embodiment, 10% or less; in a further embodiment, 5% or less.

As used herein, a "higher" or "increased" level refers to a level of expression or activity in a sample (i.e. test sample) which is at least 20% higher, in an embodiment at least 30% higher, in a further embodiment at least 40% higher; in a further embodiment at least 50% higher, in a further embodiment at least 100% higher (i.e. 2-fold), in a further embodiment at least 200% higher (i.e. 3-fold), in a further embodiment at least 300% higher (i.e. 4-fold), relative to the reference level (e.g., in the absence of an Annexin A2 activator).

Methods of Stratifying Subjects

The methods of classifying or stratifying the subjects of the present invention into subgroups having different phenotypes enables a better characterization of PCSK9-associated diseases such as LDLR-associated diseases and eventually a better selection of treatment depending on the subgroup to which the subject belongs.

In accordance with another aspect of the present invention, there is provided a method of stratifying a subject having a LDLR-associated disease, a VLDLR-associated disease, an ApoER2-associated disease or a CD81-associated disease, the method comprising determining:

a) the Annexin A2 genotype of the subject;
b) a level of expression of Annexin A2 nucleic acid or encoded polypeptide;
c) a level of Annexin A2 activity; or
d) a combination of a), b) and/or c), wherein the results of the measuring step enables the classification of the subject into a subgroup.

In accordance with another aspect of the present invention, the method can also stratify a subject that is likely to develop a LDLR-associated disease, a VLDLR-associated disease, an ApoER2-associated disease or a CD81-associated disease.

In accordance with another aspect of the present invention, the method can also stratify a subject having an underlying disease.

Pharmaceutical Compositions

In one aspect of the present invention the pharmaceutical composition comprising a) a polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) (e.g., derived from human AnxA2 isoform 2 disclosed at FIG. 3E); b) a functional derivative in any presentation form, analogue, conjugate or prodrug of the polypeptide; c) p11; d) an activator of Annexin A2 As used herein the term "Annexin A2 activator" refers to a compound that increases expression (transcription, translation or stability) of Annexin A2 or increases Annexin A2 activity or both (e.g., a demethylation compound (e.g., 5-azacitydine or decitabine)); or e) a combination of any of any of the above is administered prior to the onset of a LDLR-associated disease, a VLDLR-associated disease or an ApoER2-associated disease as a preventive measure. In another aspect of the present invention the pharmaceutical composition of the present invention is administered in combination with a drug or drugs used to treat an underlying disease or condition such as a cardiovascular disease. In a further aspect, the composition of the present invention is administered once the subject has been diagnosed with a LDLR-associated disease, a VLDLR-associated disease or an ApoER2-associated disease. In another embodiment, the composition of the present invention is administered in combination with one or more other drugs used for the prevention and/or treatment of an underlying disease or condition.

By way of example, pharmaceutical compositions of the invention can be in the form of a liquid, solution, suspension, pill, capsule, tablet, gel cap, powder, gel, ointment, cream, nebulae, mist, atomized vapor, aerosol, or phytosome. For oral administration, tablets or capsules can be prepared by conventional means with pharmaceutically acceptable excipients such as binding agents, fillers, lubricants, disintegrants, or wetting agents. The tablets can be coated by methods known in the art. Liquid preparations for oral administration can take the form of, for example, solutions, syrups, or suspension, or they can be presented as a dry product for constitution with saline or other suitable liquid vehicle before use. Preparations for oral administration also can be suitably formulated to give controlled release of the active ingredients.

In addition, pharmaceutical compositions of the invention can contain a pharmaceutically acceptable carrier for administration to a subject, including, without limitation, sterile aqueous, or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. Pharmaceutically acceptable carriers also can include physiologically acceptable aqueous vehicles (e.g., physiological saline) or other known carriers appropriate to specific routes of administration.

An "effective amount" refers to an amount effective, at dosages and for periods of time necessary, to achieve the desired prophylactic and/or therapeutic result (e.g., prevention and/or treatment of a PCSK9-associated disease). An effective amount of a compound of the invention may vary according to factors such as the disease state, age, sex, and weight of the individual, and the ability of the compound to elicit a desired response in the individual. Dosage regimens may be adjusted to provide the optimum therapeutic response. An effective amount is also one in which any toxic or detrimental effects of the compound are outweighed by the therapeutically beneficial effects. For any particular subject, specific dosage regimens may be adjusted over time according to the individual need and the professional judgment of the person administering or supervising the administration of the compositions.

Kits

The present invention also relates to kits for preventing or treating a LDLR-associated disease, a VLDLR-associated disease, an ApoER2-associated disease or a CD81-associated disease comprising a nucleic acid, a protein or a ligand in accordance with the present invention. For instance it may comprise a composition of the present invention or a vector encoding same, and instructions to administer said composition or vector to a subject to preventing or treating a phenotype of the disease. Such kits may further comprise at least one other active agent able to preventing or treating a LDLR-associated disease, a VLDLR-associated disease, an ApoER2-associated disease or a CD81-associated disease. When the kit is used to prevent or treat a hypercholesterolemia phenotype in a subject having same or having an underlying disease, the kit may also further comprise at least one other active agent capable of preventing or treating hypercholesterolemia such as a cholesterol synthesis inhibitor (e.g., statin, ezetimibe) or inhibitor of PCSK9/LDLR binding (e.g., berberin or fibrates) or of the underlying disease. In addition, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another.

The present invention is illustrated in further details by the following non-limiting examples.

EXAMPLE 1

Material and Methods

Expression Constructs

Human PCSK9 and mutant cDNAs and domains thereof were cloned, with or without a C-terminal V5 tag, into pIRES2-EGFP vector (Clonetech) as previously described[1,4,23]. The cDNAs coding for mouse PC5A-V5[24] and pCi-hLDLR[4], were previously reported. The cDNA encoding for p11-YFP was kindly provided by Dr Volker Gerke (Institute of Medical Biochemistry, University of Muenster, Germany). Wild type human Annexin A2 (AnxA2) isoform 2 (ATCC #MGC-2257) and Annexin A1 (AnxA1) (ATCC #MGC-5095) were purchased from ATCC and subcloned into NheI/SacI digested pIRES2-EGFP vector. An HA epitope (YPY-DVPDYA) was fused by PCR mutagenesis at the C-terminus of both AnxA1 and AnxA2. All oligonucleotides used in the various AnxA2 constructions are listed in Table 3 below. Two-steps PCRs were performed on AnxA2 cDNA to introduce point mutations ($_{77}$RRTKK (SEQ ID NO: 26)>AATAK (SEQ ID NO: 27); $_{77}$RRTKK(SEQ ID NO: 26)>AATAA (SEQ ID NO: 28); $_{77}$RRTKKELASALK(SEQ ID NO: 29)>$_{77}$AATAAELASALA(SEQ ID NO: 30); $_{80}$KKEL A(SEQ ID NO: 31)>GKPLD(SEQ ID NO: 32)), or amino acid (aa) deletions (Δ2-24, aa 2-24; ΔR1, aa 37-108; ΔR2, aa 109-192; ΔR3, aa 193-268; ΔR4, aa 269-339) into pIRES2-AnxA2-EGFP vector (see Table 3 below). In addition, using PCR, the AnxA2 segment aa 49-75 was swapped with the corresponding AnxA1 segment aa 58-84 [AnxA2 (aa 49-75)>AnxA1 (aa 58-84)]. Purified PCR fragments were digested with the appropriate restriction enzymes and subcloned into the corresponding digested pIRES2-AnxA2-HA-EGFP vector. All final cDNA constructs were verified by DNA sequencing.

TABLE 3

| \multicolumn{3}{c}{Oligonucleotides used for site-directed mutagenesis of AnxA2 and its mutants} |
|---|---|---|
| Mutants | Sense (S) | Antisense (AS) |
| Δ2-24 | 5'-CGCTAGCCACCATGGGGTCTGTCAAAGCCTATAC-3' (SEQ ID NO: 33) | 5'-GAGCAGGTGTCTTCAATAGG-3' (SEQ ID NO: 34) |
| Δ37-108 (R1) | 5'-GATGCTGAGTATGACGCTTCTGAGCTAAAAG-3' (SEQ ID NO: 35) | 5'-GAAGCGTCATACTCAGCATCAAAG TTAGTATAGGC-3' (SEQ ID NO: 36) |
| Δ109-192 (R2) | 5'-CCTGCTCAGCAAGATGCTCGGGATCTC-3' (SEQ ID NO: 37) | 5'-CGAGCATCTTGCTGAGCAGGTGTC TTCAATAAG-3' (SEQ ID NO: 38) |
| Δ193-268 (R3) | 5'-GATTATGAACTGATTGACTATTTTGCTGATCGGCT GTATG-3' (SEQ ID NO: 39) | 5'-GCAAAATAGTCAATCAGTTCATAA TCAATGACAG-3' (SEQ ID NO: 40) |
| Δ269-339 (R4) | 5'-GCCCCTGACCGGTTACCCATACGATG-3' (SEQ ID NO: 41) | 5'-GTATGGGTAACCGGTCAGGGGCTT GTTCTGAATG-3' (SEQ ID NO: 42) |
| Δ25-36 | 5'-CCAAGTGCATATCGGGATGCTTTGAACATTGAAA C-3' (SEQ ID NO: 43) | 5'-CATCCCGATATGCACTTGGGGGTG T-3' (SEQ ID NO: 44) |
| Δ37-66 | 5'-GATGCTGAGCAGAGACAGGATATTGCCTTC-3' (SEQ ID NO: 45) | 5'-CCTGTCTCTGCTCAGCATCAAAGTTAG TATAGGC-3' (SEQ ID NO: 46) |
| Δ74-88 | 5'-GCCTTCTCAGCCTTATCTGGCCAC-3' (SEQ ID NO: 47) | 5'-CCAGATAAGGCTGAGAAGGCAATATCC TGTCTC-3' (SEQ ID NO: 48) |
| Δ37-48 | 5'-GATGCTGAGAAAGGTGTGGATGAGGTCAC-3' (SEQ ID NO: 49) | 5'-CCACACCTTTCTCAGCATCAAAGTTAG TATAGGC-3' (SEQ ID NO: 50) |
| Δ49-61 | 5'-CATCAAGACCAACCGCAGCAATGCAC-3' (SEQ ID NO: 51) | 5'-CTGCGGTTGGTCTTGATGGCTGTTTCA ATG-3' (SEQ ID NO: 52) |
| Δ62-75 | 5'-CAACATTTTGACCAGAAGGACCAAAAAGGAACTTG C-3' (SEQ ID NO: 53) | 5'-GGTCCTTCTGGTCAAAATGTTGACAAT GGTG-3' (SEQ ID NO: 54) |
| Δ82-88 | 5'-GAAGGACCAAAAAGTCAGCCTTATCTGGCCAC-3' (SEQ ID NO: 55) | 5'-GATAAGGCTGACTTTTTGGTCCTTCTC TGGTAGG-3' (SEQ ID NO: 56) |
| Δ89-101 | 5'-CAGCACTGAAGCTATTGAAGACACCTGCTCAG-3' (SEQ ID NO: 57) | 5'-GTCTTCAATAGCTTCAGTGCTGATGCA AGTTC-3' (SEQ ID NO: 58) |
| Δ102-108 | 5'-GATTTTGGGCTATGACGCTTCTGAGCTAAAAG-3' (SEQ ID NO: 59) | 5'-GAAGCGTCATAGCCCAAAATCACCGTC TC-3' (SEQ ID NO: 60) |
| K28S + D34N + E36S | 5'-TCAGCCTATACTAACTTTAATGCTTCGCGGGATGCTT TG-AACATTG-3' (SEQ ID NO: 61) | 5'-CGAAGCATTAAAGTTAGTATAGGCTGA GACAGACCCATATGCA-CTTG-3' (SEQ ID NO: 62) |

TABLE 3-continued

Oligonucleotides used for site-directed mutagenesis of AnxA2 and its mutants

| Mutants | Sense (S) | Antisense (AS) |
|---|---|---|
| R37S + E43H + K47M | 5'-CGGATGCTTTGAACATTCACACAGCCATCATGACCAAA-GGTGTGGATGAG-3' (SEQ ID NO: 63) | 5'-CATGATGGCTGTGTGAATGTTCAAAGCATCCGACTCAGCA-TCAAAGTTAGTATAGGC-3' (SEQ ID NO: 64) |
| 80KKELA (SEQ ID NO: 31) > GKPLD (SEQ ID NO: 32) | 5'-GGAAAGCCACTTGATTCAGCACTGAAGTCAGCC-3' (SEQ ID NO: 65) | 5'-GCTGAATCAAGTGGCTTTCCGGTCCTTCTCTGGTAGGC-3' (SEQ ID NO: 66) |
| 77RRTKK (SEQ ID NO: 26) > AATAK (SEQ ID NO: 27) | 5'-GCAGCGACCGCAAAGGAACTTGCATCAGCACTG-3' (SEQ ID NO: 67) | 5'-CTTTGCGGTCGCTGCCTGGTAGGCGAAGGCAATATC-3' (SEQ ID NO: 68) |
| 77RRTKK (SEQ ID NO: 26) > AATAA (SEQ ID NO: 28) | 5'-CGACCGCAGCGGAACTTGCATC-3' (SEQ ID NO: 69) | 5'-GATGCAAGTTCCGCTGCGGTCG-3' (SEQ ID NO: 70) |
| 77RRTKKELASALK (SEQ ID NO: 29) > 77AATAAELASALA (SEQ ID NO: 30) | 5'-CATCAGCACTGGCGTCAGCCTTATC-3' (SEQ ID NO: 71) | 5'-GATAAGGCTGACGCCAGTGCTGATG-3' (SEQ ID NO: 72) |
| SW25-27 (A1- > A2) | 5'-CTACACCCCCAAGTGCATATAGCGCTGTC-3' (SEQ ID NO: 73) | 5'-GACAGCGCTATATGCACTTGGGGGTGTAG-3' (SEQ ID NO: 74) |
| SW28-30 (A1- > A2) | 5'-GGGTCTGTCAGTCCCTATACTAACTTTG-3' (SEQ ID NO: 75) | 5'-CAAAGTTAGTATAGGGACTGACAGACCC-3' (SEQ ID NO: 76) |
| SW31-33 (A1- > A2) | 5'-GTCAAAGCCTATCCTACCTTTGATGCTGAG-3' (SEQ ID NO: 77) | 5'-CTCAGCATCAAAGGTAGGATAGGCTTTGAC-3' (SEQ ID NO: 78) |
| SW34-36 (A1- > A2) | 5'-CTATACTAACTTTAATCCTAGTCGGGATGCTTTG-3' (SEQ ID NO: 79) | 5'-CAAAGCATCCCGACTAGGATTAAAGTTAGTATAG-3' (SEQ ID NO: 80) |
| SW37-39 (A1- > A2) | 5'-CTTTGATGCTGAGAGCGATGTTTTGAACATTG-3' (SEQ ID NO: 81) | 5'-CAATGTTCAAAACATCGCTCTCAGCATCAAAG-3' (SEQ ID NO: 82) |
| SW40-42 (A1- > A2) | 5'-CGGGATGCTGCGGCCCTTGAAACAGCCATC-3' (SEQ ID NO: 83) | 5'-GATGGCTGTTTCAAGGGCCGCAGCATCCCG-3' (SEQ ID NO: 84) |
| SW43-45 (A1- > A2) | 5'-CTTTGAACATTCACAAAGCCATCAAGACC-3' (SEQ ID NO: 85) | 5'-GGTCTTGATGGCTTTGTGAATGTTCAAAG-3' (SEQ ID NO: 86) |
| SW46-48 (A1- > A2) | 5'-GAAACAGCCATCATGGTCAAAGGTGTGG-3' (SEQ ID NO: 87) | 5'-CCACACCTTTGACCATGATGGCTGTTTC-3' (SEQ ID NO: 88) |
| SW49-75 (A1- > A2) AnxA2 (aa49-75) > AnxA1 (aa58-84) | (1) 5'-GCCACCATTATCGACATTTTGACCAAACGCAGCAATGCACAGAG-3' (SEQ ID NO: 89) (2) 5'-AACAATGCACAGAGACAGCAAATTAAAGCCGCCTACCAGAGAAGGACCAAAAAGGAACTTG-3' (SEQ ID NO: 91) | (1) 5'-TTTGGTCAAAATGTCGATAATGGTGGCCTCATCCACACCTTTGGTCTTG-3' (SEQ ID NO: 90) (2) 5'-CTGGTAGGCGGCTTTAATTTGCTGTCTCTGTGCATTGTTGCGTTTGGTCAAAATGTCG-3' (SEQ ID NO: 92) |
| SW49-61 (A1- > A2) | 5'-GGCCACCATTATCGACATTTTGACCAACCGCAGCAATGC-ACAGAG-3' (SEQ ID NO: 93) | 5'-CAAAATGTCGATAATGGTGGCCTCATCCACACCTTTGGTC-3' (SEQ ID NO: 94) |

TABLE 3-continued

Oligonucleotides used for site-directed mutagenesis of AnxA2 and its mutants

| Mutants | Sense (S) | Antisense (AS) |
|---|---|---|
| SW62-75 (A1- > A2) | 5'-AAACGCAACAATGCACAGAGACAGCAGATTAAGGCCGCCTACCAGAGAAGGACC-3' (SEQ ID NO: 95) | 5'-GGCCTTAATCTGCTGTCTCTGTGCATTGTTGCGTTTGGT-CAAAATGTTGACAATGGTG-3' (SEQ ID NO: 96) |
| SP-R1(30-108)-HA | (1) 5'-GGGCGGTAGGCGTGTACGGTGG-3' (SEQ ID NO: 97) (2) 5'-CGCCCGTGCGTATACTAACTTTGATGCTGAGC-3' (SEQ ID NO: 99) | (1) 5'-CAAAGTTAGTATACGCACGGGCGCCC-3' (SEQ ID NO: 98) (2) 5'-GGGTAACCGGTCTGAGCAGGTGTCTTCAATAGG-3' (SEQ ID NO: 100) |
| SP-R1(N62Q)-HA | 5'-CATTTTGACCCAACGCAGCAATG-3' (SEQ ID NO: 101) | 5'-CATTGCTGCGTTGGGTCAAAATG-3' (SEQ ID NO: 102) |
| SP-R1(S64A)-HA | 5'-CCAACCGCGCCAATGCACAGAGAC-3' (SEQ ID NO: 103) | 5'-GTCTCTGTGCATTGGCGCGGTTGG-3' (SEQ ID NO: 104) |

RNA Interference

To silence human AnxA2, a 29mer pRS-shRNA was used: (sh3, GCATCAGCACTGAAGTCAGCCTTATCTGG (SEQ ID NO: 105)) (Origene). The control pRS-shGFP vector [shCtl] contained a non-effective 29mer shGFP cassette.

Quantitative RT-PCR

Quantitative PCR (qPCR) analysis of RNA preparations was performed as previously described[11,25]. Briefly, each cDNA sample was submitted to 2 polymerase chain reaction (PCR) amplifications: one for normalizing ribosomal-protein gene (S14 for human and S16 for mouse cDNAs) and the other for the gene of interest, each in triplicate. The Mx3500P system from Stratagene was used to perform and analyze the qPCR reactions, using S14 or S16 amplifications as normalizers[25]

Cell Culture and Transfections

HepG2, HuH7, COS-1, BSC40 and HEK293 cell were grown in Dulbecco's modified Eagle's medium (DMEM) with 10% fetal bovine serum (FBS; Gibco), whereas CHO-K1 and CHO-K1 mutant Pgsd-677 cells that lack heparan sulfate proteoglycans[26] were grown in Ham's F12:DMEM (50:50) media with 10% FBS. Y1 mouse adrenal cells were grown in F12K medium with 15% horse serum and 2.5% FBS. All cells were maintained at 37° C. under 5% $CO_2$. At 80-90% confluence, HuH7 and CHO-K1 cells were transiently transfected with Lipofectamine™ 2000 (Invitrogen), HEK293 cells were transfected with Effectene™ (Qiagen) and HepG2 cells were transfected with Fugene™ HD (Roche). Twenty-four hours after transfection cells were washed and incubated in serum-free medium, containing or not exogenous conditioned media and/or purified proteins, as indicated in figure legends, for an additional 20 h before media collection and cell lysis. For analysis of the various AnxA2 mutants in HEK293 cells, 24 h post-transfection, the cells were washed and then incubated for another 24 h in complete medium containing 50 μM of the proteasome inhibitor ALLN (Calbiochem). Stable transfectants of shRNA-AnxA2 were obtained in HuH7 cells following puromycin selection.

Antibodies and Purified Proteins

The rabbit polyclonal antibody against PCSK9 was raised in-house as described[15]. Other antibodies used were a rabbit polyclonal V5-antibody (Sigma), an unconjugated or horseradish peroxidase (HRP)-conjugated mouse monoclonal anti-V5 (mAb:V5 or mAb:V5-HRP, Invitrogen), goat anti-LDLR (human) (R&D Systems), HRP-conjugated mouse anti-His (Qiagen) and anti-HA (Roche Diagnostics), monoclonal anti-HA-Alexa Fluor 488 (Invitrogen) and mouse anti-AnxA2 (human) (BD Biosciences). Purified CHRD-His was produced in-house, purified PCSK9-$(His)_6$ was a kind gift from Bristol-Myers Squibb, purified AnxA2-$(His)_6$ and AnxA1-$(His)_6$ were purchased from EMD biosciences.

Cell Lysis and Subcellular Fractionation

Mouse tissues and cells were lysed in ice cold radioimmune precipitation assay (RIPA) buffer (50 mM Tris-HCl pH 7.8, 150 mM NaCl, 1% Nonidet P-40, 0.5% sodium deoxycholate, 0.1% SDS) containing a cocktail of protease inhibitors (Roche Diagnostics). For crude membrane preparations and subcellular fractionation COS-1 cells were homogenized in 10 mM Tris-HCl, pH 7.4, 1 mM EDTA, 200 mM sucrose and a protease inhibitor cocktail. The homogenate was centrifuged at 720×g for 10 min at 4° C. to remove nuclei and cell debris. The resulting supernatant S1 was centrifuged at 15,000×g for 10 min at 4° C. The pellet P1, containing organelles such as lysosomes and mitochondria, was solubilized in RIPA buffer and the supernatant S2 was centrifuged at 100,000×g for 75 min at 4° C. (SW40 rotor, Beckman ultracentrifuge). The resulting crude P2 cell membrane pellet was solubilized in RIPA and the soluble supernatant S3 was kept for Far Western blot analysis. Quantitation of protein concentration was effected by the Bradford protein assay. The supernatant S3 (3 μg protein) was analyzed by SDS-PAGE and compared to 30 μg protein loads from other subcellular fractions.

Far Western Blot Assays

Lysates (20 to 30 μg protein), media or purified AnxA2-$(His)_6$ were heated in reducing or non-reducing Laemmli sample buffer, resolved by SDS-PAGE on 8% glycine gels and electro-transferred onto nitrocellulose membranes (GE Healthcare). Following 1 h incubation in 5% skim milk in Tris-Buffered Saline-0.1% Tween (TBST), membranes where incubated with conditioned media of CHO-K1 cells overexpressing either an empty vector (pIRES-V5), PC5A-V5, CHRD-V5, pIRES-D374Y, PCSK9-V5 or its V5-tagged mutants, or incubated with purified AnxA2-$(His)_6$ for 3 h at room temperature. Membranes were then washed in TBST and incubated with the HRP-conjugated anti-V5 or anti-His antibodies and revealed by enhanced chemiluminescence (GE Healthcare). For competition experiments, 10 µg of His-tagged PCSK9 or CHRD were added to the PCSK9-V5 media before Far Western blotting. For PCSK9 binding requirements with the ~33 kDa protein, 1M NaCl, 10 mg/ml heparin, 1M NaCl+10 mg/ml heparin, or 100 mM EDTA were added to the PCSK9-V5 conditioned media used for Far Western blotting.

Immunoprecipitation and Western Blot Assays

For immunoprecipitation cell lysates were incubated overnight at 4° C. with anti-V5-agarose beads (Sigma) and washed 5 times with cold lysis buffer. Following addition of reducing Laemmli sample buffer bound proteins were revealed by Western blot or separated by SDS-PAGE (8%) and stained by Coomassie blue for band excision and mass spectrometry. As control for the immunoprecipitation, antigens complexed with the anti-V5-agarose beads were eluted with the V5 peptide (50 µM, Sigma), separated by SDS-PAGE (8%) and revealed by Western blotting with the anti-V5-HRP antibody.

Western blotting experiments were made on samples that were reduced in Laemmli buffer, heated and resolved on 8% glycine SDS-PAGE gels. Separated proteins were then electro-transferred onto nitrocellulose, and probed with HRP-conjugated anti-V5 or anti-HA tags or with primary antibodies. Bound primary antibodies were detected with corresponding species-specific HRP-labeled secondary antibodies and revealed by enhanced chemiluminescence. Quantitation of band intensity was done with the ImageJ™ software version 1.37 (Wayne Rasband, National Institutes of Health, Bethesda, Md.).

2D Gel Electrophoresis and Mass Spectrometry 2D gel electrophoresis was performed according to protocols previously described ([27] and GE Healthcare (2D electrophoresis handbook, 2004)). COS-1 cells were lysed in 7 M urea, 2 M thiourea, 2% CHAPS (3-[(3-Cholamidopropyl) dimethylammonio]-1-propanesulfonate), 0.5% immobilized pH gradient (IPG) buffer (carrier ampholyte mixture) (GE Healthcare) and 0.002% bromophenol blue. Protein concentration was estimated by the Bradford assay and adjusted to 0.6 µg/ml with the lysis buffer. 40 mM dithiothreitol was then added and cell lysates were kept rotating at 4° C. for 60 minutes. Samples (200 µl) were loaded onto broad-pH-range (pH 3-10) IPG gel strips (GE Healthcare) and the first-dimension isoelectric focusing separation was achieved using an Ettan IPGphor™ II system (GE Healthcare). For the second-dimension SDS-PAGE separation, IPG strips were equilibrated 15 min in the SDS equilibration buffer (6M urea, 75 mM Tris-HCl pH 8.8, 29.3% glycerol, 2% SDS, 0.002% bromophenol blue) containing 10 mg/ml dithiothreitol and an additional 15 minutes in the SDS equilibration buffer containing 25 mg/ml iodoacetamide and applied to 12% SDS gels. Gels were then either stained in Coomassie blue or transferred on nitrocellulose and processed for Far Western blotting with PCSK9-V5. The signal obtained at ~33 kDa in the Far Western blot was used to establish the position of the band to be excised for mass spectrometry analysis.

For protein identification by LC/MS/MS, the bands or spots of interest were cut out from the gel and digested with trypsin (0.1 µg) for 60 min at 58° C. Peptides were extracted from the gel at room temperature, and the supernatants were transferred into a 96-well plate and then completely dried in a vacuum centrifuge. Before the analysis, peptides were dissolved under agitation for 15 min in 13 µl of formic acid 0.1%, then sonicated for 5 min, and centrifuged at 2,000 rpm for 1 min. Analysis of the peptide mixture was done by liquid chromatography-mass spectrometry (LC/MS/MS) using a LTQ Orbitrap™ mass spectrometer configured with an on-line NanoLC-2D™ HPLC system (Eksigent, Dublin, Calif.). Protein identification was obtained from the MS/MS spectra using Mascot™ analysis software (Matrix Science).

Hexa-His Pull-Down Assay

20 µg of purified AnxA2-(His)$_6$ or AnxA1-(His)$_6$ or no proteins (for negative control) were immobilized onto a cobalt chelate resin (Thermo Scientific). The resin was then washed several times with 40 mM immidazole and incubated overnight at 4° C. with 800 µl of conditioned media from PCSK9-V5-transfected CHO-K1 cells containing 40 mM immidazole. The resin was then washed several times with immidazole (40 mM), heated in reducing Laemmli sample buffer and centrifuged. Supernatants were analyzed by Western blot as described above using the anti-V5-HRP or anti-His-HRP antibodies.

Immunocytochemistry

For immuno-cytochemistry, cells were plated on glass bottom culture dishes (MatTek) and then transfected the following day. Twenty-four hours post-transfection, the cells were washed with DMEM, incubated for an additional 20 h without serum and then washed 3 times with PBS. Cell surface labelings were made under non-permeabilizing conditions by fixation with 3.7% formaldehyde for 10 min at room temperature. Cells were then washed in PBS, incubated for 5 min in 150 mM glycine, washed once in PBS and incubated for 30 min in 1% bovine serum albumin in PBS. Cells were incubated overnight at 4° C. with primary antibodies and then washed 4× with PBS. Antigen-antibody complexes were revealed by incubation for 45 min at room temperature with corresponding species-specific Alexa fluor (488, 555 or 647)-tagged secondary antibodies (Invitrogen). After several washes in PBS, cells were covered with 5% 1,4-diazabicyclo [2.2.2]octane (Sigma) in PBS/glycerol 90% and immunofluorescence analyses were performed with a Zeiss LSM-510 confocal microscope.

EXAMPLE 2

PCSK9 Binds to a ~33 kDa Protein

FIG. 2A schematically summarizes the various constructs[15] used below. Nitrocellulose blots of various cell line extracts were incubated with the conditioned medium of CHO-K1 cells overexpressing PCSK9-V5 (FIG. 2B). Following washes, incubation with an anti-V5 mAb revealed a ~33 kDa protein interacting with native PCSK9-V5, especially in COS-1, BSC40 and HuH7 cell lysates (FIG. 2B, middle panels). As controls, the conditioned media of CHO-K1 cells transfected with either an empty pIRES-V5-EGFP vector or another secreted proprotein convertase PC5A-V5[26] was shown not to reveal any interacting protein (FIG. 2B, left panels). This suggests that the denatured ~33 kDa protein specifically binds native PCSK9. Subcellular fractionation of COS-1 cells revealed that although the ~33 kDa binding protein is associated with membranes (15,000×g and 100,000×g pellets), it is ~10× more abundant in the soluble 100,000×g supernatant (FIG. 2B, middle-right panel, and legend). Using the same approach, mouse tissue extracts revealed that a similar ~33 kDa PCSK9 interactor is found mostly in the small intestine, including ileum and jejunum, but is less abundant in liver, adrenals and kidney (see large arrow in FIG. 2B, right panel). Note that in liver, the major interacting protein migrates with an apparent molecular mass of ~45 kDa (small arrow FIG. 2B, right panel).

To identify the PCSK9 interacting domain, COS-1 cell extracts were incubated with various PCSK9 constructs (FIGS. 2A,C). The data showed that the interacting domain of PCSK9 is its C-terminal CHRD, since a construct lacking it (PCSK9-L455X-V5) does not bind to the ~33 kDa protein, while the CHRD alone binds at least 3-fold better than the full length PCSK9 (FIG. 2C, left panels), and effectively competes for this interaction with the full length protein (FIG. 2D). Accordingly, constructs still containing the CHRD, such as those resulting in the Turin cleaved PCSK9 form (aa 219-692 designated RRRREL-V5 on FIG. 2C), or the uncleavable R218S[23], the non-Tyr sulfated form (Y38F) (1), or the mutant D374Y that strongly binds the LDLR[18], still interact with the ~33 kDa protein (FIG. 2C). While 100 mM EDTA ($Ca^{2-}$ chelator) and 10 mg/ml heparin do not affect the PCSK9's ability to bind the ~33 kDa protein, incubation in the presence of 1M NaCl decreased the binding by ~70%, suggesting that charges are not the only determinants (FIG. 2E). Finally, it was observed that that heparin actually enhances the binding. Heparin could induce a conformational change, in either AnxA2 or PCSK9 or both, and allow stronger interactions and its presence largely prevents the effect of NaCl (FIG. 2E). Heparin stabilize or allow a stronger interaction and 1M NaCl is not sufficient to disrupt binding.

EXAMPLE 3

The ~33 kDa PCSK9 Partner is Annexin A2

In order to identify the PCSK9 interactor, either an empty vector (pIRES-V5) or PCSK9-V5 were overexpressed in COS-1 cells. Cell extracts were then immunoprecipitated with anti V5-coupled agarose beads, followed by SDS-PAGE separation and mass spectrometry analysis of the protein(s) migrating at ~33 kDa (FIG. 3A; boxed areas). The efficacy of the immunoprecipitation control is shown in FIG. 3B. The mass spectrometric data (not shown) revealed that the ~33 kDa protein is monkey Annexin A2 (AnxA2; XP_001155637), which exhibits 99% protein sequence identity to human AnxA2 (AAH09564). Furthermore, this interacting protein is found in the PCSK9-V5 overexpressing cells but not in control cells, suggesting that AnxA2 is the sought PCSK9 interactor.

In order to further substantiate the nature of the ~33 kDa interactor, 120 μg proteins obtained from 1×10[6] COS-1 cells by 2D [SDS-PAGE]-[Isoelectric focusing] were resolved. Proteins separated by 2D gels were either stained with Coomassie blue (FIG. 3C) or transferred to nitrocellulose and processed for Far Western blotting with PCSK9-V5 (FIG. 3D). The signal obtained coinciding with a ~33 kDa/pl 7.5 protein in the far Western blot (FIG. 3D) was used to localize the exact position of the band to be excised for mass spectrometric analysis (FIG. 3C, boxed area) using tandem MS/MS. Protein database search using Mascot™ analysis (Matrix Science) revealed ~77% tryptic peptide coverage with a total Mascot™ score of 2540, corresponding to human AnxA2. The mass spectral data (FIG. 3E) clearly confirmed that AnxA2 is the major PCSK9-interactor identified following co-immunoprecipitation with PCSK9-V5 in COS-1 cell lysates (FIG. 3A).

EXAMPLE 4

Specificity of the Interaction of Native PCSK9 with AnxA2

To confirm that the interaction seen in COS-1 cell extracts can be reproduced by overexpression of AnxA2 in cells that do not substantially express this protein, human AnxA2 or, as control, human AnxA1 were overexpressed in CHO cells. Far Western blot analysis confirmed that PCSK9 specifically binds AnxA2, but not the closely related (~53% protein sequence identity) family member AnxA1 (FIG. 4A). This is further confirmed by pull-down assays whereupon immobilized native AnxA2-$(His)_6$ bound PCSK9 and its furin cleaved form (PCSK9-Δ218)[23], while AnxA1-$(His)_6$ does not (FIG. 4B).

Co-immunoprecipitation of PCSK9-V5 and HA-tagged AnxA2 (AnxA2-HA), but not AnxA1, was demonstrated following their co-expression in CHO-K1 cells (FIG. 4C). Interestingly, the cellular partner of AnxA2, known as p11[28], did not interfere with the PCSK9-AnxA2 co-immunoprecipitation (FIG. 4C), suggesting that PCSK9 could bind the physiologically observed tetrameric cell surface complex of $(p11)_2$-$(AnxA2)_2$[28]. Native PCSK9 binds in a dose-dependant manner purified AnxA2 and its dimer under both reducing and non-reducing conditions (FIG. 4D, left panel), suggesting that no critical disulfide bond(s) in AnxA2 is needed for this interaction. This data agrees with the interaction observed in the 2D-Far Western analysis performed following iodoacetamide treatment of cell extracts (FIG. 3D). Iodoacetamide blocks cysteines so that the observed interaction does not result from a non specific disulfide bridge. Finally, AnxA2 binds only native PCSK9 or its CHRD, but not their SDS-PAGE denatured forms (FIG. 4E). Thus, the structural integrity of PCSK9 and its CHRD is important for the interaction.

The CHRD mutation Q554E in PCSK9 leads to lower levels of LDL cholesterol[29] indicating a loss-of-function of PCSK9 towards LDLR degradation. Far Western blots of extracts from COS-1, CHO-K1 or AnxA2-transfected CHO-K1 cells with PCSK9-V5 or its mutant Q554E-V5 (FIG. 5A) demonstrated that the latter's binding to AnxA2 was ~3 fold higher than that of wild type PCSK9 (FIG. 5B). The CHRD is composed of 6 β-strand structures repeated 3-times and hence forming 3-subdomain modules M1, M2 and M3 (21). The $Gln^{554}$ residue is in an exposed loop within the CHRD and is unique to the second subdomain module M2 (21). M1 could increase the binding of AnxA2 to M2.

AnxA2 is known to be a cytosolic and a membrane-associated protein through phospholipid binding. It is also known to translocate to the cell surface and to associate with diverse extracellular proteins[30,31]. To determine if the interaction of PCSK9 with AnxA2 occurs at the external layer of the cell surface, PCSK9-V5 and AnxA2-HA transfected CHO-K1 cells were fixed under non-permeabilizing conditions and labeled with the anti-V5 and anti-HA tag antibodies. Immunofluorescence staining demonstrated a partial co-localization of PCSK9 with AnxA2 at the plasma membrane of CHO-K1 cells (FIG. 6), supporting their co-immunoprecipitation and interaction in a cellular context.

EXAMPLE 5

AnxA2 Inhibits the PCSK9-Enhanced LDLR Degradation

The effect of the PCSK9-AnxA2 interaction on the LDLR-lowering function of PCSK9[3,32] was first tested by overexpressing PCSK9, with or without AnxA2, in CHO-K1 cells. While the LDLR level was reduced by ~30% in PCSK9-transfected cells, its level returned to that of the control pIRES-transfected cells when PCSK9 was co-transfected with AnxA2 (FIG. 7A). Furthermore, the transfection of HepG2 cells (endogenously expressing PCSK9, but not AnxA2) with AnxA2 alone increased the LDLR level by ~40% and by to ~90% when AnxA2 was co-transfected with its accessory protein p11 (FIG. 7B).

To determine if the PCSK9-AnxA2 interaction can inhibit the PCSK9-induced LDLR degradation from the extracellular milieu, HepG2 cells were incubated for ~20 h with conditioned media from PCSK9-transfected CHO-K1 cells with or without the exogenous addition of 5 ug/ml of purified AnxA2-(His)$_6$. Western blot of HepG2 cell lysates showed that the addition of exogenous AnxA2 reduced the ability of PCSK9 to enhance LDLR degradation (from ~30% to ~10%; FIG. 7C). Note that the addition of exogenous AnxA2 to non-transfected cells also increased the level of LDLR, likely due to its effect on endogenous PCSK9 in HepG2 cells (FIG. 7C, left panel).

Finally, addition of 1 µg of purified PCSK9 to CHO-K1 cells overexpressing the LDLR at 4° C. (preventing internalization) resulted in a visible cell surface localization of PCSK9 (FIG. 7D), and the latter was reduced by further addition of either 5 or even more so 20 µg purified AnxA2 (FIGS. 7E,F). Therefore, it was deduced that because of its interaction with the CHRD AnxA2 reduces the level of cell surface PCSK9 likely bound to the LDLR. Without being bound by this hypothesis, PCSK9's reduced binding to LDLR induces a more rapid internalization of PCSK9 into the cell.

The effect of the PCSK9-AnxA2 interaction on the LDLR-lowering function of PCSK9 was also analyzed by immunofluorescence under non-permeabilizing conditions, to overcome problems associated with the low transfection efficiency of HepG2 cells and subsequent detection of small changes in total protein levels by Western blot. Expression of AnxA2 alone or together with p11 led to a strong increase in labelling intensity of cell surface LDLR (FIGS. 8 B,C) compared to control pIRES-transfected cells (FIG. 8A). Overexpression of PCSK9 in HepG2 cells appreciably reduced the levels of cell surface LDLR, as compared to control (compare FIGS. 8A to D). Finally, expression of AnxA2 with either WT-PCSK9 or the gain of function mutant PCSK9-D374Y (FIG. 8F, inset) prevented their LDLR-lowering effect (FIGS. 8E-F).

EXAMPLE 6 shRNA Knockdown of AnxA2 Enhances LDLR Degradation in HuH7 Cells

Stable (FIG. 9A) or transient (FIG. 9B) transfection of HuH7 cells with either an AnxA2-shRNA or a control one resulted in a ~60-70% knockdown of AnxA2, as compared to control, and a reduction of ~40-70% of the LDLR levels (FIGS. 9A,B). These data support the notion that in HuH7 cells endogenous AnxA2 can inhibit the PCSK9-enhanced degradation of the LDLR. HEK293 cells (expressing negligible amounts of PCSK9 mRNA, as compared to either HepG2 or HuH7 cells (FIG. 14) were transfected with AnxA2 or AnxA1 cDNAs with or without p11 (FIG. 9C) or with shRNAs (FIG. 9D). None of these treatments affected the levels of endogenous LDLR in HEK293 cells. This result substantiates the specific relation between AnxA2 and PCSK9 in LDLR regulation.

Finally, transient transfection of HuH7 cells with the AnxA2-shRNA revealed that cells still expressing high levels of AnxA2 also show elevated immunoreactivity to LDLR, whereas the reverse is true in cells lacking AnxA2 (FIG. 9E, dotted line), likely due to shRNA downregulation of AnxA2. This representative result was observed over many clusters of cells (not shown).

EXAMPLE 7

Identification of the R1 Repeat Domain of AnxA2 as the PCSK9-Interacting Sequence To identify the specific sequence(s) of AnxA2 that mediates the interaction with PCSK9, several segments of AnxA2 were deleted/mutagenized and these constructs overexpressed (FIG. 10A) in HEK293 cells. Far Western blots of these cell lysates using PCSK9-V5 revealed that deletion of the N-terminal segment aa 2-24 of AnxA2—which is known to be necessary for binding to p11 and tissue plasminogen activator and to have other functions such as membrane bridging[28,33]—does not affect binding to PCSK9 (FIG. 10B, left panel).

Wild type human Annexin A2 (AnxA2) (ATCC #MGC-2257) and Annexin A1 (AnxA1) (ATCC #MGC-5095) were purchased from ATCC and subcloned into NheI/SacI digested pIRES2-EGFP vector. An HA epitope (YPYDVPDYA) was fused by PCR mutagenesis at the C-terminus of both AnxA1 and AnxA2. All oligonucleotides used in the various AnxA2 constructions are listed in Table 3 above. Two-steps PCRs were performed on AnxA2 cDNA to introduce point mutations (N62Q; S64A; K28S+D34N+E36S; R37S+E43H+K47M; $_{77}$RRTKK (SEQ ID NO: 26)>AATAK (SEQ ID NO: 27); $^{77}$RRTKK (SEQ ID NO: 26)>AATAA (SEQ ID NO: 28); $^{77}$RRTKKELASALK (SEQ ID NO: 29)>$^{77}$AATAAELASALA (SEQ ID NO: 30); $_{80}$KKELA (SEQ ID NO: 31)>GKPLD (SEQ ID NO: 32)), or amino acid (aa) deletions (Δ2-24, aa 2-24; ΔR1, aa 37-108; ΔR2, aa 109-192; ΔR3, aa 193-268; ΔR4, aa 269-339; Δ25-36, aa 25-36; Δ37-48, aa 37-48; Δ49-61, aa 49-61; Δ62-75, aa 62-75; Δ37-66, aa 37-66; Δ74-88, aa 74-88; Δ82-88, aa 82-88; Δ89-101, aa 89-101; Δ102-108, aa 102-108) into pIRES2-AnxA2-EGFP vector (see Table 3 above). In addition, using PCR, the AnxA2 segment aa 49-75 was swapped with the corresponding AnxA1 segment aa 58-84 [AnxA1 (aa 58-84)>AnxA2 (aa 49-75)]. Similar swaps were performed for the corresponding AnxA2 sequence with AnxA1 (AnxA1>AnxA2: aa 25-27; aa 28-30; aa 31-33; aa 34-36; aa 37-39; aa 40-42; aa 43-45; aa 46-48; aa 49-75; aa 49-61; aa 62-75). All final cDNA constructs were verified by DNA sequencing.

Deletion of the first Annexin-like repeat R1 of AnxA2 completely abrogated the interaction with PCSK9-V5 (FIGS. 10A,B) or CHRD-V5 (not shown), while deletions of the three other repeats (R2, R3, or R4) had no major effect (FIGS. 10A,B). Thus, the R1 repeat seems to be the major domain of AnxA2 implicated in PCSK9 binding. Comparison of the primary sequences of the R1 domain of AnxA2 and AnxA1— which does not bind PCSK9]—indicated areas of divergent sequences (FIG. 10C).

In further screens, replacement of the AnxA2 second loop sequence $_{80}$KKELA$_{84}$ (SEQ ID NO: 31) with the corresponding AnxA1 loop sequence $_{89}$GKPLD$_{93}$ had no appreciable effect on PCSK9 binding (FIG. 11A, right panels). However, when the $_{77}$RRTKK$_{81}$ (SEQ ID NO: 26) sequence was mutated to $^{77}$AATAK$^{81}$ (SEQ ID NO: 27) or $_{77}$AATAA$_{81}$ (SEQ ID NO: 28), Far Western blots using PCSK9-V5 showed that the integrity of the positively charged sequence $_{77}$RRTKK$_{81}$ (SEQ ID NO: 26) is critical for the AnxA2-PCSK9 binding. Replacing the $_{77}$RRTKKELASALK$_{88}$ (SEQ ID NO: 29) sequence by $_{77}$AATAAELASALA$_{88}$ (SEQ ID NO: 30) also abolished binding of AnxA2 to PCSK9 (FIG. 11A, right panels). Since the mutation of Lys$_{80}$ by Gly$_{80}$ did not affect binding, this suggests that $_{77}$RRxxK$_{81}$ is a critical motif. In addition, it was also observed that substitution of the charged amino acids Lys28, Asp34 and Glu36 by the corresponding AnxA1 Ser37, Asn43 and Ser45 slightly reduced the ability of PCSK9 to bind AnxA2, whereas substitution of residues Arg37, Glu43 and Lys47 of AnxA2 by the AnxA1 residues Ser46, His52 and Met56 showed a significant decrease of binding (FIG. 11A). Replacement of the relatively conserved segments 49-75 or 49-61 of AnxA2 by the corresponding ones of AnxA1 (aa 58-84) or (aa 58-70) abolished or reduced binding to PCSK9, respectively (FIG. 11B). It was also noticed that deletions within the R1 domain of AnxA2 (Δ25-36, Δ37-48, Δ49-61, Δ62-75, Δ37-66, Δ74-88, Δ82-88, Δ89-101, Δ102-108) also abolished PCSK9 binding by Far Western Blotting (FIG. 11A, left panels). Furthermore, sequential swaps of AnxA2 aa trio by the corresponding aligned amino acid trio of AnxA1 into full-length AnxA2, showed that the minimal recognition sequence for PCSK9 to the R1 domain of AnxA2 start at position Asp34 (FIG. 11B). Thus, by Far Western Blotting, it can be concluded that the interaction of PCSK9 with the R1 domain of AnxA2 reside from residues Asp34 to Gln108 and that it may be complex, requiring more than one structural characteristic for optimal binding on nitrocellulose membranes (FIG. 11C, bold).

EXAMPLE 8

Secreted Form of AnxA2 Repeat 1

Figures 12A, 12B:
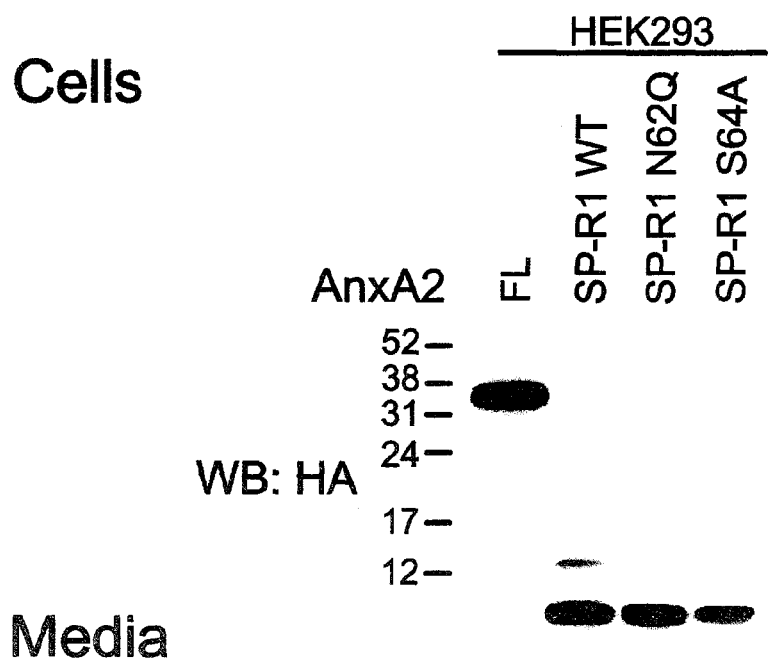
FIG. 12. Production of a secreted form of the AnxA2 R1 domain in HEK293 cells. (A) A signal peptide (SP) was added to the N-terminal tyrosine ($Y_{30}$) of AnxA2 R1 (30-108) (SEQ ID NO: 18) domain to force transit into the secretory pathway and secretion into cell media. Additionally an HA epitope was added after Glutamine 108 ($Q_{108}$) at the C-terminus of the R1 domain. A potential glycosylation site (NRS) is underlined. (B) HEK293 cells were transfected with HA-tagged full-length human AnxA2 (FL) or HA-tagged secretable forms of its R1 domain; SP-R1 wild type (WT) or glycosylation site mutants SP-R1N62Q or SP-R1S64A. Cell lysates and media were separated by SDS-PAGE (15%) and analyzed by western blotting with the anti-HA-HRP antibody.

To generate the secreted form of the repeat 1 (R1; aa 30-108) of AnxA2, the signal peptide of human PCSK9 (Seidah, PNAS, 2003) was amplified by PCR and fused to a PCR fragment containing the amino acids 30-108 of AnxA2 (see Table 3 above (SP-R1 (30-108)-HA) and FIG. 12A). Purified PCR fragments were digested with the appropriate restriction enzymes and subcloned into the corresponding digested pIRES2-AnxA2-HA-EGFP vector. All final cDNA constructs were verified by DNA sequencing.

Compared to the full-length (FL) AnxA2 that is not secreted, the addition of a signal peptide to the R1 domain of AnxA2 resulted in its secretion when overexpressed in HEK293 cells (FIG. 12B, media). The SP-R1 WT construct showed the best expression (Cells) and secretion (Media) levels compared to the glycosylation site mutants SP-R1 N62Q or SP-R1 S64A. In both cell lysate and medium, the SP-R1 WT construct is found as a glycosylated (~14 Kda) and an unglycosylated form (~9 Kda).

EXAMPLE 9

Inhibitory Activity of AnxA2-Derived Peptides on PCSK9-LDLR Interaction

AlphaScreen® (Perkin Elmer) streptavidin donor beads were coated with purified biotin-conjugated PCSK9 and AlphaScreen® nickel chelate acceptor beads were coated with purified His6-conjugated LDLR ectodomain. Competition in the AlphaScreen® PCSK9-LDLR interaction assay was measured, in the presence of increasing concentrations of AnxA2-derived peptides, as a reduction of fluorescence.

Figure 13:
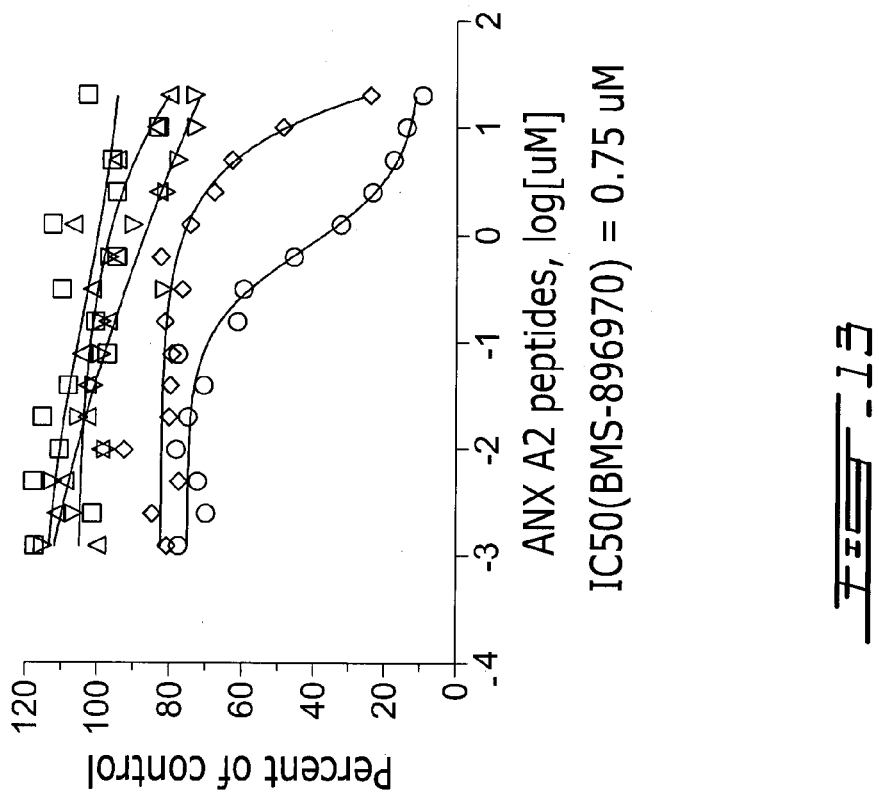
FIG. 13. Analysis of the inhibitory effect of AnxA2-derived peptides on the PCSK9:LDLR interaction. Peptide derived from the amino acid 25 to 97 (SEQ ID NO: 12) of the AnxA2 sequence represents the most potent competitor in the AlphaScreen™ PCSK9-LDLR interaction assay with an $IC_{50}$ of 0.75 μM.
Figure 15:
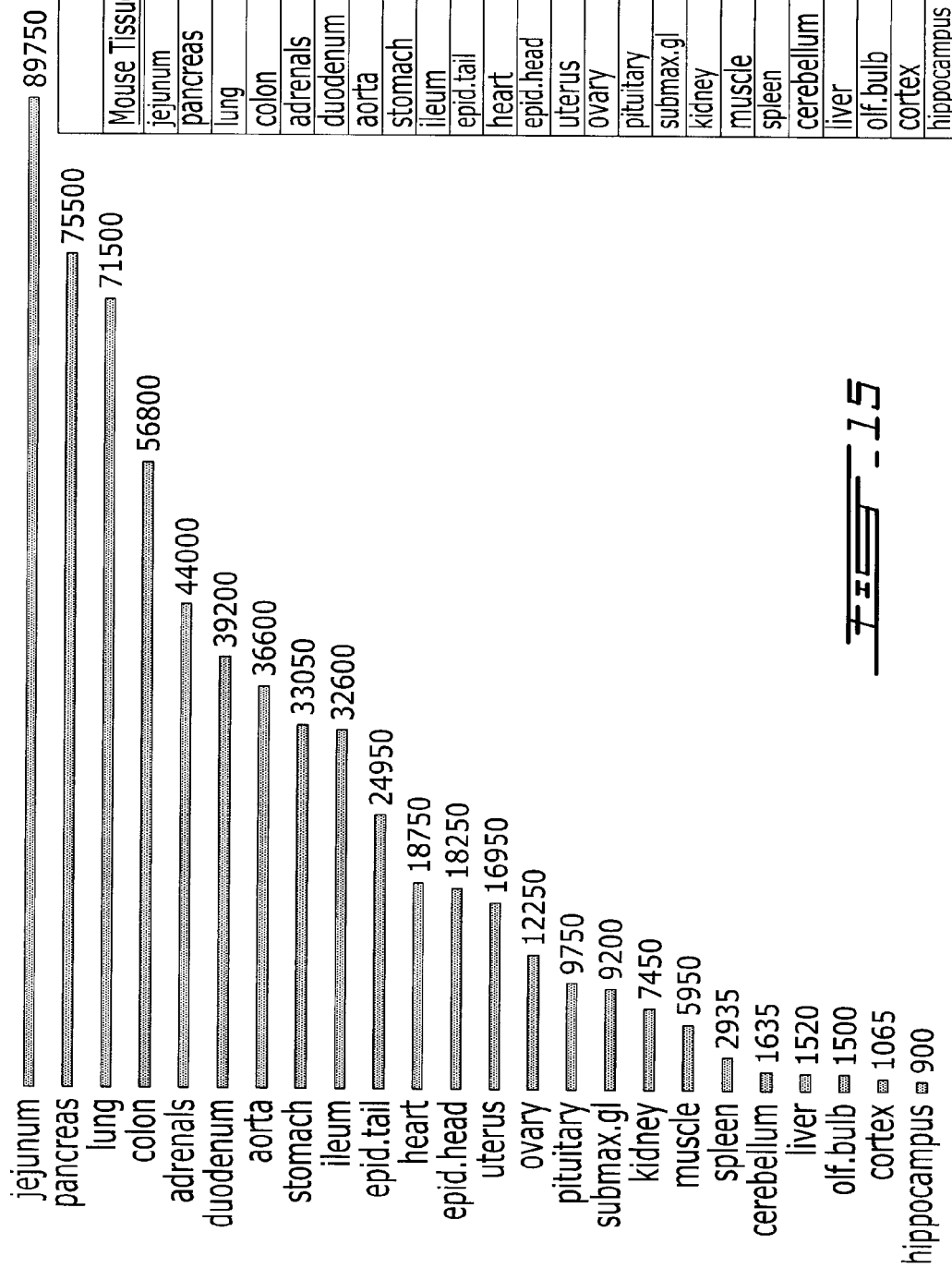
FIG. 15. Relative mRNA expression of AnxA2 in mouse tissues. Quantitative polymerase chain reactions were performed on RNA isolated from mouse tissues using specific oligonucleotides for mouse AnxA2, PCSK9 and normalized to $10^6$ S16 mRNA levels, as in FIG. 14.

In the AlphaScreen® PCSK9-LDLR interaction assay, the peptide No 896970 (a 73-mer AnxA2 R1 peptide extending from amino acids 25 to 97) showed a strong inhibition of the interaction with an IC50 of ~0.5-1 µM (FIG. 13) and up to 90% inhibition at 10 uM (not shown). The presence of a shorter peptide extending from amino acid 49 to 97 also inhibits the interaction between PCSK9 and the ectodomain of LDLR however to a lesser extent. In contrast, the corresponding alanine mutation AnxA2-derived peptide (No 894810) did not show any inhibitory activity on the PCSK9-LDLR ectodomain interaction.

EXAMPLE 10

Evaluation of PCSK9, LDLR and LDL-Cholesterol Levels in AnxA2 Knockout Mice

In vivo studies were made on wild type C57Bl/6 and homozygous annexin A2-null mice (AnxA2 KO mice)[34]. Immunoprecipitation of mouse plasma PCSK9, plasma measurements by FPLC, western blots, and immunocytochemistry were performed as described previously[11,35].

As shown in Table 4 below, an increase of ~2.8 fold in the level of PCSK9 circulating in the plasma was observed in the AnxA2 KO mice as compared to wild type mice. FPLC fractionation and subsequent cholesterol measurements revealed higher plasma LDL-cholesterol (+43%) in the AnxA2 KO mice while VLDL and HDL cholesterol levels remained similar in both wild type C57Bl/6 and AnxA2 KO mice. Western blot analysis of LDLR in adrenals, ileum, colon and liver revealed a decrease in LDLR levels in AnxA2 KO mice by 70%, 30%, 40% and 10%, respectively. Taken together these results support a physiological role for AnxA2 as an endogenous inhibitor of the PCSK9-enhanced LDLR degradation mostly in extrahepatic organs.

TABLE 4

PCSK9, LDLR and LDL-cholesterol levels in An x A2 knockout mice.

| | | Mouse genotype | | |
| --- | --- | --- | --- | --- |
| Method used | Measured levels | WT (n = 5) | A2 KO (n = 6) | Fold increase |
| Immunoprecipitation | PCSK9 plasma levels | 100% | 280% | x2.8 |
| FPLC, plasma | LDL-Cholesterol | 32.1 µg | 45.9 µg | x1.43 |
| | VLDL-Cholesterol | 8.9 µg | 8.7 µg | x1.02 |
| | HDL-Cholesterol | 142.6 µg | 139.2 µg | x0.98 |
| Western blots | LDLR levels in adrenals | 100% | ~30% | x0.3 |
| | LDLR levels in Ileum | 100% | ~60% | x0.7 |
| | LDLR levels in colon | 100% | ~70% | x0.6 |
| | LDLR levels in liver | 100% | ~90% | x0.9 |

EXAMPLE 11

Effect of 5-Azacytidine Treatment of HepG2 Cells on PCSK9, LDLR, HMGCR and AnxA2 Protein and RNA Expression Levels Quantitative RT-PCR For RNA preparation and cDNA synthesis cells were washed with PBS and incubated with Trizol reagent (Life Technologies). Total RNA was extracted and resuspended in ~30 µL of water. Isolated RNA integrity was electrophoretically verified by ethidium bromide staining and optical density. Typically, 250 ng of total RNA were used for cDNA synthesis in a total volume of 20 µL using SuperScript™ II reverse transcriptase, 25 µg/mL oligo(dT)12-18, 0.5 mmol/L 2'-deoxynucleoside 5'-triphosphates, and 40 U of RNase-OUT™, all products from Life Technologies, and used according to the recommendations of the manufacturer. All primers were designed using Primer3™ software and optimized for each amplification. Each cDNA sample was submitted to 2 polymerase chain reaction (PCR) amplifications: one for normalizing ribosomal-protein gene (S14 for human and S16 for mouse cDNAs) and the other for the gene of interest, each in triplicate. Each reaction was in a final volume of 25 µL using the QuantiTec SYBR Green™ PCR master mix from Qiagen, cDNA dilutions that gave threshold cycle (Ct) values for both amplifications, and primers for ribosomal-protein genes or the chosen target gene. Primers used for QPCR analyses are listed in Table 5 below. The Mx3500P™ system from Stratagene was used to perform and analyze the QPCR reactions, using S14 amplifications as normalizers and control samples as calibrators[25,35].

TABLE 5

Primers used for QPCR (h: human, m: mouse)

| Genes | Sense (S) | Antisense (AS) |
|---|---|---|
| hPCSK9 | 5'-ATCCACGCTTCCTGCTGC-3' (SEQ ID NO: 106) | 5'-CACGGTCACCTGC TCCTG-3' (SEQ ID NO: 107) |
| hLDLR | 5'-AGGAGACGTGCTTGTCTGTC-3' (SEQ ID NO: 108) | 5'-CTGAGCCGTTGTC GCAGT-3' (SEQ ID NO: 109) |
| hHMGCR | 5'-GTCACATGATTCACAACAGG-3' (SEQ ID NO: 110) | 5'-GTCCTTTAGAACC CAATGC-3' (SEQ ID NO: 111) |
| hAnxA2 | 5'-CAAGAGAAAGTACGGCAAGT-3' (SEQ ID NO: 112) | 5'-CTTTGGCTTACAG GAGAGAC-3' (SEQ ID NO: 113) |
| mAnxA2 | 5'-GATTAGAATCATGGTCTCTC G-3' (SEQ ID NO: 114) | 5'-TTAGTGGAGAGCG AAGTCTC-3' (SEQ ID NO: 115) |
| hS14 | 5'-GGCAGACCGAGATGAATCCT CA-3' (SEQ ID NO: 116) | 5'-CAGGTCCAGGGGT CTTGGTCC-3' (SEQ ID NO: 117) |
| mS16 | 5'-AGGAGCGATTTGCTGGTGTG G-3' (SEQ ID NO: 118) | 5'-GCTACCAGGGCCT TTGAGATG-3' (SEQ ID NO: 119) |

5-Azacytidine treatment of HepG2 cells led to an increased expression of AnxA2 and LDLR and a strong inhibition of PCSK9 expression both at the protein and mRNA levels (FIG. 16A,B). Untreated control (Ctl) HepG2 cells bears low levels of AnxA2 mRNA and undetectable protein content but upon treatment with 5-Azacytidine (10 µM) AnxA2 mRNA expression was raised by 3 fold (FIG. 16 B) and was also highly increased at the protein level (FIG. 16 A). These data shows that 5-Azacytidine represents an agent able to increase the level of AnxA2 in hepatic-derived cells. Additionally, the secreted form of PCSK9 was barely detectable by western blot either after 24 or 48 hours of treatment. This could be due in part to the increase of AnxA2 expression and activity. However, the mRNA level of PCSK9 was also drastically decreased following the 5-Azacytidine treatment suggesting that additional factors could be involved. Interestingly, the qPCR results showed in addition that the HMG-CoA reductase mRNA level was decreased whereas that of LDLR was increased following 5-Azacytidine treatment. Taken together, these results show that 5-Azacytidine treatment of HepG2 cells affects at least four genes involved in the cholesterol homeostasis, namely by inducing an increase of AnxA2 and LDLR and a decrease of PCSK9 and HMGCR. In each case, the changes observed are those known to be associated with a desirable decrease in circulating LDL-cholesterol.

Although the present invention has been described herein above by way of specific embodiments thereof, it can be modified, without departing from the spirit and nature of the subject invention as defined in the appended claims.

REFERENCES

1. Seidah, N. G., Benjannet, S., Wickham, L., Marcinkiewicz, J., Jasmin, S. B., Stifani, S., Basak, A., Prat, A., and Chretien, M. The secretory proprotein convertase neural apoptosis-regulated convertase 1 (NARC-1): liver regeneration and neuronal differentiation. Proc. Natl. Acad. Sci. U.S.A, 100: 928-933, 2003.
2. Seidah, N. G., Mayer, G., Zaid, A., Rousselet, E., Nassoury, N., Poirier, S., Essalmani, R., and Prat, A. The activation and physiological functions of the proprotein convertases. Int. J. Biochem. Cell Biol., 40: 1111-1125, 2008.
3. Seidah, N. G. and Prat, A. The proprotein convertases are potential targets in the treatment of dyslipidemia. J. Mol. Med., 85: 685-696, 2007.
4. Benjannet, S., Rhainds, D., Essalmani, R., Mayne, J., Wickham, L., Jin, W., Asselin, M. C., Hamelin, J., Varret, M., Allard, D., Trillard, M., Abifadel, M., Tebon, A., Attie, A. D., Rader, D. J., Boileau, C., Brissette, L., Chretien, M., Prat, A., and Seidah, N. G. NARC-1/PCSK9 and its natural mutants: zymogen cleavage and effects on the low density lipoprotein (LDL) receptor and LDL cholesterol. J. Biol. Chem., 279: 48865-48875, 2004.
5. Maxwell, K. N. and Breslow, J. L. Adenoviral-mediated expression of Pcsk9 in mice results in a low-density lipoprotein receptor knockout phenotype. Proc. Natl. Acad. Sci. U.S.A, 101: 7100-7105, 2004.
6. Abifadel, M., Varret, M., Rabes, J. P., Allard, D., Ouguerram, K., Devillers, M., Cruaud, C., Benjannet, S., Wickham, L., Erlich, D., Derre, A., Villeger, L., Farnier, M., Beucler, I., Bruckert, E., Chambaz, J., Chanu, B., Lecerf, J. M., Luc, G., Moulin, P., Weissenbach, J., Prat, A., Krempf, M., Junien, C., Seidah, N. G., and Boileau, C. Mutations in PCSK9 cause autosomal dominant hypercholesterolemia. Nat. Genet., 34: 154-156, 2003.
7. Kathiresan, S., Melander, O., Guiducci, C., Surti, A., Burtt, N. P., Rieder, M. J., Cooper, G. M., Roos, C., Voight, B. F., Havulinna, A. S., Wahlstrand, B., Hedner, T., Corella, D., Tai, E. S., Ordovas, J. M., Berglund, G., Vartiainen, E., Jousilahti, P., Hedblad, B., Taskinen, M. R., Newton-Cheh, C., Salomaa, V., Peltonen, L., Groop, L., Altshuler, D. M., and Orho-Melander, M. Six new loci associated with blood low-density lipoprotein cholesterol, high-density lipoprotein cholesterol or triglycerides in humans. Nat. Genet., 40: 189-197, 2008.
8. Willer, C. J., Sanna, S., Jackson, A. U., Scuteri, A., Bonnycastle, L. L., Clarke, R., Heath, S. C., Timpson, N. J., Najjar, S. S., Stringham, H. M., Strait, J., Duren, W. L., Maschio, A., Busonero, F., Mulas, A., Albai, G., Swift, A. J., Morken, M. A., Narisu, N., Bennett, D., Parish, S., Shen, H., Galan, P., Meneton, P., Hercberg, S., Zelenika, D., Chen, W. M., Li, Y., Scott, L. J., Scheet, P. A., Sundvall, J., Watanabe, R. M., Nagaraja, R., Ebrahim, S., Lawlor, D. A., Ben Shlomo, Y., Davey-Smith, G., Shuldiner, A. R., Collins, R., Bergman, R. N., Uda, M., Tuomilehto, J., Cao, A., Collins, F. S., Lakatta, E., Lathrop, G. M., Boehnke, M., Schlessinger, D., Mohike, K. L., and Abecasis, G. R. Newly identified loci that influence lipid concentrations and risk of coronary artery disease. Nat. Genet., 40: 161-169, 2008.

9. Schadt, E. E., Molony, C., Chudin, E., Hao, K., Yang, X., Lum, P. Y., Kasarskis, A., Zhang, B., Wang, S., Suver, C., Zhu, J., Millstein, J., Sieberts, S., Lamb, J., Guhathakurta, D., Derry, J., Storey, J. D., Avila-Campillo, I., Kruger, M. J., Johnson, J. M., Rohl, C. A., van Nas, A., Mehrabian, M., Drake, T. A., Lusis, A. J., Smith, R. C., Guengerich, F. P., Strom, S. C., Schuetz, E., Rushmore, T. H., and Ulrich, R. Mapping the genetic architecture of gene expression in human liver. PLoS. Biol., 6: e107, 2008.

10. Rashid, S., Curtis, D. E., Garuti, R., Anderson, N. N., Bashmakov, Y., Ho, Y. K., Hammer, R. E., Moon, Y. A., and Horton, J. D. Decreased plasma cholesterol and hypersensitivity to statins in mice lacking Pcsk9. Proc. Natl. Acad. Sci. U.S.A, 102: 5374-5379, 2005.

11. Zaid, A., Roubtsova, A., Essalmani, R., Marcinkiewicz, J., Chamberland, A., Hamelin, J., Tremblay, M., Jacques, H., Jin, W., Davignon, J., Seidah, N. G., and Prat, A. Proprotein convertase subtilisin/kexin type 9 (PCSK9): Hepatocyte-specific low-density lipoprotein receptor degradation and critical role in mouse liver regeneration. Hepatology, 48: 646-654, 2008.

12. McNutt, M. C., Lagace, T. A., and Horton, J. D. Catalytic activity is not required for secreted PCSK9 to reduce low density lipoprotein receptors in HepG2 cells. J. Biol. Chem., 282: 20799-20803, 2007.

13. Cameron, J., Holla, O. L., Ranheim, T., Kulseth, M. A., Berge, K. E., and Leren, T. P. Effect of mutations in the PCSK9 gene on the cell surface LDL receptors. Hum. Mol. Genet., 15: 1551-1558, 2006.

14. Park, S. W., Moon, Y. A., and Horton, J. D. Post-transcriptional regulation of low density lipoprotein receptor protein by proprotein convertase subtilisin/kexin type 9a in mouse liver. J. Biol. Chem., 279: 50630-50638, 2004.

15. Nassoury, N., Blasiole, D. A., Tebon, O. A., Benjannet, S., Hamelin, J., Poupon, V., McPherson, P. S., Attie, A. D., Prat, A., and Seidah, N. G. The Cellular Trafficking of the Secretory Proprotein Convertase PCSK9 and Its Dependence on the LDLR. Traffic., 8: 718-732, 2007.

16. Li, J., Tumanut, C., Gavigan, J. A., Huang, W. J., Hampton, E. N., Tumanut, R., Suen, K. F., Trauger, J. W., Spraggon, G., Lesley, S. A., Liau, G., Yowe, D., and Harris, J. L. Secreted PCSK9 promotes LDL receptor degradation independently of proteolytic activity. Biochem. J., 406: 203-207, 2007.

17. Poirier, S., Mayer, G., Benjannet, S., Bergeron, E., Marcinkiewicz, J., Nassoury, N., Mayer, H., Nimpf, J., Prat, A., and Seidah, N. G. The proprotein convertase PCSK9 induces the degradation of low density lipoprotein receptor (LDLR) and its closest family members VLDLR and ApoER2. J. Biol. Chem., 283: 2363-2372, 2008.

18. Cunningham, D., Danley, D. E., Geoghegan, K. F., Griffor, M. C., Hawkins, J. L., Subashi, T. A., Varghese, A. H., Ammirati, M. J., Culp, J. S., Hoth, L. R., Mansour, M. N., McGrath, K. M., Seddon, A. P., Shenolikar, S., Stutzman-Engwall, K. J., Warren, L. C., Xia, D., and Qiu, X. Structural and biophysical studies of PCSK9 and its mutants linked to familial hypercholesterolemia. Nat. Struct. Mol. Biol., 14: 413-419, 2007.

19. Zhang, D. W., Lagace, T. A., Garuti, R., Zhao, Z., McDonald, M., Horton, J. D., Cohen, J. C., and Hobbs, H. H. Binding of proprotein convertase subtilisin/kexin type 9 to epidermal growth factor-like repeat a of low density lipoprotein receptor decreases receptor recycling and increases degradation. J. Biol. Chem., 282: 18602-18612, 2007.

20. Cohen, J., Pertsemlidis, A., Kotowski, I. K., Graham, R., Garcia, C. K., and Hobbs, H. H. Low LDL cholesterol in individuals of African descent resulting from frequent nonsense mutations in PCSK9. Nat. Genet., 37: 161-165, 2005.

21. Labonte, P., Begley, S., Guevin, C., Asselin, M.-C., Nassoury, N., Mayer, G., Prat, A., and Seidah, N. G. PCSK9 impedes HCV infection in vitro and modulates liver CD81 expression. Hepatoplogy (in press), 2009.

22. Chetcuti, A., Margan, S. H., Russell, P., Mann, S., Millar, D. S., Clark, S. J., Rogers, J., Handelsman, D. J., and Dong, Q. Loss of annexin II heavy and light chains in prostate cancer and its precursors. Cancer Res., 61: 6331-6334, 2001.

23. Benjannet, S., Rhainds, D., Hamelin, J., Nassoury, N., and Seidah, N. G. The proprotein convertase PCSK9 is inactivated by furin and/or PC5/6A: Functional consequences of natural mutations and post-translational modifications. J. Biol. Chem., 281: 30561-30572, 2006.

24. Nour, N., Basak, A., Chretien, M., and Seidah, N. G. Structure-Function Analysis of the Prosegment of the Proprotein Convertase PC5A. J. Biol. Chem., 278: 2886-2895, 2003.

25. Dubuc, G., Chamberland, A., Wassef, H., Davignon, J., Seidah, N. G., Bernier, L., and Prat, A. Statins upregulate PCSK9, the gene encoding the proprotein convertase neural apoptosis-regulated convertase-1 implicated in familial hypercholesterolemia. Arterioscler. Thromb. Vasc. Biol., 24: 1454-1459, 2004.

26. Mayer, G., Hamelin, J., Asselin, M. C., Pasquato, A., Marcinkiewicz, E., Tang, M., Tabibzadeh, S., and Seidah, N. G. The regulated cell surface zymogen activation of the proprotein convertase PC5A directs the processing of its secretory substrates. J. Biol. Chem., 283: 2373-2384, 2008.

27. Gorg, A., Obermaier, C., Boguth, G., Harder, A., Scheibe, B., Wildgruber, R., and Weiss, W. The current state of two-dimensional electrophoresis with immobilized pH gradients. Electrophoresis, 21: 1037-1053, 2000.

28. Kassam, G., Le, B. H., Choi, K. S., Kang, H. M., Fitzpatrick, S. L., Louie, P., and Waisman, D. M. The p11 subunit of the annexin II tetramer plays a key role in the stimulation of t-PA-dependent plasminogen activation. Biochemistry, 37: 16958-16966, 1998.

29. Kotowski, I. K., Pertsemlidis, A., Luke, A., Cooper, R. S., Vega, G. L., Cohen, J. C., and Hobbs, H. H. A Spectrum of PCSK9 Alleles Contributes to Plasma Levels of Low-Density Lipoprotein Cholesterol. Am. J. Hum. Genet., 78: 410-422, 2006.

30. Siever, D. A. and Erickson, H. P. Extracellular annexin II. Int. J. Biochem. Cell Biol., 29: 1219-1223, 1997.

31. Mai, J., Waisman, D. M., and Sloane, B. F. Cell surface complex of cathepsin B/annexin II tetramer in malignant progression. Biochim. Biophys. Acta, 1477: 215-230, 2000.

32. Horton, J. D., Cohen, J. C., and Hobbs, H. H. Molecular biology of PCSK9: its role in LDL metabolism. Trends Biochem. Sci., 32: 71-77, 2007.

33. Zibouche, M., Vincent, M., Illien, F., Gallay, J., and Ayala-Sanmartin, J. The N-terminal domain of annexin 2 serves as a secondary binding site during membrane bridging. J. Biol. Chem., 2008.

34. Ling, Q., Jacovina, A. T., Deora, A., Febbraio, M., Simantov, R., Silverstein, R. L., Hempstead, B., Mark, W. H., and Najjar, K. A. Annexin II regulates fibrin homeostasis and neoangiogenesis in vivo. J. Clin. Invest, 113: 38-48, 2004.

35. Mayer, G., Poirier, S., and Seidah, N. G. Annexin A2 is a C-terminal PCSK9-binding protein that regulates endogenous low density lipoprotein receptor levels. J Biol. Chem., 283: 31791-31801, 2008.

36. Zhang D W, Garuti R, Tang W J, Cohen J C, Hobbs H H. Proc Natl Acad Sci USA 2008; 105:13045-13050.

37. Mayer G, Poirier S, Seidah N G. J Biol Chem 2008; 283:31791-31801.

The invention claimed is:

1. A method of inhibiting PCSK9-induced LDLR degradation, or PCSK9-induced VLDLR degradation, PCSK9-induced ApoER2 degradation or PCSK9-induced CD81 degradation comprising contacting a cell expressing LDLR, VLDLR or ApoER2 with an inhibitor that is:
   a) a polypeptide comprising amino acids of full length AnxA2 isoform 1 or 2 (SEQ ID NO: 1 or 2) or 34-88 of AnxA2 (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22);
   b) a functional derivative, analogue, or conjugate of a);
   c) 5-azacytidine or decitabine;
   d) a polypeptide ligand to PCSK9 C-terminal Cys-His-rich-domain (CHRD)
   e) a polypeptide ligand to PCSK9 CHRD's second subdomain module M2;
   f) p11; or
   g) a combination of any of the above.

2. The method of claim 1, wherein the inhibitor is the polypeptide comprising amino acids of full length AnxA2 isoform 1 or 2 (SEQ ID NO: 1 or 2) or 34-88 of AnxA2 (numbering of amino acids used hereinbelow is in reference to that of isoform 2) (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22).

3. The method of claim 1, wherein the activator of Annexin A2 is 5-azacytidine.

4. The method of claim 2, wherein the polypeptide is Annexin A2.

5. The method of claim 2, further comprising p11.

6. The method of claim 2, wherein the method inhibits PCSK9-induced LDLR degradation.

7. A combination of a compound and of a cholesterol synthesis inhibitor, wherein the compound is:
   a) a polypeptide comprising amino acids of full length AnxA2 isoform 1 or 2 (SEQ ID NO: 1 or 2) or 34-88 of AnxA2 (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22); or
   b) a functional derivative, analogue, conjugate or prodrug of a); or
   c) 5-azacytidine or decitabine; or
   d) a polypeptide ligand to PCSK9 C-terminal Cys-His-rich-domain (CHRD); or
   e) a polypeptide ligand to PCSK9 CHRD's second subdomain module M2; or
   f) p11; or
   g) a combination of any of the above.

8. A commercial kit comprising a polypeptide comprising amino acids of full length AnxA2 isoform 1 or 2 (SEQ ID NO: 1 or 2) or 34-88 of AnxA2 (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) and a cholesterol synthesis inhibitor.

9. A commercial kit comprising 5-azacytidine or decitabine and a cholesterol synthesis inhibitor.

10. A purified polypeptide comprising amino acids of 34-88 of AnxA2 (SEQ ID NO:3) or 34-97 of AnxA2 (SEQ ID NO:4) or 34-102 of AnxA2 (SEQ ID NO:5) or 34-108 of AnxA2 (SEQ ID NO:6) or 37-88 of AnxA2 (SEQ ID NO:7) or 37-97 of AnxA2 (SEQ ID NO:8) or 37-102 of AnxA2 (SEQ ID NO:9) or 37-108 of AnxA2 (SEQ ID NO:10) or 25-88 of AnxA2 (SEQ ID NO:11) or 25-97 of AnxA2 (SEQ ID NO:12) or 25-102 of AnxA2 (SEQ ID NO:13) or 25-108 of AnxA2 (SEQ ID NO:14) or 30-88 of AnxA2 (SEQ ID NO:15) or 30-97 of AnxA2 (SEQ ID NO:16) or 30-102 of AnxA2 (SEQ ID NO:17) or 30-108 of AnxA2 (SEQ ID NO:18) or 49-88 of AnxA2 (SEQ ID NO:19) or 49-97 of AnxA2 (SEQ ID NO:20) or 49-102 of AnxA2 (SEQ ID NO:21) or 49-108 of AnxA2 (SEQ ID NO:22) with the proviso that said polypeptide is not as set forth in SEQ ID NO: 1 or 2.

11. A pharmaceutical composition comprising the polypeptide of claim 10, and a pharmaceutically acceptable carrier.

* * * * *